(12) United States Patent
Fenwick et al.

(10) Patent No.: US 7,115,616 B2
(45) Date of Patent: *Oct. 3, 2006

(54) PYRIMIDINONE COMPOUNDS

(75) Inventors: Ashley Edward Fenwick, Sandwich (GB); Deirdre Mary Bernadette Hickey, Stevenage (GB); Robert John Ife, Stevenage (GB); Colin Andrew Leach, Stevenage (GB); Ivan Leo Pinto, Stevenage (GB); Stephen Allan Smith, Stevenage (GB)

(73) Assignee: SmithKline Beecham Plc, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/776,876

(22) Filed: Feb. 11, 2004

(65) Prior Publication Data

US 2004/0167142 A1    Aug. 26, 2004

Related U.S. Application Data

(62) Division of application No. 10/030,661, filed as application No. PCT/EP00/03727 on Apr. 25, 2000, now Pat. No. 6,953,803.

(30) Foreign Application Priority Data

May 1, 1999  (GB) ................. 9910048.9
Jan. 28, 2000  (GB) ................. 0002096.6

(51) Int. Cl.
C07D 473/00 (2006.01)
C07D 239/02 (2006.01)
A61K 31/505 (2006.01)
A61P 9/10 (2006.01)

(52) U.S. Cl. ............ 514/269; 514/274; 544/296; 544/310; 544/311

(58) Field of Classification Search ............ 514/269, 514/274; 544/310, 311, 296
See application file for complete search history.

(56) References Cited

U.S. PATENT DOCUMENTS 6,953,803 B1 * 10/2005 Hickey et al. ............ 514/274

FOREIGN PATENT DOCUMENTS

| GB | 1 582 527 | 1/1981 |
|----|-----------|--------|
| WO | WO 99/24420 | 5/1999 |
| WO | WO 00/10980 | 3/2000 |

* cited by examiner

*Primary Examiner*—Bruck Kifle
(74) *Attorney, Agent, or Firm*—James M. Kanagy; Stephen Venetianer; Charles M. Kinzig

(57) ABSTRACT

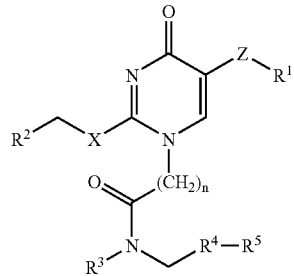

(1)

Pyrimidinone compounds of formula (10 are inhibitors of the enzyme Lp-PLA$_2$ and of use in therapy, in particular for treating atherosclerosis.

18 Claims, No Drawings

PYRIMIDINONE COMPOUNDS

This application is a divisional of application Ser. No. 10/030,661 filed Apr. 22, 2002 now U.S. Pat. No. 6,953,803, which is the National Stage of International Application No. PCT/EP00/03727 filed on Apr. 25, 2000.

The present invention relates to certain novel pyrimidinone compounds, processes for their preparation, intermediates useful in their preparation, pharmaceutical compositions containing them and their use in therapy, in particular in the treatment of atherosclerosis.

WO 95/00649 (SmithKline Beecham plc) describe the phospholipase A2 enzyme Lipoprotein Associated Phospholipase $A_2$ (Lp-$PLA_2$), the sequence, isolation and purification thereof, isolated nucleic acids encoding the enzyme, and recombinant host cells transformed with DNA encoding the enzyme. Suggested therapeutic uses for inhibitors of the enzyme included atherosclerosis, diabetes, rheumatoid arthritis, stroke, myocardial infarction, reperfusion injury and acute and chronic inflammation. A subsequent publication from the same group further describes this enzyme (Tew D et al, Arterioscler Thromb Vas Biol 1996: 16;591–9) wherein it is referred to as LDL-$PLA_2$. A later patent application (WO 95/09921, Icos Corporation) and a related publication in Nature (Tjoelker et al, vol 374, 6 Apr. 1995, 549) describe the enzyme PAF-AH which has essentially the same sequence as Lp-$PLA_2$ and suggest that it may have potential as a therapeutic protein for regulating pathological inflammatory events.

It has been shown that Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-$PLA_2$ action are biologically active with lysophosphatidylcholine, a component of oxidised LDL, known to be a potent chemoattractant for circulating monocytes. As such, lysophosphatidylcholine is thought play a significant role in atherosclerosis by being responsible for the accumulation of cells loaded with cholesterol ester in the arteries. Inhibition of the Lp-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

The increased lysophosphatidylcholine content of oxidatively modified LDL is also thought to be responsible for the endothelial dysfunction observed in patients with atherosclerosis. Inhibitors of Lp-$PLA_2$ could therefore prove beneficial in the treatment of this phenomenon. An Lp-$PLA_2$ inhibitor could also find utility in other disease states that exhibit endothelial dysfunction including diabetes, hypertension, angina pectoris and after ischaemia and reperfusion.

In addition, Lp-$PLA_2$ inhibitors may also have a general application in any disorder that involves activated monocytes, macrophages or lymphocytes, as all of these cell types express Lp-$PLA_2$. Examples of such disorders include psoriasis.

Furthermore, Lp-$PLA_2$ inhibitors may also have a general application in any disorder that involves lipid oxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, reperfusion injury and acute and chronic inflammation. Further such conditions include vari us neuropsychiatric disorders such as schizophrenia (see Psychopharmacology Bulletin, 31, 159–165, 1995).

Patent applications WO 96/12963, WO 96/13484, WO96/19451, WO 97/02242, WO97/217675, WO97/217676, WO 96/41098, and WO97/41099 (SmithKline Beecham plc) disclose inter alia various series of 4-thionyl/sulfinyl/sulfonyl azetidinone compounds which are inhibitors of the enzyme Lp-$PLA_2$. These are irreversible, acylating inhibitors (Tew et al, Biochemistry, 37, 10087, 1998).

Patent applications WO 99/24420 and WO 00/10980 (SmithKline Beecham plc, published after the priority date of the present application) describe a new class of reversible, non-acylating inhibitors of the enzyme Lp-$PLA_2$, in particular a class of pyrimidone compounds. The early 2-(alkylthio) pyrimidin-4-one chemical lead is described in Bioorganic and Medicinal Chemistry Letters, 2000, 10, 395–8.

A further class of pyrimidone compounds has now been identified which are inhibitors of the enzyme Lp-$PLA_2$.

Accordingly, the present invention provides a compound of formula (I):

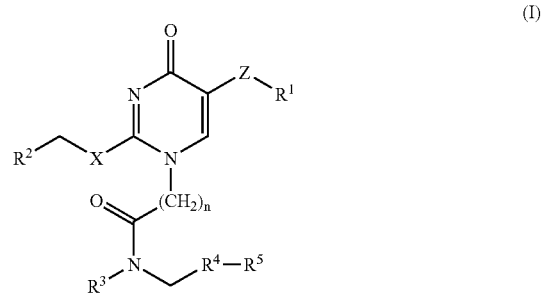

in which:

$R^1$ is an aryl or heteroaryl group, optionally substituted by 1, 2, 3 or 4 substituents which may be the same or different selected from $C_{(1-18)}$alkyl $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl and mono to perfluoro-$C_{(1-4)}$alkoxy, or, as a single substituent, optionally in combination with a further substituent as hereinbefore defined, $CH_2COOH$ or a salt thereof, $CH_2COOR^8$, $CH_2CONR^9R^{10}$, $CH_2CN$, $(CH_2)_mNR^9R^{10}$, $(CH_2)_mOH$ or $(CH_2)_mOR^6$ where m is an integer from 1 to 3;

$R^2$ is an aryl or heteroaryl group, optionally substituted by 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl, mono to perfluoro-$C_{(1-4)}$alkoxy, and aryl $C_{(1-4)}$alkyl;

$R^3$ is hydrogen or $C_{(1-4)}$alkyl which may be unsubstituted or substituted by hydroxy, $OR^6$, $COR^6$, carboxy, $COOR^6$, $CONR^9R^{10}$, $NR^9R^{10}$, mono- or di-(hydroxy $C_{(1-6)}$alkyl)amino or N-hydroxy$C_{(1-6)}$alkyl-N—$C_{(1-6)}$alkyl amino;

$R^4$ is an aryl or a heteroaryl ring optionally substituted by 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl and mono to perfluoro-$C_{(1-4)}$alkoxy;

$R^5$ is an aryl ring which is further optionally substituted by 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl and mono to perfluoro-$C_{(1-4)}$alkoxy;

$R^6$ and $R^7$ are independently hydrogen or $C_{(1-20)}$alkyl, for instance $C_{(1-4)}$alkyl (e.g. methyl or ethyl);

$R^8$ is $C_{(1-4)}$alkyl or a pharmaceutically acceptable in vivo hydrolysable ester group;

$R^9$ and $R^{10}$ which may be the same or different is each selected from hydrogen, $C_{(1-12)}$alkyl, $CH_2R^{11}$, $CHR^{12}CO_2H$ or a salt thereof, or $R^9$ and $R^{10}$ together with the nitrogen to which they are attached form a 4- to 7-, preferably 5- to 7-, membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylCO, aryl, e.g. phenyl, or aralkyl, e.g benzyl, for instance morpholine or piperazine;

$R^{11}$ is COOH or a salt thereof, $COOR^8$, $CONR^6R^7$, CN, $CH_2OH$ or $CH_2OR^6$;

$R^{12}$ is an amino acid side chain such as $CH_2OH$ from serine;

n is an integer from 1 to 4, preferably 1 or 3;

X is O or S; and

Z is $CR^{13}R^{14}$ where $R^{13}$ and $R^{14}$ are each hydrogen or $C_{(1-4)}$alkyl, or $R^{13}$ and $R^{14}$ together with the intervening carbon atom form a $C_{(3-6)}$cycloalkyl ring.

Preferably, Z is $CH_2$.

Representative examples of $R^1$ when an aryl group include phenyl and naphthyl.

Representative examples of $R^1$ when a heteroaryl group include a 5- or 6-membered, monocyclic heteroaryl group comprising 1 or 2 nitrogen heteroatoms.

Preferably, $R^1$ is pyrimidyl optionally substituted by 1 or 2 substituents preferably selected from oxo, aryl$C_{(1-4)}$alkyl (e.g. benzyl), $C_{(1-6)}$alkyl (e.g. methyl or ethyl), $C_{(3-6)}$cycloalkyl, hydroxy, $C_{(1-4)}$alkoxy (e.g. methoxy), carboxy $C_{(1-6)}$alkyl, $C_{(1-6)}$alkylcarboxy$C_{(1-6)}$alkyl, di-$C_{(1-6)}$alkylamino, and morpholino; or pyrazolyl optionally substituted by $C_{(1-6)}$alkyl (e.g. methyl or ethyl).

Preferably, $ZR^1$ is pyrimid-5-ylmethyl optionally substituted by 2-methoxy, 2-trifluoromethyl, 2-(4-morpholino) or 2-dimethylamino; 2-oxo-pyrimid-5-ylmethyl or 1-methyl-4-pyrazolylmethyl.

Preferably X is S.

Representative examples of $R^2$ when an aryl group include phenyl and naphthyl. Representative examples of $R^2$ when a heteroaryl group include pyridyl, pyrimidinyl, pyrazolyl, furanyl, thienyl, thiazolyl, quinolyl, benzothiazolyl, pyridazolyl and pyrazinyl. Preferably, $R^2$ is phenyl optionally substituted by halogen.

Representative examples of $R^2CH_2X$ include 4-fluorobenzylthio.

Representative examples of $R^3$ include hydrogen; and methyl, ethyl and propyl, optionally substituted by amino, $C_{(1-3)}$alkylamino, di $C_{(1-3)}$alkyl amino, hydroxy$C_{(1-3)}$alkylamino, hydroxy, $C_{(1-3)}$alkoxy, carboxy, $C_{(1-3)}$alkylcarboxy, and heterocycyl such as piperidino, piperazino, pyrrolidono and morpholino, wherein the alkyl moiety, if present, is,preferably methyl, or ethyl.

Representative examples of $R^4$ include phenyl optionally substituted by halogen; thiophene; pyridine; and pyrimidine.

Representative examples of $R^5$ include phenyl optionally substituted by halogen, trifluoromethyl, or trifluoromethoxy, preferably at the 4-position.

Preferably, $R^4$ and $R^5$ together form a 4-(phenyl)phenyl substituent in which the remote phenyl ring may be optionally substituted by halogen or trifluoromethyl, preferably at the 4-position.

Pharmaceutically acceptable in vivo hydrolysable ester groups for $R^8$ include those which break down readily in the human body to leave the parent acid or its salt.

Representative examples of values of pharmaceutically acceptable in vivo hydrolysable ester groups for $R^8$ include:

—$CH(R^a)O.CO.R^b$;

—$CH(R^a)O.CO.OR^c$;

—$CH(R^a)CO.NR^eR^f$;

—$R^dNR^eR^f$;

—$CH_2OR^g$;

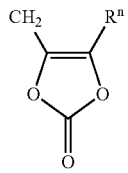

$CH(R^a)O.CO.C_6H_4Y^1COCH(R^i)NH_2$; and

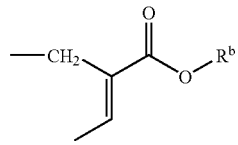

in which:

$R^a$ is hydrogen, $(C_{1-6})$alkyl, in particular methyl, $(C_{3-7})$cycloalkyl, or phenyl, each of which may be optionally substituted;

$R^b$ is $(C_{1-6})$alkyl, $(C_{1-6})$alkoxy$(C_{1-6})$alkyl, phenyl, benzyl, $(C_{3-7})$cycloalkyl, $(C_{1-6})$alkyl$(C_{3-7})$cycloalkyl, 1-amino $(C_{1-6})$alkyl, or 1-$(C_{1-6}$alkyl)amino$(C_{1-6})$alkyl, each of which may be optionally substituted; or $R^a$ and $R^b$ together form a 1,2-phenylene group optionally substituted by one or two methoxy groups;

$R^c$ is $(C_{1-6})$alkyl, $(C_{3-7})$cycloalkyl, $(C_{1-6})$alkyl$(C_{3-7})$cycloalkyl;

$R^d$ is $(C_{1-6})$alkylene optionally substituted with a methyl or ethyl group;

$R^e$ and $R^f$ which may be the same or different is each $(C_{1-6})$alkyl; or aryl$(C_{1-4})$alkyl, optionally substituted with e.g. hydroxy;

$R^g$ is $(C_{1-6})$alkyl;

$R^h$ is hydrogen, $(C_{1-6})$alkyl or phenyl;

$R^i$ is hydrogen or phenyl optionally substituted by up to three groups selected from halogen, $(C_{1-6})$-alkyl, or $(C_{1-6})$alkoxy;

and $Y^1$ is oxygen or NH;

for instance:

(a) acyloxyalkyl groups such as acetoxymethyl, isobutyryloxymethyl, pivaloyloxymethyl, benzoyloxymethyl, α-acetoxyethyl, α-pivaloyloxyethyl, 1-(cyclohexylcarbonyloxy)ethyl, (1-aminoethyl)carbonyloxymethyl, 2-methoxyprop-2-ylcarbonyloxymethyl, phenylcarbonyloxymethyl and 4-methoxyphenyl-carbonyloxymethyl;

(b) alkoxy/cycloalkoxycarbonyloxyalkyl groups, such as ethoxycarbonyloxymethyl, t-butyloxycarbonyloxymethyl, cyclohexyloxycarbonyloxymethyl, 1-methylcyclohexyloxycarbonyloxymethyl and α-ethoxycarbonyloxyethyl;

(c) dialkylaminoalkyl, especially di-loweralkylamino alkyl groups such as dimethylaminoethyl, dimethylaminoethyl, diethylaminomethyl or diethylaminoethyl;

(d) acetamido groups such as N,N-dimethylaminocarbonylmethyl, N,N-(2-hydroxyethyl)aminocarbonylmethyl;

(e) lactone groups such as phthalidyl and dimethoxyphthalidyl;

(f) (5-methyl-2-oxo-1,3-dioxolen-4-yl)methyl; and (g) (2-methoxycarbonyl-E-but-2-en-yl)methyl.

Representative examples of pharmaceutically acceptable in vivo hydrolysable ester groups for $R^8$ include:

(2-methoxycarbonyl-E-but-2-en-yl)methyl, isobutyryloxymethyl, 2-methoxyprop-2-ylcarbonyloxymethyl, phenylcarbonyloxymethyl, 4-methoxyphenyl-carbonyloxymethyl, t-butyloxycarbonyloxymethyl, cyclohexyloxy-carbonyloxymethyl, 1-methylcyclohexyloxycarbonyloxymethyl, N,N-dimethylaminocarbonylmethyl, and (5-methyl-2-oxo-1,3-dioxolen-4-yl)methyl.

It will be appreciated that in some instances, compounds of the present invention may include a basic function such as an amino group as a substituent. Such basic functions may be used to form acid addition salts, in particular pharmaceutically acceptable salts. Pharmaceutically acceptable salts include those described by Berge, Bighley, and Monkhouse, *J. Pharm. Sci.*, 1977, 66, 1–19. Such salts may be formed from inorganic and organic acids. Representative examples thereof include maleic, fumaric, benzoic, ascorbic, pamoic, succinic, bismethylenesalicylic, methanesulfonic, p-toluenesulfonic, ethanedisulfonic, acetic, propionic, tartaric, salicylic, citric, gluconic, aspartic, stearic, palmitic, itaconic, glycolic, p-aminobenzoic, glutamic, taurocholic acid, benzenesulfonic, hydrochloric, hydrobromic, sulfuric, cyclohexylsulfamic, phosphoric and nitric acids.

It will be appreciated that in some instances, compounds of the present invention may include a carboxy group as a substituent. Such carboxy groups may be used to form salts, in particular pharmaceutically acceptable salts. Pharmaceutically acceptable salts include those described by Berge, Bighley, and Monkhouse, *J. Pharm Sci.*, 1977, 66, 1–19. Preferred salts include alkali metal salts such as the sodium and potassium salts.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the term "aryl" refers to, unless otherwise defined, a mono- or bicyclic aromatic ring system containing up to 10 carbon atoms in the ring system, for instance phenyl or naphthyl.

When used herein, the term "heteroaryl" refers to a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When used herein, the terms "halogen" and "halo" include fluorine, chlorine, bromine and iodine and fluoro, chloro, bromo and iodo, respectively.

Particularly preferred compounds of formula (I) are:

1-(N-Methyl-N-(4-(4-chlorophenyl)benzyl)aminocarbonylmethyl)-2-(4-fluorobenzyl)thio-5-(1-methylpyrazol-4-ylmethyl)pyrimidin-4-one;

1-(N-Methyl-N-(4-(4-trifluoromethylphenyl)benzyl)aminocarbonylmethyl)-2-(4-fluorobenzyl)thio-5-(1-methylpyrazol-4-ylmethyl)pyrimidin-4-one;

1-(N-(2-Dimethylaminoethyl)-N-(4-(4-chlorophenyl)benzyl)aminocarbonylmethyl-2-(4-fluorobenzyl)thio-5-(1-methylpyrazol-4-ylmethyl)pyrimidin-4-one;

1-(N-Methyl-N-(4-(4-chlorophenyl)benzyl)aminocarbonylmethyl)-2-(4-fluorobenzyl)thio-5-(2-(4-morpholino)pyrimid-5-ylmethyl)pyrimidin-4-one;

1-(N-(2-(dimethylamino)ethyl)-N-(4-(4-trifluoromethylphenyl)benzyl)aminocarbonylmethyl-2-(4-fluorobenzyl)thio-5-(1-methyl-4-pyrazolylmethyl)pyrimidin-4-one;

1-(N-(2-(diethylamino)ethyl)-N-(4-(4-chlorophenyl)benzyl)aminocarbonylmethyl)-2-4-fluorobenzyl)thio-5-(1-methyl-4-pyrazolylmethyl)pyrimidin-4-one;

1-(N-(2-diethylamino)ethyl)-N-(2-(4-trifluoromethylphenyl)pyrid-5-ylmethyl)aminocarbonylmethyl)-2-(4-fluorobenzyl)thio-5-(1-methyl-4-pyrazolylmethyl)pyrimidin-4-one;

1-(N-(2-(1-Piperidino)ethyl)-N-(4-(4-trifluoromethylphenyl)benzyl)aminocarbonylmethyl)-2-4-fluorobenzyl)thio-5-(1-methyl-4-pyrazolylmethyl)pyrimidin-4-one bitartrate;

1-(N-(Carboxymethyl)-N-(4-4-trifluoromethylphenyl)benzyl)aminocarbonylmethyl)-2-(4-fluorobenzyl)thio-5-(1-methylpyrazolylmethyl)pyrimidin-4-one sodium salt; and 1-(N-(2-(diethylamino)ethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4-one or a pharmaceutically acceptable salt thereof, including the hydrochloride, bitartrate, citrate and tosylate salts.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase $A_2$ (Lp-PLA$_2$) and as such are expected to be of use in therapy, in particular in the treatment of atherosclerosis. In a further aspect therefore the present invention provides a compound of formula (I) for use in therapy.

The compounds of formula (I) are inhibitors of lysophosphatidylcholine production by Lp-PLA$_2$ and may therefore also have a general application in any disorder that involves endothelial dysfunction, for example atherosclerosis, diabetes, hypertension, angina pectoris and after ischaemia and reperfusion. In addition, compounds of formula (I) may have a general application in any disorder that involves lipid oxidation in conjunction with enzyme activity, for example in addition to conditions such as atherosclerosis and diabetes, other conditions such as rheumatoid arthritis, stroke, inflammatory conditions of the brain such as Alzheimer's Disease, myocardial infarction, reperfusion injury, sepsis, and acute and chronic inflammation. Further such conditions include various neuropsychiatric disorders such as schizophrenia (see Psychopharmacology Bulletin, 31, 159–165, 1995).

Further applications include any disorder that involves activated monocytes, macrophages or lymphocytes, as all of these cell types express Lp-PLA$_2$. Examples of such disorders include psoriasis.

Accordingly, in a further aspect, the present invention provides for a method of treating a disease state associated with activity of the enzyme Lp-PLA$_2$ which method involves treating a patient in need thereof with a therapeutically effective amount of an inhibitor of the enzyme. The disease state may be associated with the increased involvement of monocytes, macrophages or lymphocytes; with the formation of lysophosphatidylcholine and oxidised free fatty acids; with lipid oxidation in conjunction with Lp PLA2 activity; or with endothelial dysfunction.

Compounds of the present invention may also be of use in treating the above mentioned disease states in combination with an anti-hyperlipidaemic, anti-atherosclerotic, anti-diabetic, anti-anginal, anti-inflammatory, or anti-hypertension agent or an agent for lowering Lp(a). Examples of the above include cholesterol synthesis inhibitors such as statins, anti-oxidants such as probucol, insulin sensitisers, calcium channel antagonists, and anti-inflammatory drugs such as NSAIDs. Examples of agents for lowering Lp(a) include the aminophosphonates described in WO 97/02037, WO 98/28310, WO 98/28311 and WO 98/28312 (Symphar SA and SmithKline Beecham).

A preferred combination therapy will be the use of a compound of the present invention and a statin. The statins are a well known class of cholesterol lowering agents and include atorvastatin, simvarstatin, pravastatin, cerivastatin, fluvastatin, lovastatin and ZD 4522 (also referred to as S-4522, Astra Zeneca). The two agents may be administered at substantially the same time or at different times, according to the discretion of the physician.

A further preferred combination therapy will be the use of a compound of the present invention and an anti-diabetic agent or an insulin sensitiser, as coronary heart disease is a major cause of death for diabetics. Within this class, preferred compounds for use with a compound of the present invention include the PPARgamma activators, for instance G1262570 (Glaxo Wellcome) and also the glitazone class of compounds such as rosiglitazone (Avandia, SmithKline Beecham), troglitazone and pioglitazone.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier.

Suitable pharmaceutical compositions include those which are adapted for oral or parenteral administration or as a suppository.

Suitable pharmaceutical compositions include those which are adapted for oral or parenteral administration or as a suppository. Compounds of formula (I) which are active when given orally can be formulated as liquids, for example syrups, suspensions or emulsions, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule. Each dosage unit for oral administration contains preferably from 1 to 500 mg (and for parenteral administration contains preferably from 0.1 to 25 mg) of a compound of the formula (I). The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

A compound of formula (I) may be prepared by a number of processes which include:

(a) reacting a compound of formula (II):

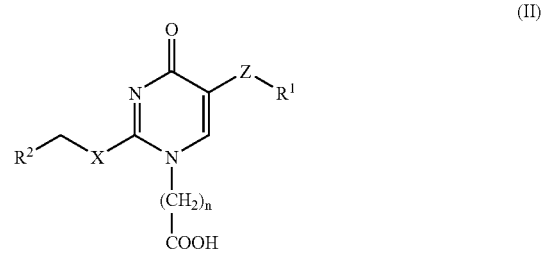

(II)

in which X, Y, Z, R$^1$ and R$^2$ are as hereinbefore defined, with a compound of formula (III):

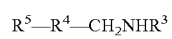

(III)

in which R$^3$, R$^4$ and R$^5$ are as hereinbefore defined; under amide forming conditions;

(b) reacting a compound of formula (IV):

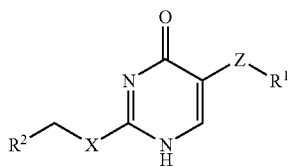
(IV)

in which X, Z, R$^1$ and R$^2$ are as hereinbefore defined, with a compound of formula (V):

$$R^5—R^4—CH_2NR^3—CO—(CH_2)_n-L^1 \quad (V)$$

in which n, R$^3$, R$^4$ and R$^5$ are as hereinbefore defined, and L$^1$ is a leaving group such as halogen, for instance bromo or iodo, in the presence of a base such as a secondary or tertiary amine, for instance di-iso-propylethylamine, in an inert solvent such as dichloromethane;

(c) when X is S, reacting a compound of formula (VI):

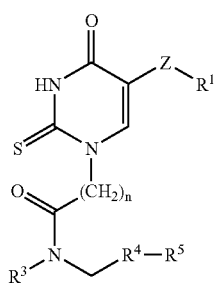
(VI)

in which n, Z, R$^1$, R$^3$, R$^4$ and R$^5$ are as hereinbefore defined, with a compound of formula (VII):

$$R^2—CH_2-L^1 \quad (VII)$$

in which R$^2$ and L$^1$ are as hereinbefore defined, in the presence of a base such as a secondary or tertiary amine, for instance di-isopropylethylamine, in an inert solvent such as dichloromethane; or (d) when X is O, reacting a compound of formula (VIII):

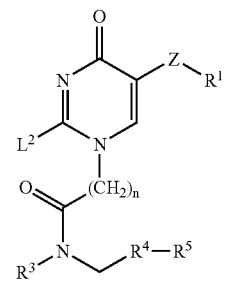
(VIII)

in which n, Z, R$^1$, R$^3$, R$^4$ and R$^5$ are as hereinbefore defined, and L$^2$ is a leaving group such as halogen or alkylthio, for instance methylthio, with a compound of formula (IX):

$$R^2—CH_2—OH \quad (IX)$$

in which R$^2$ is as hereinbefore defined, in the presence of a base such as 4-dimethylaminopyridine, in an inert solvent such as pyridine.

Compounds of formulae (II), (IV), (VI) and (VIII) for use in the above processes may be prepared by processes illustrated in the following scheme I:

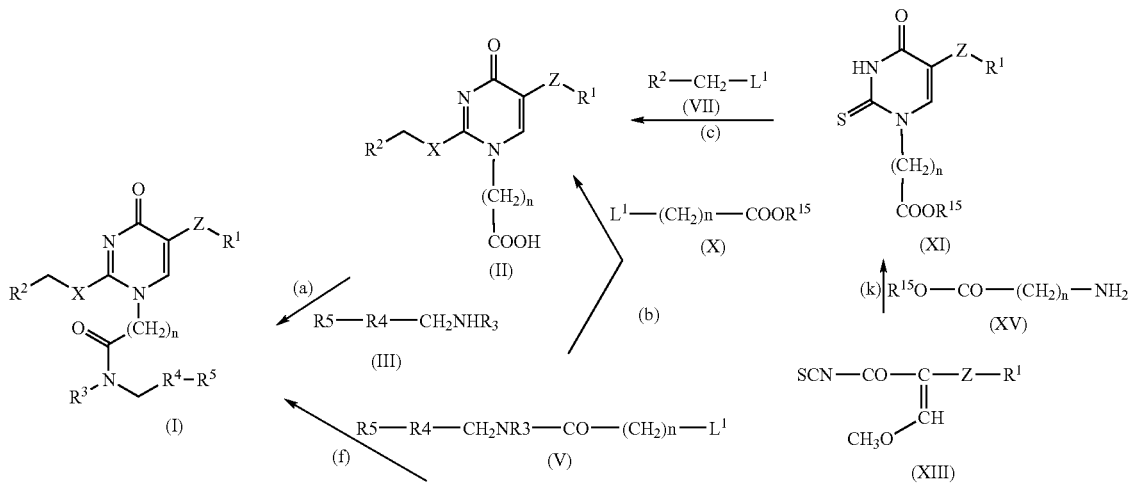

Scheme I

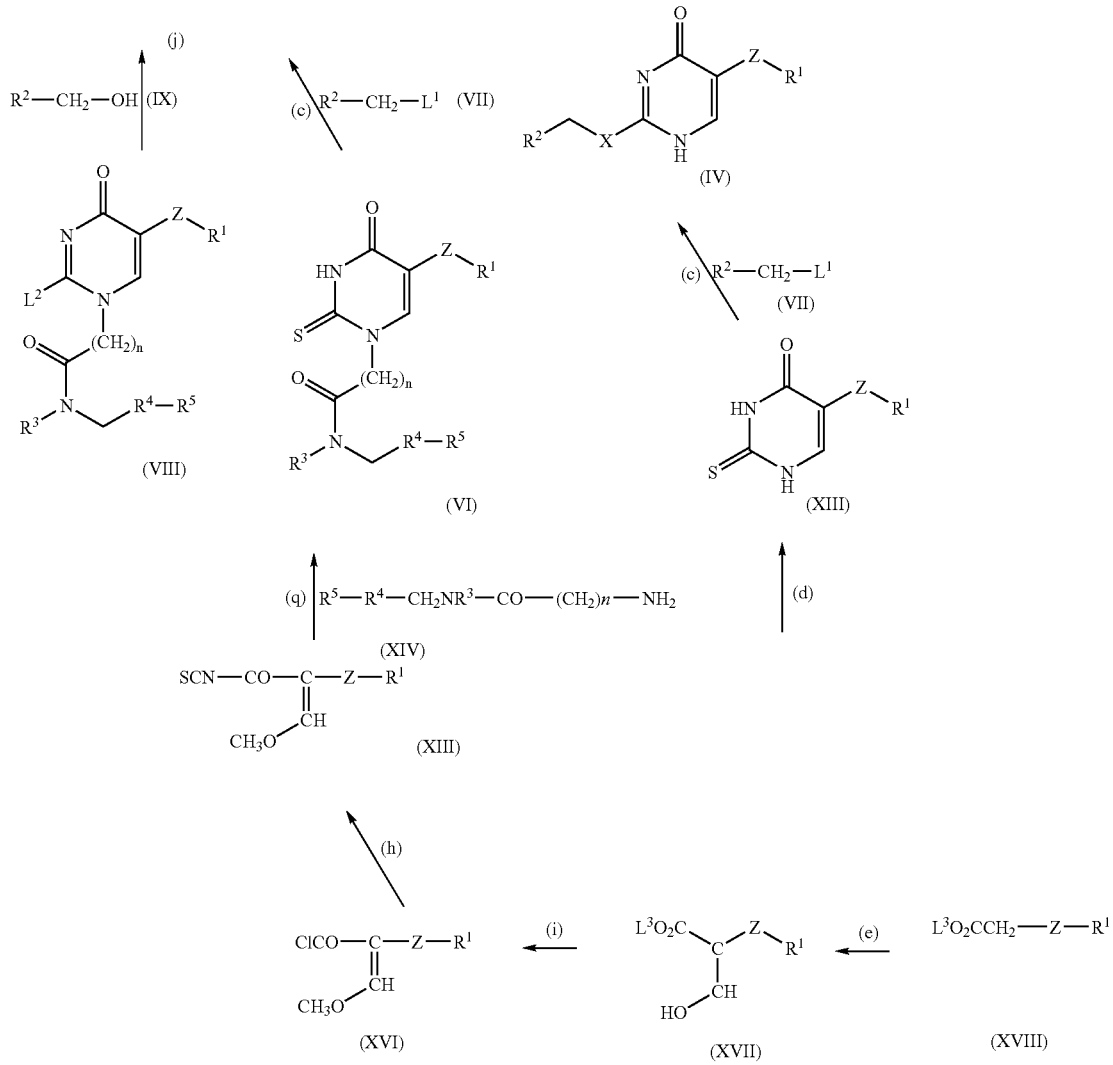

in which:

$L^3$ is a C(1–6)alkyl group, for instance methyl;

$R^{15}$ is a $C_{(1-6)}$alkyl group, for instance methyl, ethyl, or t-butyl, and $L^1$, $L^2$, $R^1$, $R^2$, $R^3$, $R^4$, $R^5$, n, X and Z are as hereinbefore defined.

With reference to Scheme I:

Amide forming conditions for step (a) are well known in the art. Preferably, the acid of formula (II) is reacted with the amine of formula (III) in an inert solvent, such as dichloromethane, at ambient temperature and in the presence of an activating agent such as as 1-(3-dimethylaminopropyl)-3-ethylcarbodiimide plus hydroxybenzotriazole.

Alkylation conditions for step (b) include reaction in the presence of a base such as a secondary or tertiary amine, for instance di-iso-propylethylamine, in an inert solvent such as dichloromethane, forming an intermediate ester which is converted to the acid of formula (II) by hydrolysis, for instance using aqueous sodium hydroxide in a solvent such as dioxan or by alternative deprotection, for instance using trifluoracetic acid in a solvent such as dichloromethane.

Conditions for step (c) include under thioether forming conditions. Advantageously, the reaction is carried out in the presence of a base such as sodium ethoxide or potassium carbonate, preferably in a solvent such as ethanol or dimethyl formamide, or a secondary or tertiary amine base such as di-isopropylethyl amine, in solvent such as dichloromethane.

In step (d), a compound of formula (XVII) is reacted with thiourea, in the presence of sodium ethoxide (preferably generated in situ from sodium and ethanol).

In step (e), a compound of formula (XVIII) is reacted with ethyl formate in the presence of a base such as sodium hydride or potassium isopropoxide.

In step (f), a compound of formula (IV) is reacted with a compound of formula (V) in the presence of a base such as a secondary or tertiary amine, for instance di-isopropylethylamine, in an inert solvent such as dichloromethane In step (g), a compound of formula (XIII) is reacted with a compound of formula (XIV) in a solvent such as dimethylformamide to form an intermediate thiourea, which is then treated with a base such as sodium methoxide.

In step (h), a compound of formula (XVI) is reacted with a metal thiocyanate, for example potassium thiocyanate, in a solvent such as acetonitrile.

In step (i), a compound of formula (XVII) is reacted with a methylating agent such as dimethyl sulphate in the presence of a base such as potassium carbonate, followed by hydrolysis of the intermediate ester in conventional manner e.g. by basic hydrolysis using sodium hydroxide to give the corresponding carboxylic acid which may then be converted into the acyl chloride, for instance by treatment with oxalyl chloride.

In step (j), a catalyst such as 4-dimethylaminopyridine, and in a solvent such as pyridine are used.

In step (k), a compound of formula (XIII) is reacted with a compound of formula (XV) in a solvent such as dimethylformamide to form an intermediate thiourea, which is then treated with a base such as sodium methoxide.

The present invention will now be illustrated by the following examples.

EXAMPLES

The structure and purity of the intermediates and examples was confirmed by 1H-NMR and (in nearly all cases) mass spectroscopy, even where not explicitly indicated below.

Intermediate A1—4-(4-Chorophenyl)benzaldehyde

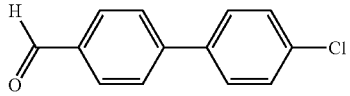

(a) A mixture of 4-formylbenzeneboronic acid (2.50 g, 2 equiv), 4-chloroiodobenzene (1.98 g, 1 equiv), tetrakis (triphenylphosphine)palladium(0) (0.50 g, 0.05 equiv), aqueous sodium carbonate (18 ml, 2M solution, 2 equiv) and dimethoxyethane (50 ml) was stirred at reflux under argon overnight, then cooled and diluted with ethyl acetate. The mixture was filtered as necessary to remove inorganic residues, then the organic layer was washed successively with aqueous citric acid and brine, dried and evaporated. The crude product was purified by chromatography (silica, 5% ethyl acetate in hexane); product fractions were evaporated to a white solid (1.32 g, 72%).
(b) A mixture of 4-chlorobenzeneboronic acid (19.4 g, 1 equiv), 4-bromobenzaldehyde (22.9 g, 1 equiv), palladium(II) acetate (1.4 g, 0.05 equiv) aqueous sodium carbonate (30.3 g in 144 ml solution, 2 equiv) and dimethoxyethane (500 ml) was stirred at reflux under argon for 2.5 h, then evaporated to low volume and diluted with dichloromethane. Workup continued as in (a) above to give identical material (25.2 g, 94%). $^1$H-NMR (CDCl$_3$) δ 10.05 (1H, s), 7.96 (2H, d), 7.73 (2H, d), 7.57 (2H, d), 7.46 (2H, d); MS (AP+) found (M+1)=217, C$_{13}$H$_9$$^{35}$ClO requires 216.

Intermediate A2—N-Methyl-4-(4-chlorophenyl)benzylamine

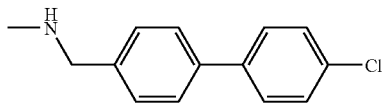

A mixture of Intermediate A1 (3.5 g, 1 equiv), methylamine (32.3 ml of a 2M solution in THF, 4 equiv) and anhydrous magnesium sulphate (4.47 g, 2 equiv) was stirred at room teperature for 16 h, then filtered, the solid washed thoroughly with ethyl acetate, and the combined filtrates evaporated to a white solid (3.7 g). This imine intermediate was suspended in ethanol (100 ml), cooled in ice and sodium borohydride (0.61 g, 1 equiv) added portionwise. The ice bath was removed, and the mixture stirred for 45 min at room temperature then at 50° C. for 1 h. The solvent was removed in vacuo, water was added to the residue, and the product extracted into dichloromethane. Drying and evaporation of the solvent gave a white solid (3.56 g). $^1$H-NMR (CDCl$_3$) δ 7.51 (4H, d), 7.40 (4H, d), 3.79 (2H, s), 2.48 (3H, s); MS (APCI+) found (M+1)=232, C$_{14}$H$_{14}$$^{35}$ClN requires 231.

Intermediate A3—N-(2-Diethylaminoethyl)-4-(4-chlorophenyl)benzylamine

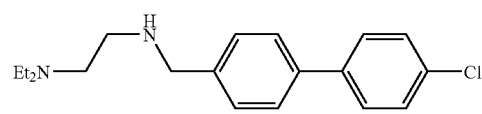

A mixture of Intermediate A1 (55.0 g), N,N-diethylethylenediamine (35.6 ml), 4A molecular sieve (37 g), and dichloromethane (1100 ml) was reacted at room temperature under argon for 16 h, with occasional agitation. The solid was filtered off and washed with dichloromethane, and the combined filtrates evaporated to a yellow foam (72.4 g). This intermediate imine was reduced with sodium borohydride (8.7 g) in ethanol (850 ml) as described for Intermediate A2, yielding the title compound as a yellow oil (72.7 g). $^1$H-NMR (CDCl$_3$) δ 1.70 (2H, t), 2.22 (6H, s), 2.33 (2H, t), 2.69 (2H, br, m), 3.83 (2H, s), 7.37–7.43 (4H, m), 7.52–7.56 (4H, m).

Intermediate A4—4-(4-Chlorophenyl)benzyl alcohol

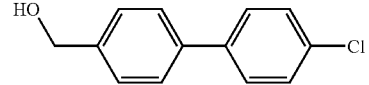

A mixture of Intermediate A1 (1.73 g, 1 equiv), sodium borohydride (0.3 g, 1 equiv) and ethanol (20 ml) was stirred until a clear solution was obtained; a gentle exotherm was observed. The temperature was raised to 50° C. and stirring continued for 2 h, then the solvent was removed in vacuo, water added to the residue, and the product extracted into dichloromethane. Drying and evaporation of the solvent gave a white solid (1.67 g). $^1$H-NMR (CDCl$_3$) δ 1.73 (1H,t), 4.74 (2H, d), 7.2–7.6 (8H, m),.

Intermediate A5—N-(4-(4-Chlorophenyl)benzyl)phthalimide

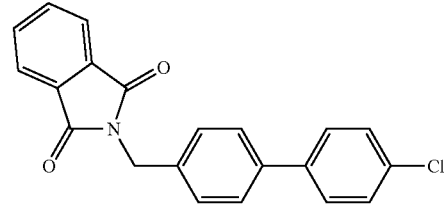

Intermediate A4 (1.62 g, 1 equiv), phthalimide (1.42 g, 1.3 equiv) and triphenylphosphine (2.53 g, 1.3 equiv) were dissolved in dry THF (50 ml), the solution was cooled in ice, and diethyl azodicarboxylate (1.52 ml, 1.3 equiv) was added slowly with stirring. The yellow solution was stirred for 16 h at room temperature, then the solvent was evaporated. Chromatography (silica, 1:1 dichloromethane/pet. ether) and trituration with ether gave the desired product (2.03 g, 79%). $^1$H-NMR (CDCl$_3$) δ 4.89 (2H, s), 7.36–7.50 (8H, m), 7.69–7.74 (2H, m), 7.82–7.89 (2H, m).

Intermediate A6—4-(4-Chlorophenyl)benzylamine

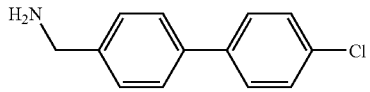

A mixture of Intermediate A5 (1.98 g, 1 equiv) and hydrazine hydrate (0.55 ml, 2 equiv) in ethanol (40 ml) was heated at reflux for 2 h, then the solvent was evaporated. The residue was shaken with dichloromethane and 0.5M aqueous sodium hydroxide, the aqueous layer re-extracted with dichloromethane, and the combined organic extracts purified by chromatography (silica, 1–3% methanolic ammonia in dichloromethane). Product fractions were evaporated to a white solid (0.53 g, 43%). $^1$H-NMR (CDCl$_3$) δ 3.92 (2H, s), 7.28–7.41 (4H, m), 7.49–7.54 (4H, m).

Intermediate A7—N-Methyl-N-(4-(4-chlorophenyl)benzyl) bromoacetamide

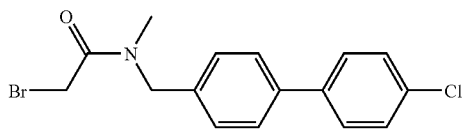

Bromoacetyl bromide (0.123 ml, 1.1 equiv) was added to a well-stirred mixture of Intermediate A2 (0.3 g, 1 equiv), sodium hydroxide (0.06 g, 1.2 equiv), water and dichloromethane. Stirring was continued for 3 h at room temperature, then the phases were separated and the organic layer dried and evaporated. Chromatography (silica, 3:1 hexane/ethyl acetate) gave the desired product as an oil (0.37 g). $^1$H-NMR (CDCl$_3$) δ 7.38–7.68 (8H, m), 4.77 (2H, s), 4.07 (2H, s), 3.24 (3H, s); MS (APCI+) found (M+1)=352, $C_{16}H_{15}^{79}Br^{35}ClNO$ requires 351.

Intermediate A8—5-Hydroxymethyl-2-(4-fluorophenyl)pyridine

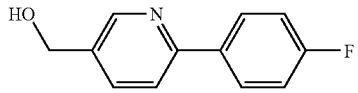

A solution of Intermediate A23 (4.63 g) in dry dichloromethane (100 ml) was cooled to −78° C. under argon, then DIBAL-H (26.7 ml, 1.5M solution in toluene) was added dropwise over 20 min. Stirring was continued for 40 min at −78° C., then 2M hydrochloric acid (52 ml) was added dropwise over 15 min. The solution was allowed to warm slowly to room temperature, then the organic layer was separated, washed with water, dried and evaporated. Chromatography (silica, 1:1 ethyl acetate/hexane) gave the product as a white solid (3.03 g, 75%). $^1$H-NMR (CDCl$_3$) δ (1H, d), 7.98 (2H, m), 7.77 (1H, m), 7.68 (1H, d), 7.15 (2H, t), 4.77 (2H, d), 1.802 (1H, t); MS(APCI+) found (M+1)=204, $C_{12}H_{10}FNO$ requires 203.

Intermediate A9—5-Formyl-2-(4fluorophenyl)pyridine

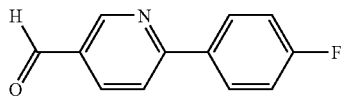

Activated manganese dioxide (3.19 g) was added to a solution of Intermediate A8 (0.75 g) in dichloromethane (50 ml) and stirred at room temperature for 16 h. The solids were filtered off and the filtrate evaporated to a pale yellow solid (0.57 g). $^1$H-NMR (CDCl$_3$) δ 10.15 (1H, s), 9.11 (1H, s), 8.22 (1H, dd), 8.10 (2H, m), 7.87 (1H, d), 7.20 (2H, t); MS(APCI+) found (M+1)=202, $C_{12}H_8FNO$ requires 201.

Intermediate A10—N-Methyl-4-(4-chlorophenyl)-3-fluorobenzylamine

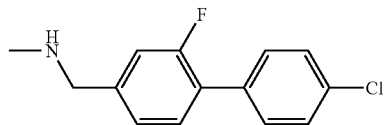

Borane (1M solution in THF, 2 equiv) was stirred under argon with ice cooling, and a suspension of Intermediate A39 (1 equiv) in dry THF was added gradually over a few minutes. After 5 mins the ice bath was removed and the mixture heated to reflux for 1 h, then cooled to room temperature. 5M Hydrochloric acid was added dropwise, and the THF was removed from the resulting suspension by distillation. The residue was diluted with water and made strongly basic with sodium hydroxide, then the product was extracted into ether. Drying and evaporation of the organic solution, followed by chromatography gave the title compound as an oil (88%). $^1$H-NMR (CDCl$_3$) δ 2.48 (3H, s), 3.79(2H, s), 7.12–7.18 (2H, m), 7.33–7.50 (5H, m); MS (APCI+) found (M+1)=250; $C_{14}H_{13}ClFN$ requires 249.

Intermediate A11—N-(Ethoxycarbonylmethyl)-4-(4-chlorophenyl)benzylamine

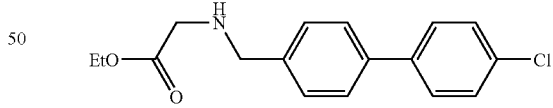

A mixture of Intermediate A1 (0.5 g, 1 equiv), glycine ethyl ester hydrochloride (0.32 g, 1 equiv), diisopropylethylamine (0.4 ml, 1 equiv) and 1,2-dichloroethane (10 ml) was stirred at room temperature, sodium triacetoxyborohydride (0.73 g, 1.5 equiv) was added, and stirring continued overnight. After diluting with dichloromethane, the solution was washed with water and dried over potassium carbonate. Evaporation of the solvent yielded the title compound (0.57 g) as a white waxy solid. $^1$H-NMR (CDCl$_3$) δ 1.22–1.37 (3H, t), 3.44 (2H, s), 3.85 (2H, s), 4.15–4.32 (2H, q), 7.35–7.62 (8H, m); ); MS (APCI+) found (M+1)=304; $C_{17}H_{18}ClNO_2$ requires 303.

Intermediate A12—2-Hydroxymethyl-5-(4-chlorophenyl)pyridine

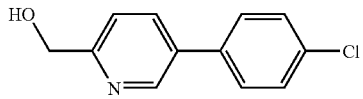

m-Chloroperbenzoic acid (0.93 g) was added portionwise over 30 min to a solution of Intermediate A41 (0.77 g) in dichloromethane (10 ml), then the mixture was stirred at room temperature for a further hour, diluted with dichloromethane, washed with aq. sodium bicarbonate, dried and evaporated. Chromatography (silica, 5% methanol in dichloromethane) gave 2-methyl-5-(4-chlorophenyl)pyridine-N-oxide (0.79 g) as a white solid. This material was dissolved in dichloromethane (15 ml), trifluoroacetic anhydride (1.9 ml) added, and the mixture stirred for 1 hour at room temperature followed by 1 hour at reflux. Volatile components were removed in vacuo, then the residue was redissolved in dichloromethane (5 ml), 2M aq. sodium carbonate (14 ml) was added, and stirred vigorously for 2 hours. The mixture was diluted with dichloromethane and water, and the organic layer was washed with water, dried and evaporated. Chromatography (silica, 5% methanol in dichloromethane) gave the title compound (0.67 g) as an off-white solid. $^1$H-NMR (CDCl$_3$) δ 3.61 (1H,t), 4.82 (2H,d), 7.33 (1H,d), 7.45 (2H,m), 7.51 (2H,m), 7.85 (1H,dd), 7.78 (1H, d); MS (APCI+) found (M+1)=220/222; C$_{12}$H$_{10}$ClNO requires 219/221.

Intermediate A13—Ethyl 2-(4-chlorophenyl)-4-oxopyrimidine-5-carboxylate

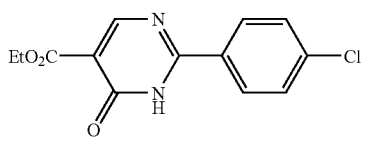

Sodium ethoxide (11.12 ml, 2 equiv) as a 21% w/v solution in ethanol was added dropwise to a suspension of diethyl ethoxymalonate (3.03 ml, 1 equiv) and 4-chlorobenzamidine hydrochloride (4.23 g, 1 equiv) in ethanol (30 ml), then the mixture was heated to reflux for 4 hours. After cooling, the solvent was removed in vacuo and the residue was triturated with ether. The solid was filtered off, then resuspended in water and acidified to pH 2. The product was filtered off, washed with water and dried; yield 2.94 g. $^1$H-NMR (d$_6$-DMSO) δ 1.29 (3H,t), 4.26 (2H,q), 7.65 (2H, m), 8.18 (2H,m), 8.65 (1H,s); MS (APCI−) found (M−1) =277/279; C$_{13}$H$_{11}$ClN$_2$O$_3$ requires 278/280.

Intermediate A14—Ethyl 2-(4-chlorophenyl)-4-chloropyrimidine-5-carboxylate

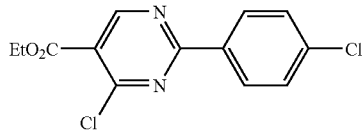

Oxalyl chloride (0.31 ml, 2 equiv) was added to Intermediate A13 (0.49 g) in dichloromethane (20 ml) with ice cooling, then the mixture was stirred for 3 hours with warming to room temperature. Evaporation of the volatile components gave the product as a white solid (2.94 g). $^1$H-NMR (CDCl$_3$) δ 1.44 (3H,t), 4.48 (2H,q), 7.50 (2H,m), 8.45 (2H,m), 9.17 (1H,s); MS (APCI+) found (M+1)=297; C$_{13}$H$_{10}$Cl$_2$N$_2$O$_2$ requires 296.

Intermediate A15—Ethyl 2-(4-chlorophenyl)pyrimidine-5-carboxylate

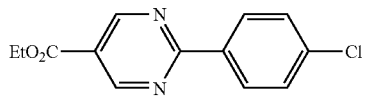

A mixture of Intermediate A14 (6.8 g, 1 equiv), zinc powder (1.79 g, 1.2 equiv), acetic acid (1.57 ml, 1.2 equiv) and THF (100 ml) was stirred at 60° C. under argon for 18 hours, then a further portion of acetic acid (1 ml) and zinc (1.0 g) was added, and the reaction allowed to continue for a further 24 hours. The solvent was removed in vacuo, the residue was taken up in a mixture of dichloromethane and methanol, and undissolved zinc powder was removed by filtration. After evaporation of the solvent, the product crystallised from ethanol; yield 2.02 g. $^1$H-NMR (CDCl$_3$) δ 1.44 (3H,t), 4.46 (2H,q), 7.48 (2H,m), 8.48 (2H,m), 9.30 (2H,s); MS (APCI+) found (M+1)=263; C$_{13}$H$_{11}$ClN$_2$O$_2$ requires 262.

Intermediate A16—5-Hydroxymethyl-2-(4-trifluoromethylphenyl)pyrimidine

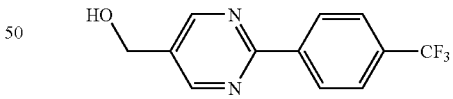

Intermediate A129 (0.96 g) was hydrogenated over 10% palladium on charcoal (96 mg) in a mixture of triethylamine (2 ml) and ethanol (20 ml) for 90 mins at 1 atmosphere pressure. The catalyst was removed by filtration, the solvent was evaporated, and the residue was taken up in ethyl acetate and washed successively with aq. ammonium chloride and aq. sodium bicarbonate. Drying and evaporation gave the title compound (2.02 g). $^1$H-NMR (CDCl$_3$) δ 4.82 (2H,s), 7.75 (2H,m), 8.57 (2H,m), 8.85 (2H,s); MS (APCI+) found (M+1)=255; C$_{11}$H$_9$ClN$_2$O requires 254.

The following intermediates were made by the method of Intermediate A1:

| No. | Precursors | Structure | Name |
|---|---|---|---|
| A20 | 4-formylboronic acid, 4-fluoroiodobenzene | 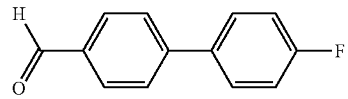 | 4-(4-Fluorophenyl)benzaldehyde |
| A21 | 2-bromothiophene-5-carboxaldehyde, 4-fluorobenzeneboronic acid | 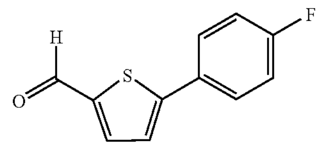 | 5-(4-Fluorophenyl)-2-thiophene carboxaldehyde |
| A22 | 2-bromothiophene-5-carboxaldehyde, 4-chlorobenzeneboronic acid | 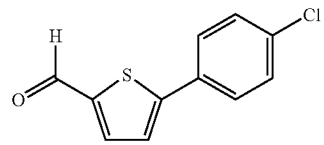 | 5-(4-Chlorophenyl)-2-thiophene carboxaldehyde |
| A23 | methyl 6-chloronicotinate, 4-fluorobenzeneboronic acid | 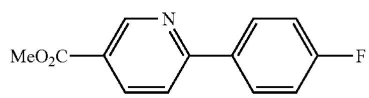 | Methyl 6-(4-fluorophenyl)-nicotinate |
| A24 | methyl 6-chloronicotinate, 4-chlorobenzeneboronic acid | 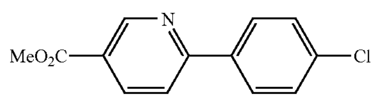 | Methyl-6-(3,4-dichlorophenyl)-nicotinate |
| A25 | methyl 6-chloronicotinate, 3,4-dichlorobenzeneboronic acid | 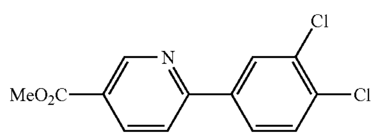 | Methyl-6-(3,4-dichlorophenyl)-nicotinate |
| A26 | 4-bromobenzaldehyde, 4-trifluoromethylbenzene-boronic acid | 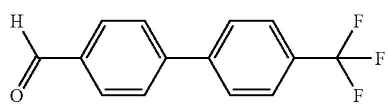 | 4-(4-Trifluoromethylphenyl)-benzaldehyde |
| A27 | 4-bromo-2-fluorobenzaldehyde, 4-chlorobenzeneboronic acid | 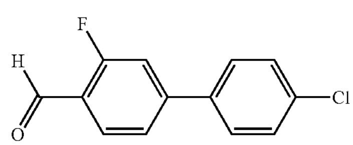 | 4-(4-Chlorophenyl)-2-fluoro-benzaldehyde |
| A28 | 4-formylbenzeneboronic acid, 4-chloro-2-fluoroiodobenzene | 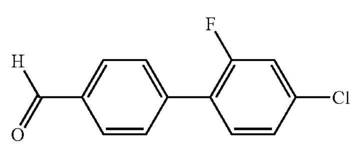 | 4-(4-Chloro-2-fluorophenyl)-benzaldehyde |
| A29 | 4-formylbenzeneboronic acid, 4-chloro-3-fluoroiodobenzene | 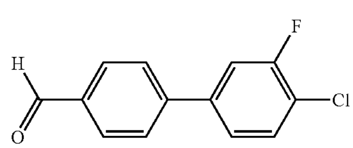 | 4-Chloro-3-fluorophenyl)-benzaldehyde |
| A30 | 4-methoxybenzeneboronic acid, 4-bromobenzaldehyde | 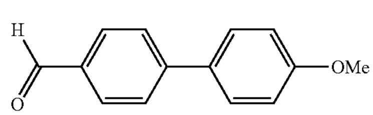 | 4-(4-Methoxyphenyl)-benzylaldehyde |

| No. | Precursors | Structure | Name |
|-----|-----------|-----------|------|
| A31 | 4-formylbenzeneboronic acid, 4-chloro-2-fluoroiodobenzene | 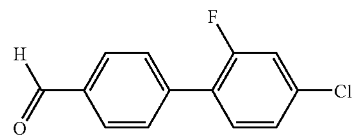 | 4-(2-Fluoro-4-chlorophenyl)-benzaldehyde |
| A32 | 4-formylbenzeneboronic acid, 2,4-bis(trifluoromethyl)-bromobenzene | 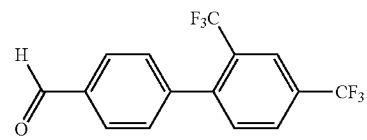 | 4-(2,4-bis(trifluoromethyl)-phenyl)benzaldehyde |
| A33 | 4-formylbenzeneboronic acid, 4-bromo-3-fluorobenzo-trifluoride | 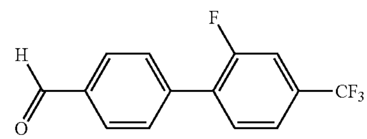 | 4-(2-Fluoro-4-trifluoromethyl-phenyl)benzaldehyde |
| A34 | 4-bromo-2-fluorobenzaldehyde, 4-trifluoromethylbenzene-boronic acid | 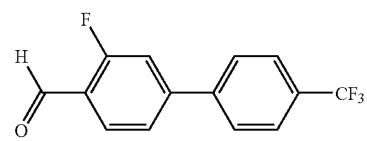 | 2-Fluoro-4-(4-trifluoromethyl-phenyl)benzaldehyde |
| A35 | 3-chloro-4-fluorobenzene-boronic acid, 4-bromobenzaldehyde | 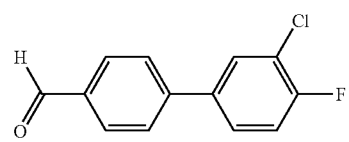 | 3-Chloro-4-fluorophenyl)-benzaldehyde |
| A36 | 4-formylbenzeneboronic acid, 2,4-difluoroiodobenzene | 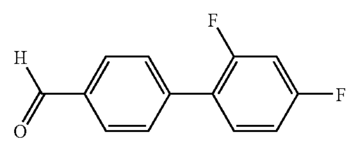 | 4-(2,4-Difluorophenyl)-benzaldehyde |
| A37 | 4-formylbenzeneboronic acid, 4-trifluoromethoxyiodobenzene | 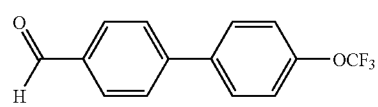 | 4-(4-Trifluoromethoxyphenyl)-benzaldehyde |
| A38 | 4-formylbenzeneboronic acid, 4-difluoromethoxyiodobenzene | 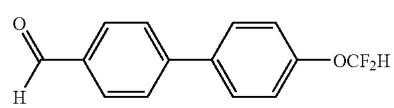 | 4-(4-Difluoromethoxyphenyl)-benzaldehyde |
| A39 | N-methyl-4-bromo-3-fluorobenzamide, 4-chlorobenzeneboronic acid | 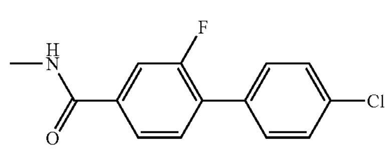 | N-Methyl-4-(4-chlorophenyl)-3-fluorobenzamide |
| A40 | methyl 6-chloronicotinate, 4-trifluoromethylbenzeneboronic acid | 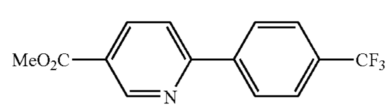 | Methyl 6-(4-trifluoromethyl-phenyl)nicotinate |
| A41 | 2-methyl-5-bromopyridine, 4-chlorobenzeneboronic acid | 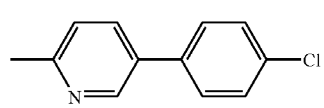 | 2-methyl-5-(4-trifluoromethyl-phenyl)pyridine |
| A42 | 2-methyl-5-triflylpyridine, 4-trifluoromethylbenzeneboronic acid | 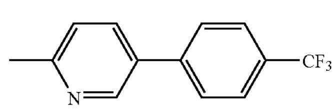 | 2-methyl-5-(4-trifluoromethyl-phenyl)pyridine |

| No. | Precursors | Structure | Name |
|---|---|---|---|
| A43 | 2-methyl-5-triflylpyridine, 4-trifluoromethoxybenzene-boronic acid | 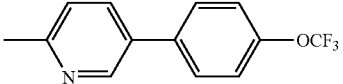 | 2-methyl-5-(4-trifluoromethoxy-phenyl)pyridine |

The following intermediates were made by the method of Intermediate A2, using an appropriate amine in place of methylamine as necessary:

| No. | Precursor | Structure | Name |
|---|---|---|---|
| A44 | Int. A20 | 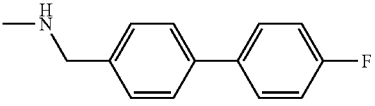 | N-Methyl-4-(4-fluorophenyl)benzylamine |
| A45 | Int. A26 | 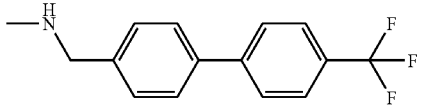 | N-Methyl-4-(4-trifluoromethylphenyl)-benzylamine |
| A46 | Int. A27 | 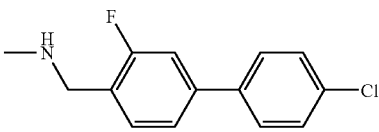 | N-Methyl-4-(4-chlorophenyl)-2-fluoro-benzylamine |
| A47 | Int. A28 | 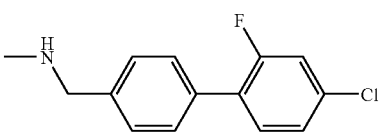 | N-Methyl-4-(4-chloro-2-fluorophenyl)-benzylamine |
| A48 | Int. A1 | 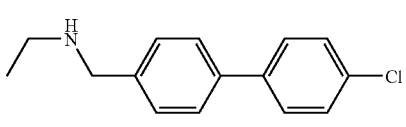 | N-Ethyl-4-(4-chlorophenyl)benzylamine |
| A49 | Int. A131 | 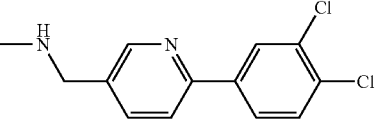 | 5-Methylaminomethyl-2-(3,4-dichlorophenyl)-pyridine |
| A50 | Int. A1 | 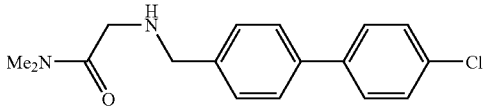 | N-(Dimethylaminocarbonylmethyl)-4-(4-chlorophenyl)benzylamine |
| A51 | Int. A1 | 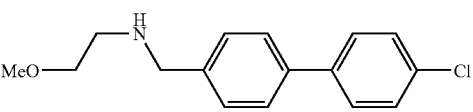 | N-(2-Methoxyethyl)-4-(4-chlorophenyl)-benzylamine |
| A52 | Int. A26 | 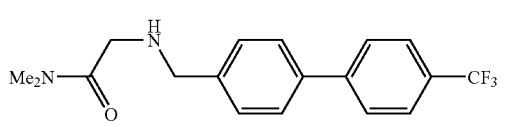 | N-(Dimethylaminocarbonylmethyl)-4-(4-trifluoromethylphenyl)benzylamine |

-continued

| No. | Precursor | Structure | Name |
|---|---|---|---|
| A53 | Int. A29 | 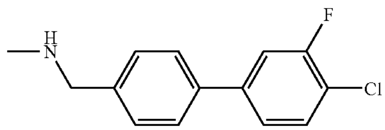 | N-Methyl-4-(4-chloro-3-fluorophenyl)-benzylamine |
| A54 | Int. 30 | 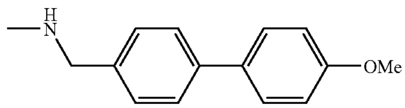 | N-Methyl-4-(4-methoxyphenyl)benzylamine |
| A55 | Int. A31 | 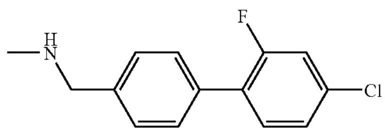 | N-Methyl-4-(2-fluoro-4-chlorophenyl)-benzylamine |
| A56 | Int. A32 | 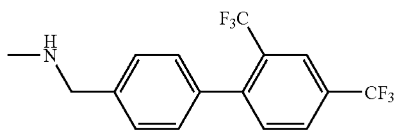 | N-Methyl-4-(2,4-bis(trifluoromethyl)phenyl)-benzylamine |
| A57 | Int. A33 | 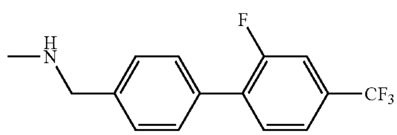 | N-Methyl-4-(2-fluoro-4-trifluorormethylphenyl)-benzylamine |
| A58 | Int. A34 | 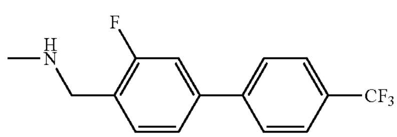 | N-Methyl-2-fluoro-4-(4-trifluoromethyl-phenyl)benzylamine |
| A59 | Int. A35 | 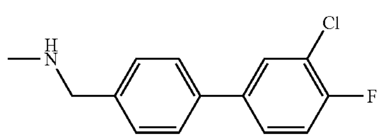 | N-Methyl-4-(3-chloro-4-fluorophenyl)-benzylamine |
| A60 | Int. A36 | 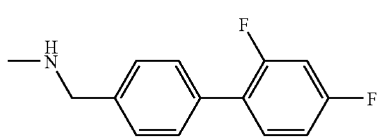 | N-Methyl-4-(2,4-difluorophenyl)benzylamine |
| A61 | Int. A1 | 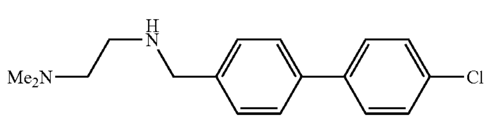 | N-(2-Dimethylaminoethyl)-4-(4-chlorophenyl)-benzylamine |
| A62 | Int. A1 | 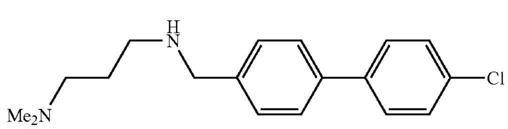 | N-(3-Dimethylaminopropyl)-4-(4-chlorophenyl)-benzylamine |
| A63 | Int. A21 | 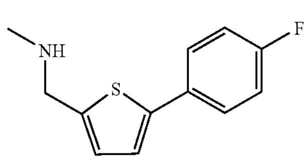 | 2-Methylaminomethyl-5-(4-fluorophenyl)-thiophene |

| No. | Precursor | Structure | Name |
|---|---|---|---|
| A64 | Int. A9 | 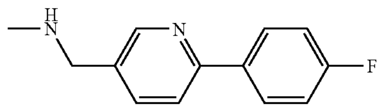 | 5-Methylaminomethyl-2-(4-fluorophenyl)-pyridine |
| A65 | Int. A130 | 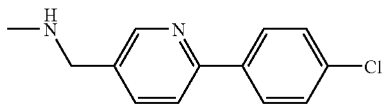 | 5-Methylaminomethyl-2-(4-chlorophenyl)-pyridine |
| A66 | Int. A22 | 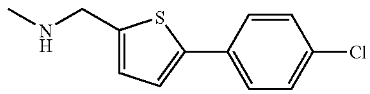 | 2-Methylaminomethyl-5-(4-chlorophenyl)-thiophene |

A67: N-Methyl-4-phenylbenzylamine was made from commercially available 4-biphenylcarboxaldehyde.

The following intermediates were made by the method of Intermediate A3:

| No. | Precursor | Structure | Name |
|---|---|---|---|
| A70 | Int. A1 | 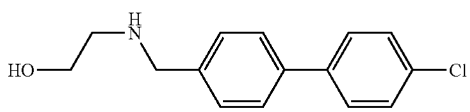 | N-(2-Hydroxyethyl)-4-(4-chlorophenyl)-benzylamine |
| A71 | Int. A26 | 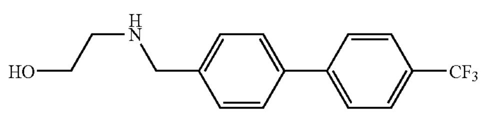 | N-(2-Hydroxyethyl)-4-(4-trifluoromethylphenyl)benzylamine |
| A72 | Int. A26 | 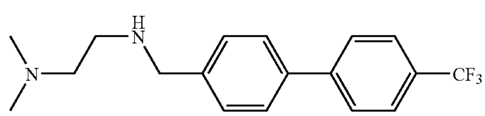 | N-(2-(dimethylamino)ethyl)-4-(4-trifluoromethylphenyl)benzylamine |
| A73 | Int. A26 | 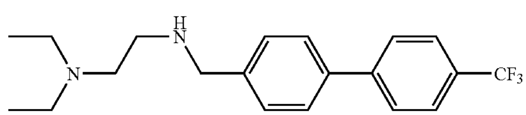 | N-(2-(diethylamino)ethyl)-4-(4-trifluoromethylphenyl)benzylamine |
| A74 | Int. A1 | 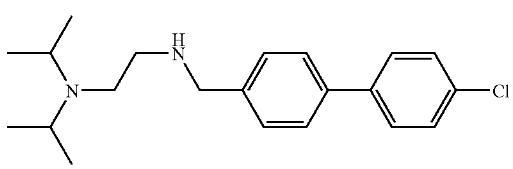 | N-(2-(diisopropylamino)ethyl)-4-(4-chlorophenyl)benzylamine |
| A75 | Int. A1 | 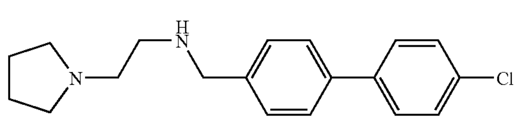 | N-(2-(1-pyrrolidino)ethyl)-4-(4-chlorophenyl)benzylamine |
| A76 | Int. A1 | 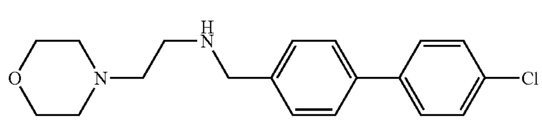 | N-(2-(4-morpholino)ethyl)-4-(4-chlorophenyl)benzylamine |
| A77 | Int. A1 | 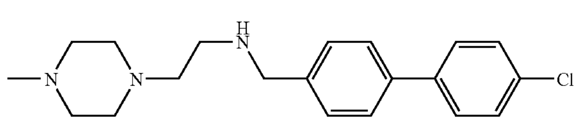 | N-(2-(4-methyl-1-piperazino)ethyl)-4-(4-chlorophenyl)benzylamine |

| No. | Precursor | Structure | Name |
|---|---|---|---|
| A78 | Int. A26 | 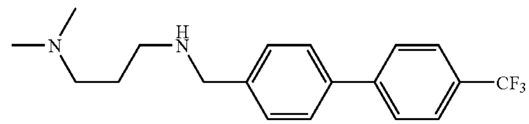 | N-(3-(dimethylamino)propyl)-4-(4-trifluoromethylphenyl)benzylamine |
| A79 | Int. A1 | 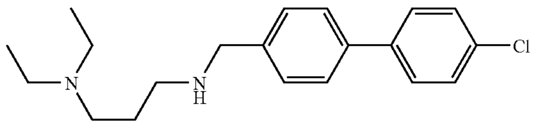 | N-(3-diethylamino)propyl)-4-(4-chlorophenyl)benzylamine |
| A80 | Int. A1 | 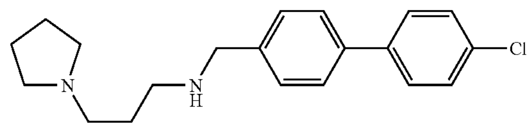 | N-(3-(1-pyrrolidino)propyl)-4-(4-chlorophenyl)benzylamine |
| A81 | Int. A1 | 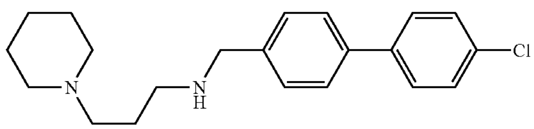 | N-(3-(1-piperidino)propyl)-4-(4-chlorophenyl)benzylamine |
| A82 | Int. A1 | 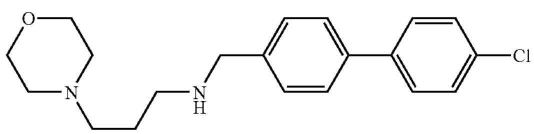 | N-(3-(4-morpholino)propyl)-4-(4-chlorophenyl)benzylamine |
| A83 | Int. A1 | 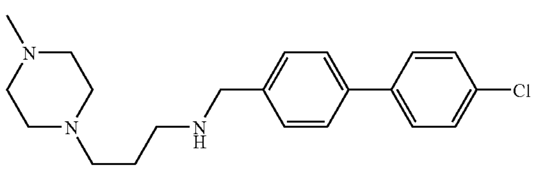 | N-(3-(4-methyl-1-piperazino)propyl)-4-(4-chlorophenyl)benzylamine |
| A84 | Int. A1 | 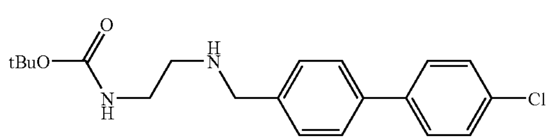 | N-(2-(t-butoxycarbonylamino)ethyl)-4-(4-chlorophenyl)benzylamine |
| A85 | Int. A1 | 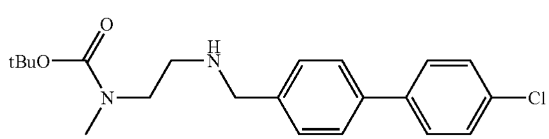 | N-(N'-(2-(t-butoxycarbonyl)-N'-methylamino)ethyl)-4-(4-chlorophenyl)-benzylamine |
| A86 | Int. A1 | 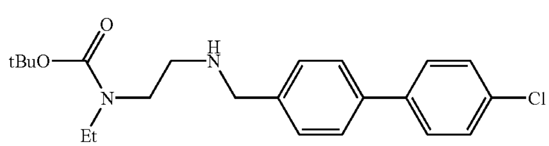 | N-(N'-(2-(t-butoxycarbonyl)-N'-ethylamino)ethyl)-4-(4-chlorophenyl)-benzylamine |
| A87 | Int. A26 | 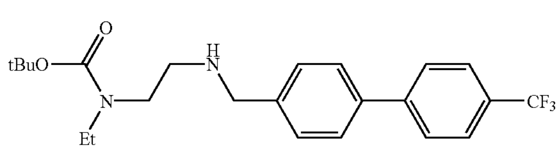 | N-(N'-(2-(t-butoxycarbonyl)-N'-ethylamino)ethyl)-4-(4-trifluoromethylphenyl)benzylamine |

-continued

| No. | Precursor | Structure | Name |
|---|---|---|---|
| A88 | Int. A1 | 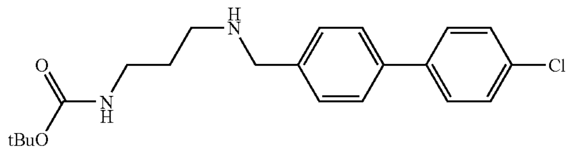 | N-(3-(t-butoxycarbonylamino)propyl)-4-(4-chlorophenyl)benzylamine |
| A89 | Int. A1 | 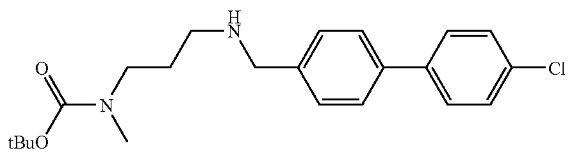 | N-(N'-(3-(t-butoxycarbonyl)-N'-methyl-amino)propyl)-4-(4-trifluoromethyl-phenyl)benzylamine |
| A90 | Int. A1 | 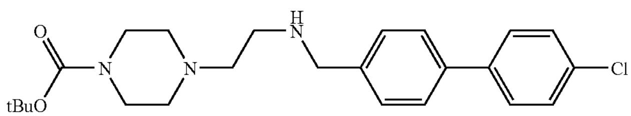 | N-(2-(4-t-butoxycarbonyl-1-piperazino)-ethyl)-4-(4-chlorophenyl)benzylamine |
| A91 | Int. A1 | 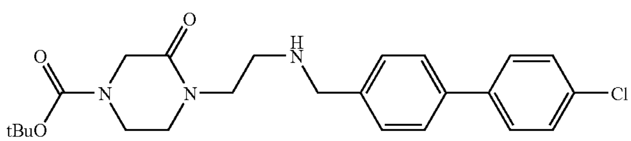 | N-(2-(2-oxo-4-t-butoxycarbonyl-1-piperazino)ethyl)-4-(4-chlorophenyl)-benzylamine |
| A92 | Int. A37 | 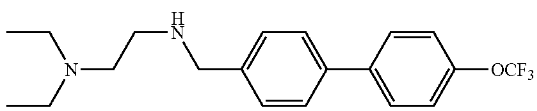 | N-(2-diethylamino)ethyl)-4-(4-trifluoro-methoxyphenyl)benzylamine |
| A93 | Int. A38 | 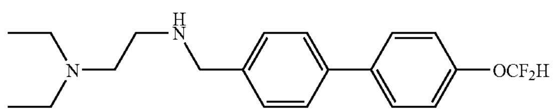 | N-(2-(diethylamino)ethyl)-4-(4-difluoro-methoxyphenyl)benzylamine |
| A94 | Int. A1 | 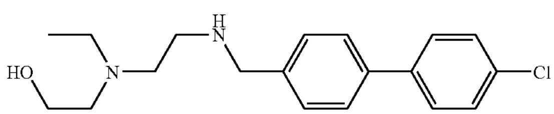 | N-(2-(N'-(2-hydroxyethyl)-N'-ethyl-amino)ethyl)-4-(4-chlorophenyl)-benzylamine |
| A95 | Int. A1 | 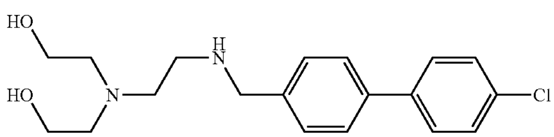 | N-(2-(bis-(2-hydroxyethyl)amino)ethyl)-4-(4-chlorophenyl)benzylamine |
| A96 | Int. A26 | 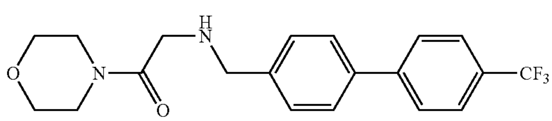 | N-((4-morpholino)carbonylmethyl)-4-(4-trifluoromethylphenyl)benzylamine |
| A97 | Int. A26 | 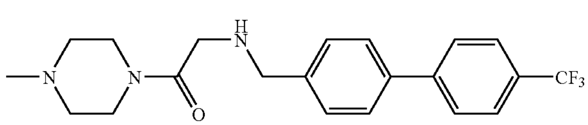 | N-((4-methyl-1-piperazino)carbonyl-methyl)-4-(4-trifluoromethylphenyl)-benzylamine |
| A98 | Int. A133 | 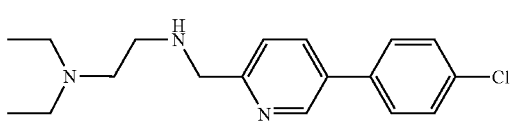 | N-(2-(diethylamino)ethyl)-5-(4-chloro-phenyl)pyrid-2-ylmethylamine |

-continued

| No. | Precursor | Structure | Name |
|---|---|---|---|
| A99 | Int. A134 | 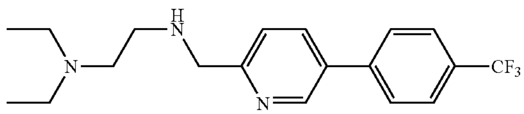 | N-(2-(diethylamino)ethyl)-5-(4-trifluoromethylphenyl)pyrid-2-ylmethylamine |
| A100 | Int. A132 | 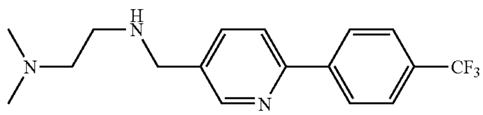 | N-(2-(dimethylamino)ethyl)-2-(4-trifluoromethylphenyl)pyrid-5-yl-methylamine |
| A101 | Int. A130 | 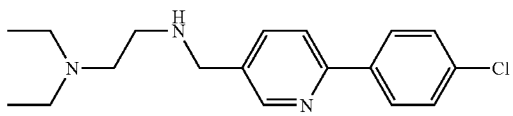 | N-(2-(diethylamino)ethyl)-2-(4-chlorophenyl)pyrid-5-ylmethylamine |
| A102 | Int. A135 | 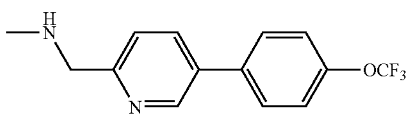 | N-methyl-5-(4-trifluoromethoxyphenyl)-pyrid-2-ylmethylamine |
| A103 | Int. A130 | 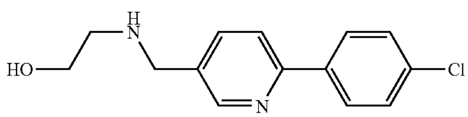 | N-(2-hydroxyethyl)-2-(4-chlorophenyl)-pyrid-5-ylmethylamine |
| A104 | Int. A136 | 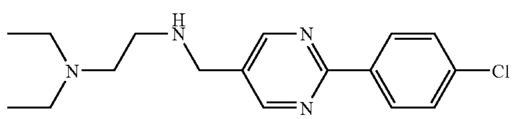 | N-(2-(diethylamino)ethyl)-2-(4-chlorophenyl)pyrimid-5-ylmethylamine |
| A105 | Int. A137 | 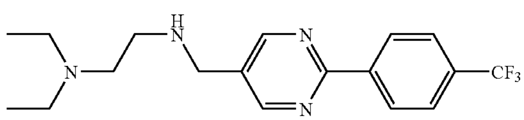 | N-(2-(diethylamino)ethyl)-2-(4-trifluoromethylphenyl)pyrimid-5-ylmethylamine |
| A106 | Int. A132 | 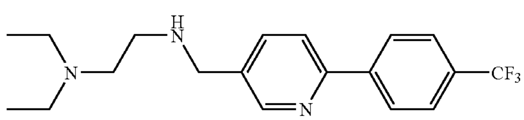 | N-(2-(diethylamino)ethyl)-2-(4-trifluoromethylphenyl)pyrid-5-ylmethylamine |
| A107 | Int. A1 | 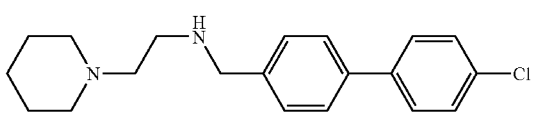 | N-(2-(1-piperidino)ethyl)-4-(4-chlorophenyl)benzylamine |
| A108 | Int. A26 | 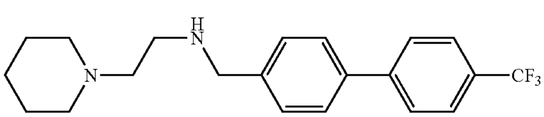 | N-(2-(1-piperadino)ethyl)-4-(4-trifluoromethylphenyl)benzylamine |

The following intermediates were made by the method of Intermediate A4:

| No. | Precursor | Structure | Name |
|---|---|---|---|
| A110 | Int. A20 | 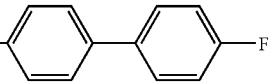 | 4-(4-Fluorophenyl)benzyl alcohol |

-continued

| No. | Precursor | Structure | Name |
|---|---|---|---|
| A111 | Int. A26 | 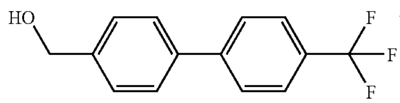 | 4-(4-Trifluoromethylphenyl)benzyl alcohol |
| A112 | Int. A22 | 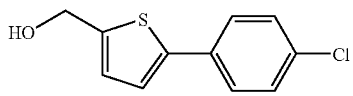 | 5-Hydroxymethyl-2-(4-chlorophenyl)thiophene |

The following intermediates were made by the method of Intermediate A5:

| No. | Precursor | Structure | Name |
|---|---|---|---|
| A115 | Int. A110 | 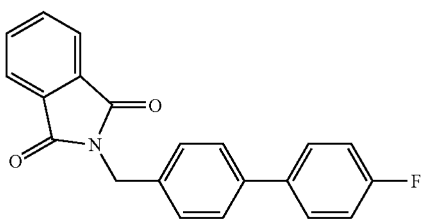 | N-(4-(4-Fluorophenyl)benzyl)phthalimide |
| A116 | Int. A111 | 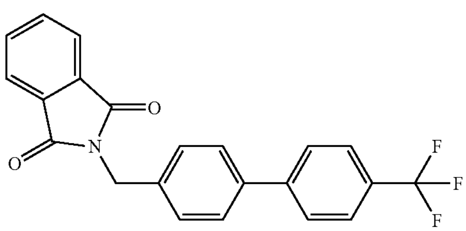 | N-(4-(4-Trifluoromethylphenyl)benzyl)-phthalimide |
| A117 | Int. A8 | 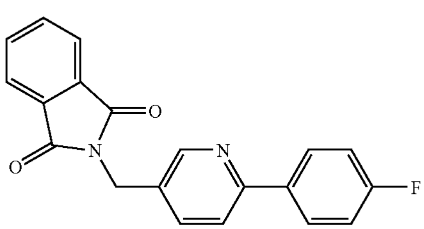 | N-(2-(4-Fluorophenyl)pyrid-5-ylmethyl)-phthalimide |
| A118 | Int. A112 | 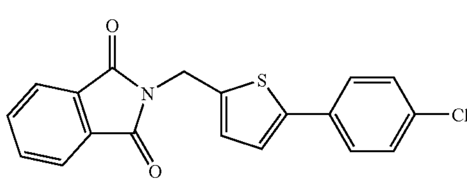 | N-(5-(4-Chlorophenyl)thien-2-ylmethyl)-phthalimide |

The following intermediates were made by the method of Intermediate A6:

| No. | Precursor | Structure | Name |
|-----|-----------|-----------|------|
| A120 | Int. A115 | 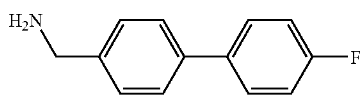 | 4-(4-Fluorophenyl)benzylamine |
| A121 | Int. A116 | 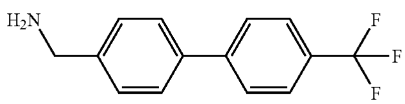 | 4-(4-Trifluoromethylphenyl)benzylamine |
| A122 | Int. A117 | 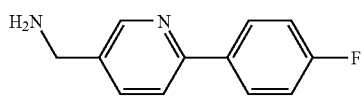 | 5-Aminomethyl-2-(4-fluorophenyl)pyridine |
| A123 | Int. A118 | 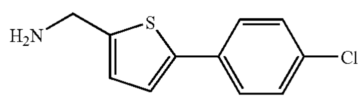 | 5-Aminomethyl-2-(4-chlorophenyl)thiophene |

A124: 4-Phenylbenzylamine is commercially available.
The following intermediates were made by the method of Intermediate A8:

| No. | Precursor | Structure | Name |
|-----|-----------|-----------|------|
| A125 | Int. A24 | 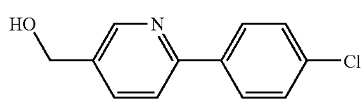 | 5-Hydroxymethyl-2-(4-chlorophenyl)pyridine |
| A126 | Int. A25 | 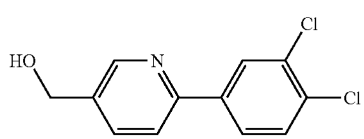 | 5-Hydroxymethyl-2-(3,4-dichlorophenyl)pyridine |
| A127 | Int. A40 | 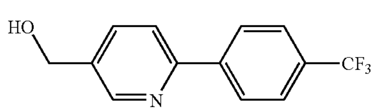 | 5-Hydroxymethyl-2-(4-trifluoromethylphenyl)-pyridine |
| A128 | Int. A15 | 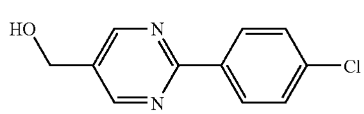 | 5-Hydroxymethyl-2-(4-chlorophenyl)pyrimidine |
| A129 | Int. A150 | 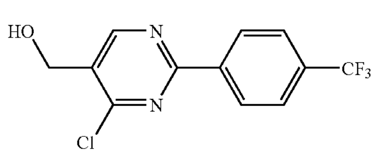 | 4-chloro-5-hydroxymethyl-2-(4-trifluoromethyl-phenyl)pyrimidine |

The following intermediates were made by the method of Intermediate A9:

| No. | Precursor | Structure | Name |
|---|---|---|---|
| A130 | Int. A125 | 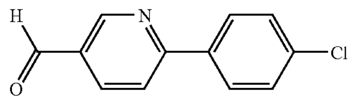 | 5-Formyl-2-(4-chlorophenyl)pyridine |
| A131 | Int. A126 | 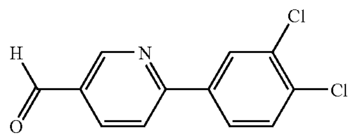 | 5-Formyl-2-(3,4-dichlorophenyl)pyridine |
| A132 | Int. A127 | 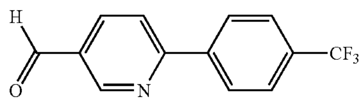 | 5-Formyl-2-(4-trifluoromethylphenyl)pyridine |
| A133 | Int. A12 | 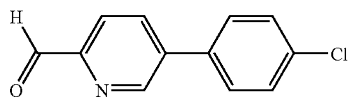 | 2-Formyl-5-(4-chlorophenyl)pyridine |
| A134 | Int. A140 | 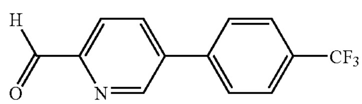 | 2-Formyl-5-(4-trifluoromethylphenyl)pyridine |
| A135 | Int. A141 | 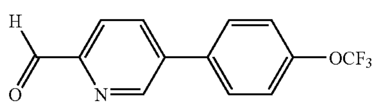 | 2-Formyl-5-(4-trifluoromethoxyphenyl)pyridine |
| A136 | Int. A128 | 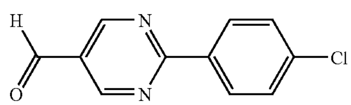 | 5-Formyl-2-(4-chlorophenyl)pyrimidine |
| A137 | Int. A16 | 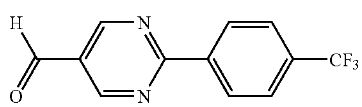 | 5-Formyl-2-(4-trifluoromethylphenyl)pyrimidine |

The following intermediates were made by the method of Intermediate A12:

| No. | Precursor | Structure | Name |
|---|---|---|---|
| A140 | Int. A134 | 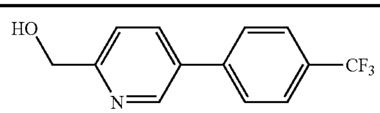 | 2-hydroxymethyl-5-(4-trifluoromethylphenyl)-pyridine |
| A141 | Int. A135 | 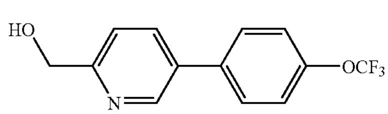 | 2-hydroxymethyl-5-(4-trifluoromethoxyphenyl)-pyridine |

The following intermediate was made by the method of Intermediate A13:

| No. | Precursors | Structure | Name |
|---|---|---|---|
| A145 | diethyl ethoxymalonate, 4-trifluoromethyl-benzamidine.HCl | EtO₂C— pyrimidinone —C₆H₄—CF₃ | Ethyl 2-(4-trifluoromethylphenyl)-4-oxopyrimidine-5-carboxylate |

The following intermediate was made by the method of Intermediate A14:

| No. | Precursor | Structure | Name |
|---|---|---|---|
| A150 | Int. A145 | EtO₂C— chloropyrimidine —C₆H₄—CF₃ | Ethyl 2-(4-trifluoromethylphenyl)-4-chloro-pyrimidine-5-carboxylate |

The following intermediate was made by the method of Intermediate A7:

| No. | Precursor | Structure | Name |
|---|---|---|---|
| A155 | Int. A45 | Br-CH₂-C(O)-N(Me)-CH₂-biphenyl-CF₃ | N-Methyl-N-(4-(4-trifluoromethylphenyl)-benzyl)bromoacetamide |

The following intermediate was made by the method of Intermediate A11:

| No. | Precursor | Structure | Name |
|---|---|---|---|
| A160 | Int. A26 | EtO₂C-CH₂-NH-CH₂-biphenyl-CF₃ | N-(Ethoxycarbonylmethyl)4-(4-trifluoromethyl-phenyl)benzylamine |

Intermediate B1—Ethyl 2-trifluoromethyl-4-oxopyrimidine-5-carboxylate

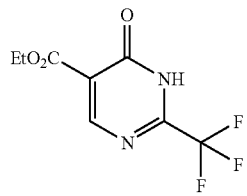

To a solution of trifluoroacetamidine (36.5 g) and diethyl ethoxymalonate (71 g) in ethanol (300 ml) was added a solution of sodium ethoxide in ethanol (21 wt %, 109.5 ml) over 5 min. The mixture was heated at reflux for 6 h, then cooled, concentrated and water (200 ml) added. The resulting solid was collected by filtration, washed with cold water (50 ml) and diethyl ether (2×100 ml) and then suspended in water (400 ml). Dichloromethane (300 ml) was added and the mixture acidified with dilute HCl (2.5 M, 125 ml). The organic extract was washed with water, dried (MgSO₄) and evaporated to give the tide compound as a buff solid (53 g, 68%). $^1$H-NMR (CDCl₃) δ 12.00 (1H, br s), 9.18 (1H, s), 4.57 (2H, q), 1.49 (3H, t); $^{13}$C-NMR (CDCl₃) δ 171.4, 167.3, 160.4, 160.2 (q, J=38 Hz), 118.8 (q, J=276 Hz), 109.2, 63.8, 14.0; MS (APCI+) found (M+1)=237, $C_8H_7F_3N_2O_3$ requires 236.

Intermediate B2—Ethyl 2-trifluoromethyl-4-chloropyrimidine-5-carboxylate

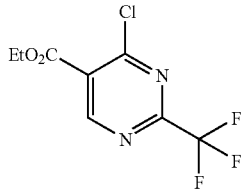

To a solution of ethyl 4-hydroxy-2-trifluorormethylpyrimidine-5-carboxylate (51.8 g) in dichloromethane (600 ml) cooled in an ice bath was added oxalyl chloride (57.4 ml) followed by dimethylformamide (0.2 ml). The mixture was stir at room temperature for 16 h and then evaporated. Toluene was added and evaporated. The residue was dissolved in dichloromethane, washed with water, dried (MgSO$_4$) and evaporated to give the title compound as an orange oil (55.7 g, 100%). $^1$H-NMR (CDCl$_3$) δ 9.25 (1H, s), 4.51 (2H, q), 1.46 (3H, t); $^{13}$C-NMR (CDCl$_3$) δ 126.0 (2C), 161.1, 158.1 (q, J=39 Hz), 127.0, 118.9 (q, J=276 Hz), 63.5, 14.4.

Intermediate B3—Ethyl 2-trifluorormethylpyrimidine-5-carboxylate

A mixture of ethyl 4-chloro-2-trifluoromethylpyrimidine-5-carboxylate (55.7 g), 10% palladium on carbon (0.3 g), ethanol (1000 ml) and N,N-diisopropylethylamine (90 ml) was shaken under hydrogen pressure maintained at 1 atmosphere for 2 h. The catalyst was then filtered off and the solvents evaporated. The residue was dissolved in dichloromethane, washed with ammonium chloride solution, then water, dried (MgSO$_4$) and evaporated to give the title compound as a buff solid (48 g, 100%). $^1$H-NMR (CDCl$_3$) δ 9.42 (2H, s), 4.51 (2H, q), 1.45 (3H, t); $^{13}$C-NMR (CDCl$_3$) δ 162.7, 159.4 (2C), 159.3 (q, J=37 Hz), 126.3, 119.6 (q, J=275 Hz), 62.9, 14.4.

Intermediate B4—2-Trifluoromethyl-5-formylpyrimidine

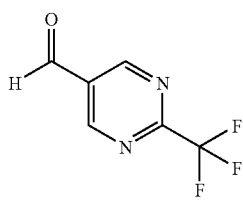

To a solution of ethyl 2-trifluoromethylpyrimidine-5-carboxylate (5.17 g) in toluene (120 ml) cooled in dry ice/acetone was added a solution of diisobutylaluminium hydride (25 wt %, 31 ml) over 15 min. The mixture was stirred at −78° C. for 45 min, then dilute HCl (2M, 120 ml) was added cautiously. After allowing the mixture to warm to room temperature diethyl ether was added. The organic phase was separated, washed with water, then brine, dried (MgSO$_4$) and evaporated to give the title compound as a colourless solid (3.46 g, 84%). $^1$H-NMR (CDCl$_3$) δ 10.29 (1H, s), 9.37 (2H, s); $^{13}$C-NMR (CDCl$_3$) δ 187.7, 159.6 (q, J=38 Hz), 159.1 (2C) 129.6, 119.2 (q, J=276 Hz).

Intermediate B5—1-(2-Methoxyethyl)pyrazole

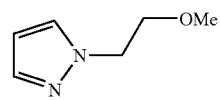

2-Bromomethyl methyl ether (10.22 g) was added dropwise with stirring to a mixture of pyrazole (5.0 g), finely powdered potassium hydroxide (8.25 g) and tetrabutylammonium bromide (1.19 g) with occasional ice cooling to keep the temperature below 10° C. The mixture was allowed to stand at room temperature for 48 hours, then columned on silica and eluted with ether. Product fractions were evaporated to a pale green oil (7.27 g). $^1$H-NMR (CDCl$_3$) δ 3.33 (3H,s), 3.75 (2H,t), 4.30 (2H,t), 6.25 (1H,s), 7.47 (1H,d), 7.52 (1H,d); MS (APCI+) found (M+H)=127; C$_6$H$_{10}$N$_2$O requires 126.

Intermediate B6—1-(2-Methoxyethyl)pyrazole carboxaldehyde

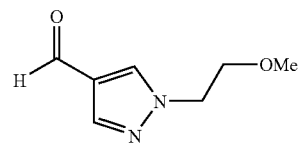

A solution of 1-(2-methoxyethyl)pyrazole (7.27 g) in dry DMF (11.4 ml) was heated to 90° C., then phosphorus oxychloride (5.4 ml) was added dropwise over 1 hour, maintaining the temperature between 95–100° C. After heating for a further 2 hours, the mixture was cooled and poured onto ice. Sodium hydroxide was added to adjust the mixture to pH 4, then the product was extracted into dichloromethane. Drying and evaporation of the organic extracts yielded a brown oil (7.19 g). $^1$H-NMR (CDCl$_3$) δ 3.34 (3H,s), 3.75 (2H,m), 4.32 (2H,m), 7.98 (1H,s), 8.02 (1H,s), 9.85 (1H,s).

Intermediate B10—3-(1-Methylpyrazol-4-yl)acrylic acid

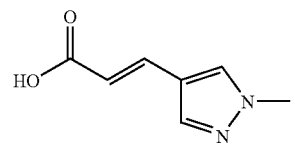

A mixture of 1-methylpyrazole-4-carboxaldehyde (85.55 g), malonic acid (80.85 g), pyridine (69.2 ml) and piperidine (1.5 ml) was heated to 110° C. under argon for 4 hours. After cooling, water (100 ml) was added, followed by aqueous ammonia (75 ml) to obtain a clear solution, which was acidified to pH1 with hydrochloric acid. The resulting solid was filtered off, washed with water and dried to obtain the tide compound (93.5 g). ¹H-NMR (d₆-DMSO) δ 3.83 (3H,s), 6.18 (1H,d), 7.44 (1H,d), 7.83 (1H,s), 8.07 (1H,s). (APCI) found (M+H)=153. C₇H₈N₂O₂ requires 152.

Intermediate B11—Methyl 3-(1-methylpyrazol-4-yl)acrylate

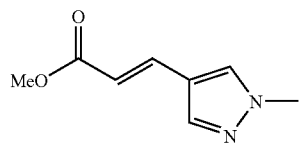

3-(1-Methylpyrazol-4-yl)acrylic acid (86.8 g) was added to a solution of sulphuric acid (20 ml) in methanol (690 ml), and the mixture refluxed for 2.5 hours, cooled, then poured onto ice. The acid was neutralised with aqueous sodium hydroxide and the product extracted into dichloromethane, which was dried and evaporated. Crystallisation from ether/petrol gave methyl 3-(1-methylpyrazol-4-yl)acrylate (89.0 g). ¹H-NMR (d₆-DMSO) δ 3.77 (3H,s), 3.91 (3H,s), 6.16 (1H,d), 7.54 (1H,s), 7.56 (1H,d), 7.69 (1H,s). (APCI) found (M+H)=167. C₈H₁₀N₂O₂ requires 166.

Intermediate B12—Ethyl 3-(5-pyrimidinyl)acrylate

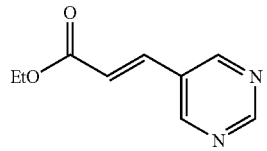

A mixture of 5-bromopyrimidine (5.93 g), ethyl acrylate (5.08 g), palladium acetate (0.112 g), triphenyl phosphine (0.23 g) and triethylamine (4.5 g) was stirred at 150° C. in a pressure vessel for 6 hours. After cooling overnight, water (50 ml) was added to the dark residue, and the product was extracted into toluene. Drying, charcoaling and evaporation gave a pale oil, which was triturated with pet ether to obtain ethyl 3-(5-pyrimidyl)acrylate (4.78 g). ¹H-NMR (CDCl₃) δ 1.36 (3H,t), 4.27 (2H,q), 6.59 (1H,d), 7.62 (1H,d), 8.88 (2H,s), 9.20 (1H,s).

Intermediate B13—Ethyl 3-(2-methoxypyrimidin-5-yl)acrylate

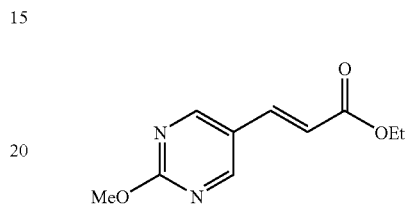

A mixture of 2-methoxy-5-bromopyrimidine (75.43 g, 0.399 mol), ethyl acrylate (47.5 ml, 0.439 mol), palladium (II) acetate (1.07 g, 0.0048 mol), tri-o-tolylphosphine (2.92 g, 0.0096 mol) and triethylamine (84 ml) were heated at 135° C. (oil bath temperature) with stirring under argon for 12 h. After allowing to cool the solid mass was dissolved in water and ethyl acetate, filtered, and the aqueous phase separated and further extracted with ethyl acetate. The combined extracts were washed with saturated aqueous ammonium chloride, dried (MgSO₄) and evaporated. The solid thus obtained was triturated with ether/light petrol (1:3, 350 ml), filtered, washed and dried, yield 52.41 g (63%). ¹H-NMR (CDCl₃) δ 1.33 (3H, t), 4.06 (3H, s), 4.28 (2H, q), 6.45 (1H, d), 7.58 (1H, d), 8.67 (2H, s); MS (APCI+) found (M+H)=209; C₁₀H₁₂N₂O₃ requires 208.

The following intermediates were prepared by the method of intermediate B10 (Knoevenagel):

| No. | Precursors | Structure | Name |
|---|---|---|---|
| B14 | Int. B4 | 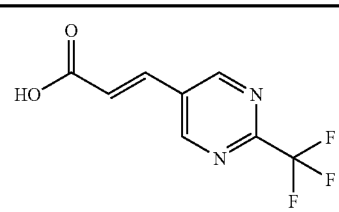 | 3-(2-Trifluoromethylpyrimidin-5-yl)acrylic acid |
| B15 | Int. B6 | 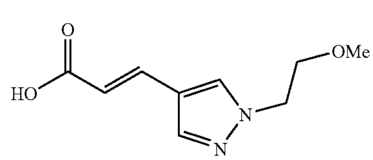 | 3-(1-(2-Methoxyethyl)pyrazol-4-yl)acrylic acid |

The following intermediates were prepared by the method of intermediate B11 (esterification):

| No. | Precursors | Structure | Name |
|---|---|---|---|
| B16 | Int. B14 | 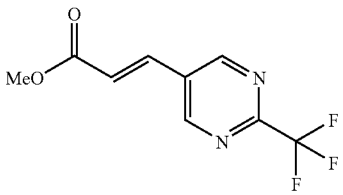 | Methyl 3-(2-trifluoromethylpyrimidin-5-yl)acrylate |
| B17 | Int. B15 | 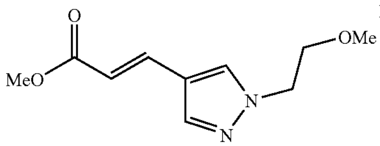 | Methyl 3-(1-(2-methoxyethyl)pyrazol-4-yl)acrylate |

The following intermediates were prepared by the method of intermediate B13 (acrylate Heck):

| No. | Precursors | Structure | Name |
|---|---|---|---|
| B18 | 2-dimethylamino-5-bromopyrimidine | 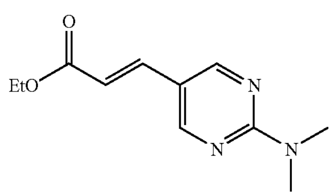 | Ethyl 3-(2-dimethylamino-5-pyrimidyl)-acrylate |
| B19 | 2-(4-morpholino)-5-bromopyrimidine | 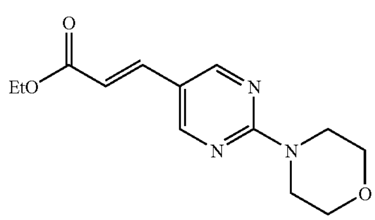 | Ethyl 3-[2-(4-morpholino)-5-pyrimidyl]-acrylate |

Intermediate B20—Methyl 3-(1-methylpyrazol-4-yl)propionate

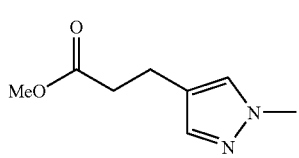

A solution of methyl 3-(1-methylpyrazol-4-yl)acrylate (181 g) in methanol (2 litres) was hydrogenated over 10% palladium on charcoal (5.2 g) at 50° C./50 psi until uptake ceased. The catalyst was filtered off, the methanol was removed in vacuo, finally by azeotroping with toluene. The title compound was obtained as an oil (179 g). $^1$H-NMR (d$_6$-DMSO) δ 2.56 (2H,t), 2.79 (2H,t), 3.67 (3H,s), 3.85 (3H,s), 7.17 (1H,s), 7.31 (3H,s). (APCI) M+H=169. $C_8H_{12}N_2O_2$ requires 168.

Intermediate B21—Ethyl 3-(2-methoxypyrimidin-5-yl)propanoate

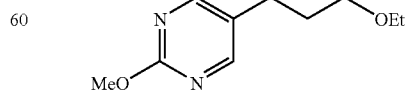

A suspension of ethyl 3-(2-methoxypyrimidin-5-yl)acrylate (52.4 g, 0.252 mol) in ethanol (400 ml) and triethylamine (50 ml) was treated with 10% palladium on carbon (3 g) and hydrogenated at 50 psi for 1.75 h. The catalyst was filtered off through hyflo and the filtrate evaporated. The residue was dissolved in dichloromethane, washed twice with saturated aqueous ammonium chloride, dried (MgSO$_4$) and evaporated to an oil, yield 41.2 g (78%). $^1$H-NMR (CDCl$_3$) δ 1.23 (3H, t), 2.61 (2H, t), 2.87 (2H, t), 3.99 (3H, s), 4.13 (2H, q), 8.39 (2H, s); MS (APCI+) found (M+H) =211; C$_{10}$H$_{14}$N$_2$O$_3$ requires 210.

The following intermediates were made by the method of Intermediate B20 (ethyl esters in ethanol solvent, methyl esters in methanol):

Intermediate B30—5-((1-Methylpyrazol-4-yl)methyl)-2-thiouracil

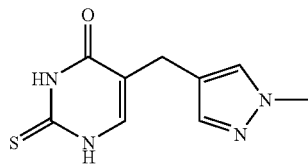

A solution of methyl 3-(1-methylpyrazol-4-yl)propionate (170 g) and methyl formate (131 ml) in dry diethyl ether (2000 ml) was added dropwise over 2 hours to a stirred, ice-cooled solution of potassium tert-butoxide (284 g) in dry THF (1800 ml) under argon. The mixture was then allowed

| No. | Precursors | Structure | Name |
|-----|------------|-----------|------|
| B22 | Int. B12 | 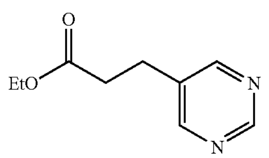 | Ethyl 3-(5-pyrimidyl)propionate |
| B23 | Int. B17 | 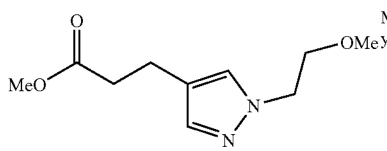 | Methyl 3-(1-(2-methoxyethyl)pyrazol-4-yl)propionate |

The following intermediates were made by the method of Intermediate B21 (ethyl esters in ethanol solvent, methyl esters in methanol):

| No. | Precursors | Structure | Name |
|-----|------------|-----------|------|
| B24 | Int. B16 | 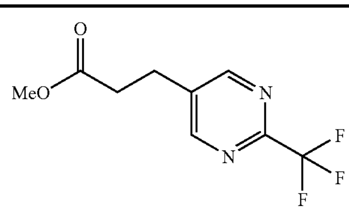 | Methyl 3-(2-trifluoromethylpyrimidin-5-yl)-propanoate |
| B25 | Int. B18 | 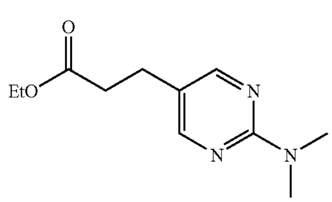 | Ethyl 3-(2-dimethylamino-5-pyrimidyl)propionate |
| B26 | Int. B19 | | Ethyl 3-[2-(4-morpholino)-5-pyrimidyl]propionate | to warm to room temperature and stirring continued for 16 hours. The solvents were evaporated in vacuo to a pale solid. Methanol (2500 ml) and thiourea (154 g) were added, and the mixture was heated to 50° C. for 16 hours with vigorous stirring. The solvent was evaporated, and the pale brown solid residue was taken up in water (750 ml). The ice-cooled solution was adjusted to pH3 with hydrochloric acid, stirred for 2 hours in the ice bath, then the precipitat was filtered off and washed with water and ether to obtain the title compound (120 g). $^1$H-NMR (d$_6$-DMSO) δ 3.33 (3H,s), 3.75 (3H,s), 7.15 (1H,s), 7.23 (1H,s), 7.46 (1H,s), 12.2 (1H,br s), 12.4 (1H,br s). (APCI) M+H=223. C$_9$H$_{10}$N$_4$OS requires 222.

Intermediate B31—Ethyl 2-formyl-3-(5-pyrimidyl)propionate

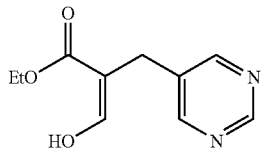

A mixture of ethyl 3-(5-pyrimidyl)propionate (2.28 g) and ethyl formate (1.41 ml) dissolved in dry dimethoxyethane (5 ml) was added dropwise over 30 min to a suspension of sodium hydride (60%, 4.0 g) in DME (5 ml) under nitrogen, keeping the temperature below 0° C. Stirring was continued for a further 24 h, then the mixture was poured onto ice and washed with ether. The aqueous layer was adjusted to pH 7, then evaporated and the residue extracted with acetone. Filtration and evaporation gave crude product, which was taken up in ethyl acetate, charcoaled, dried and evaporated to give ethyl 2-formyl-3-5-pyrimidyl)propionate. Like other compounds of this type, this proved difficult to characterise and was used without further purification.

Intermediate B32—5-(Pyrimid-5-ylmethyl)-2-thiouracil

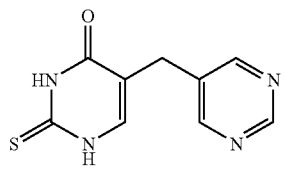

Sodium (0.25 g) was dissolved in ethanol (5 ml), thiourea (0.77 g) added, and the mixture stirred under reflux for 1 hour. A solution of ethyl 2-formyl-3-(5-pyrimidyl)propionate (1.99 g) in ethanol (5 ml) was added slowly, and reflux continued for 18 hours. The solvent was evaporated, and the residue taken up in water and washed with dichloromethane. The aqueous solution was acidified to pH 5, and the precipitate filtered off, washed with water and dried to obtain 5-pyrimid-5-ylmethyl)-2-thiouracil (0.71 g). $^1$H-NMR (d6-DMSO) δ 3.58 (2H,s), 7.54 (1H,s), 8.70 (2H,s) and 9.02 (1H,s). MPt 265–6° C.

The following intermediates were made by the method of Intermediate B30 (thiouracils):

| No. | Precursors | Structure | Name |
|---|---|---|---|
| B33 | Int. B21 | 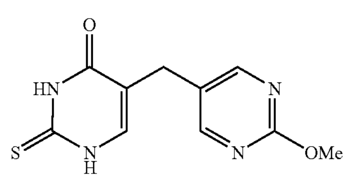 | 5-(2-Methoxypyrimidin-5-ylmethyl)-2-thiouracil |
| B34 | Int. B24 | 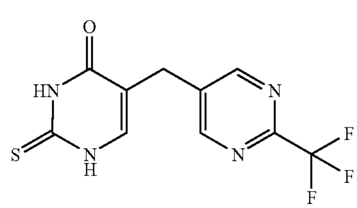 | 5-(2-Trifluoromethylpyrimidin-5-ylmethyl)-2-thiouracil |
| B35 | Int. B26 | 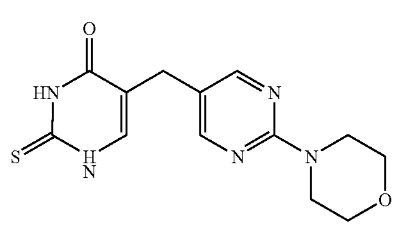 | 5-(2-(4-Morpholino)pyrimid-5-ylmethyl)-2-thiouracil |

| No. | Precursors | Structure | Name |
|---|---|---|---|
| B36 | Int. B25 | 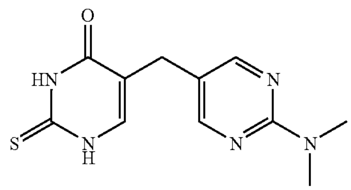 | 5-(2-Dimethylaminopyrimid-5-ylmethyl)-2-thiouracil |
| B37 | Int. B23 | 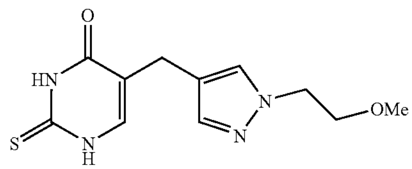 | 5-((1-(2-Methoxyethyl)pyrazol-4-yl)methyl)-2-thiouracil |
| B38 | ethyl 3-phenyl-propionate | 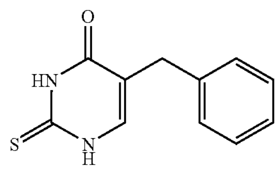 | 5-Benzyl-2-thiouracil |
| B39 | ethyl 3-(4-chlorophenyl)-propionate | 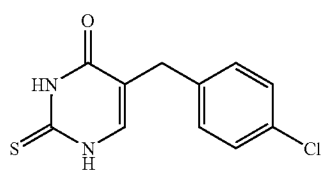 | 5-(4-Chlorobenzyl)-2-thiouracil |

Intermediate B40—2-(Methoxymethylene)-3-(2-methoxy-pyrimidin-5-yl)propionic acid, mixed methyl/ethyl esters

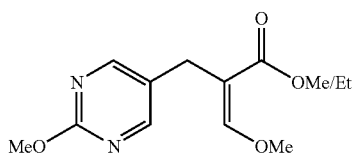

To a stirring suspension of sodium hydride (0.83 g of a 60% dispersion in oil) in anhydrous 1,2-dimethoxyethane (6 ml) was added dropwise a solution of methyl formate (1.54 ml) and ethyl 3-(2-methoxypyrimid-5-yl)propionate (3.5 g) in anhydrous 1,2-dimethoxyethane (6 ml) at such a rate as to maintain the reaction temperature at 25–30° C. After 1 h, ether was added and the precipitated oil allowed to settle. The solution was decanted off and replaced with fresh ether, and the oil slowly solidified. The solid 2-(hydroxymethyl-ene) derivative was filtered, washed with ether and dried, yield 3.8 g. A 1.33 g portion was suspended in dimethyl formamide (10 ml) together with anhydrous potassium carbonate (1.15 g), and a solution of dimethyl sulphate (0.48 ml) in dimethylformamide (10 ml) was added dropwise with stirring over 30 min. After 16 h the solvent was evaporated and the residue treated with water and extracted with ethyl acetate. The extracts were washed with water, dried (MgSO$_4$) and evaporated to give the product as an oil, yield 0.91 g. $^1$H-NMR (CDCl$_3$) δ 1.23 (3H, t), 3.46 (2H, s), 3.69 (3H, s, methyl ester), 3.88 (3H, s), 3.97 (3H, s), 4.16 (2H, q), 7.39 (1H, s), 8.40 (2H, s). 3:2 ratio of methyl:ethyl esters. MS (APCI+) found (M+1)=253, 239 (ethyl and methyl esters); C$_{12}$H$_{16}$N$_2$O$_4$ requires 252, C$_{11}$H$_{14}$N$_2$O$_4$ requires 238.

Intermediate B41—2-(Methoxymethylene)-3-(2-methoxy-pyrimidin-5-yl)propionic acid

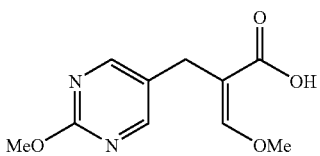

A suspension of the mixed esters of Intermediate B40 (0.9 g) in 2M aqueous sodium hydroxide (3.6 ml) was stirred at ambient temperature for 16 h to give a clear solution. This was diluted with water, extracted with dichloromethane and evaporated to about half volume, then acidified to pH 3–4 (2M hydrochloric acid) when the product crystallised out. The white solid was filtered, washed with ice-cold water and dried, yield 0.46 g. $^1$H-NMR (CDCl$_3$) δ 3.43 (2H, s), 3.91 (3H, s), 3.99 (3H, s,) 7.49 (1H, s), 8.42 (2H, s); MS (APCI+) found (M+1)=225, C$_{10}$H$_{12}$N$_2$O$_4$ requires 224.

Intermediate B42—1-(3-Ethoxycarbonylprop-1-yl)-5-(2-methoxypyrimid-5-ylmethyl)-2-thiouracil

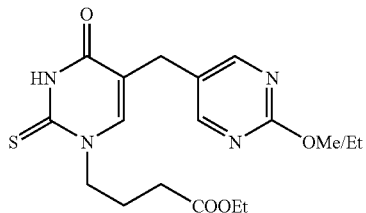

Oxalyl chloride (3.94 ml, 2 equiv) was added over 5 min to a solution of Intermediate B41 (5.0 g, 1 equiv) and DMF (1 drop) in dry dichloromethane (50 ml), then the mixture was stirred under argon for 4 h. The solvent was evaporated, and the residue twice taken up in dichloromethane and re-evaporated to remove volatile impurities. The acid chloride was dissolved in acetonitrile (100 ml) and treated with dry, powdered potassium thiocyanate (3.2 g, 1.5 equiv). The resulting suspension was stirred under argon for 24 h, then evaporated to dryness. The residue was suspended in dry DMF (100 ml), cooled to 10° C., ethyl 4-aminobutyrate hydrochloride (4.60 g, 1.25 equiv) and triethylamine (7.34 ml, 2.4 equiv) added, and the mixture stirred at room temperature for 20 h. Sodium methoxide solution (prepared by dissolving sodium (1.26 g, 2.5 equiv) in methanol (25 ml)) was added to the DMF solution, and the mixture heated to 110° C. for 2 h. The solvent was evaporated, water was added, and acidified to pH 5 with acetic acid, then the product extracted into ethyl acetate. Drying, evaporation, and trituration with ether gave a pale brown solid (4.55 g). Some ether/ester exchange took place during the reaction, and the title compound was obtained mixed with ca 30% of the corresponding 2-ethoxypyrimidine. $^1$H-NMR (DMSO-$d_6$) δ 1.17 (3H, t), 1.31 (t, ethoxy), 1.97 (2H, t), 2.36 (2H, t), 3.49 (s, ethoxy), 3.51 (s, methoxy), 3.88 (s, methoxy), 4.04 (2H, q), 4.16 (2H, t), 4.31 (q, ethoxy), 7.81 (1H, s), 8.48 (s, ethoxy), 850 (s, methoxy), 12.50 (bs, NH) (light brown solid).

The following intermediates were prepared by the method of intermediate B40:

| No. | Precursor | Structure | Name |
|---|---|---|---|
| B43 | Int. B20 | 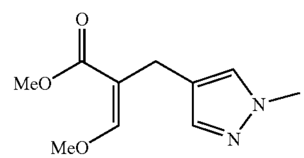 | Methyl 2-(methoxymethylene)-3-(1-methylpyrazol-4-yl)propionate |
| B44 | Int. B26 | 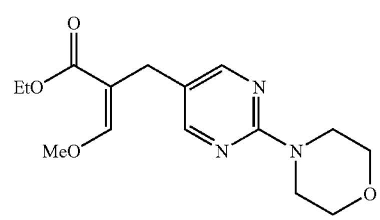 | Ethyl 2-(methoxymethylene)-3-(2-(4-morpholino)-pyrimidin-5-yl)propionate |

The following intermediates were prepared by the method of intermediate B41:

| No. | Precursors | Structure | Name |
|---|---|---|---|
| B45 | Int. B43 | 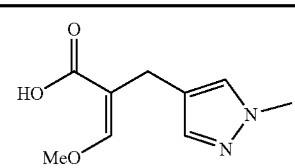 | 2-(Methoxymethylene)-3-(1-methylpyrazol-4-yl)-propionic acid |
| B46 | Int. B44 | 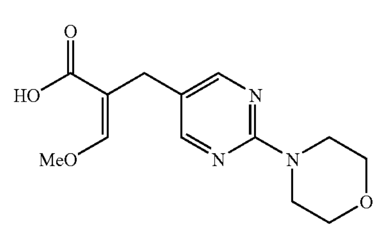 | 2-(Methoxymethylene)-3-(2-(4-morpholino)pyrimidin-5-yl)propionic acid |

The following intermediates were prepared by the method of intermediate B42:

| No. | Precursors | Structure | Name |
|---|---|---|---|
| B47 | Int. B45 | 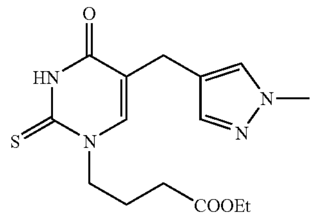 | 1-(3-Ethoxycarbonylprop-1-yl)-5-(1-methylpyrazol-4-ylmethyl)-2-thiouracil |
| B48 | Int. B46 | 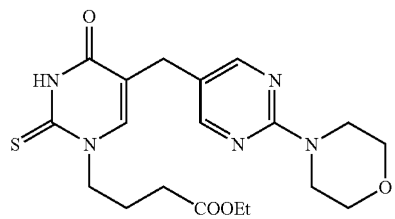 | 1-(3-Ethoxycarbonylprop-1-yl)-5-(2-(4-morpholino)-pyrimid-5-ylmethyl)-2-thiouracil |

Intermediate B50—2-(4-Fluorobenzylthio)-5-((1-methylpyrazol-4-yl)methyl)pyrimidin-4-one

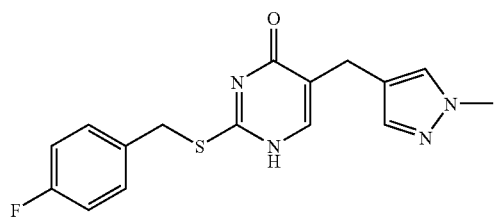

A mixture of 5-((1-methylpyrazol-4-yl)methyl)-2-thiouracil (118 g), 4-fluorobenzyl chloride (76.8 g), potassium carbonate (183.5 g), and dry DMF (100 ml) was stirred under argon at 80° C. for 16 hours, then cooled and evaporated. The solid residue was suspended in water (1500 ml) with vigorous stirring, then acidified to pH2 with hydrochloric acid and stirred for a further hour. The white solid was filtered off and washed with water and ether to obtain the title compound (168 g). $^1$H-NMR (d6-DMSO) δ 3.47 (2H, s), 3.81 (3H, s), 4.41 (2H, s), 7.19 (2H, s), 7.29 (1H, s), 7.48 (3H, m), 7.84 (1H, s), 12.74 (1H, br.s); MS (APCI+) found (M+1)=331; $C_{16}H_{15}FN_4OS$ requires 330.

Intermediate B51—1-(3-Ethoxycarbonylprop-1-yl)-2-(4-fluorobenzyl)thio-5-(2-methoxy-pyrimid-5-ylmethyl)pyrimidin-4-one

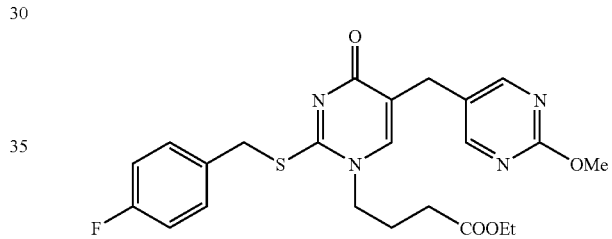

Intermediate B24 (1.0 g, 1 equiv) in dichloromethane (60 ml) was treated with diisopropylethylamine (0.63 ml, 1.3 equiv) followed by 4-fluorobenzyl bromide (0.38 ml, 1.1 equiv), giving an orange solution which was stirred under argon for 4 h, then washed with water, dried and evaporated. Chromatography (silica, 5% ethanol in ethyl acetate) eluted first the 2-ethoxypyrimidine impurity, followed by the title compound (0.35 g). $^1$H-NMR (CDCl$_3$) δ 1.25 (3H, t), 2.03 (2H, m), 2.33 (2H, t), 3.64 (2H, s) 3.83 (2H, m), 3.99 (3H, s), 4.12 (2H, q), 4.47 (2H, s), 6.98 (3H, m), 7.37 (2H, m), 8.46 (2H, s); MS (APCI+) M+1=473; $C_{23}H_{25}FN_4O_4S$ requires 472 (pale waxy solid).

The following intermediates were prepared by the method of intermediate B50:

| No | Precursors | Structure | Name |
|---|---|---|---|
| B52 | Int. B32 | 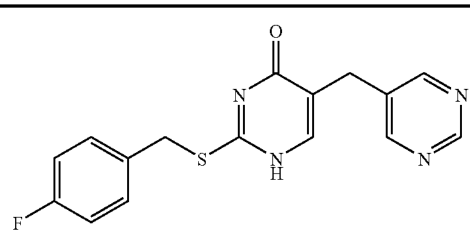 | 2-(4-Fluorobenzylthio)-5-((pyrimid-5-yl)methyl)pyrimidin-4-one |

| No | Precursors | Structure | Name |
|---|---|---|---|
| B53 | Int. B33 | 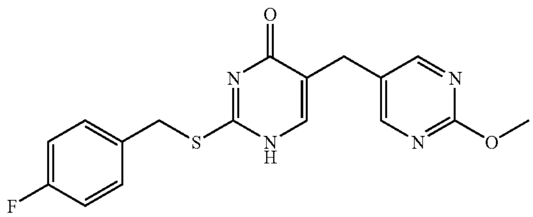 | 2-(4-Fluorobenzylthio)-5-((2-methoxy-pyrimid-5-yl)methyl)pyrimidin-4-one |
| B54 | Int. B34 | 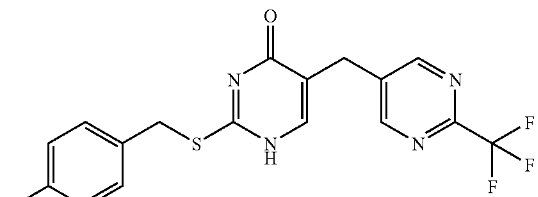 | 2-(4-Fluorobenzylthio)-5-((2-trifluoromethylpyrimid-5-yl)methyl)pyrimidin-4-one |
| B55 | Int. B35 | 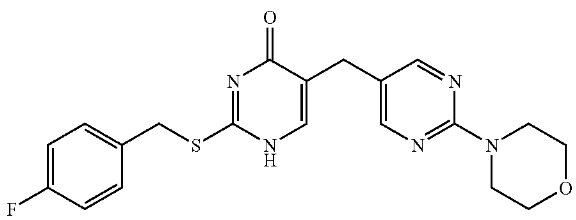 | 2-(4-Fluorobenzyl)thio-5-(2-(4-morpholino)pyrimid-5-ylmethyl)pyrimidin-4-one |
| B56 | Int. B36 | 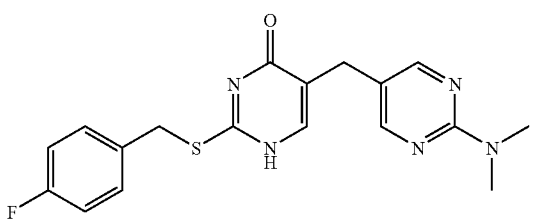 | 2-(4-Fluorobenzyl)thio-5-(2-dimethylaminopyrimid-5-yl-methyl)pyrimidin-4-one |
| B57 | Int. B33 + 3,4-difluoro-benzyl chloride | 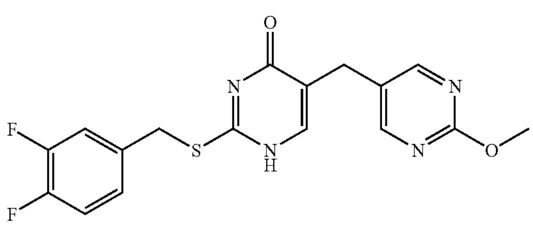 | 2-(3,4-Difluorobenzylthio)-5-((2-methoxy-pyrimid-5-yl)methyl)pyrimidin-4-one |
| B58 | Int. B37 | 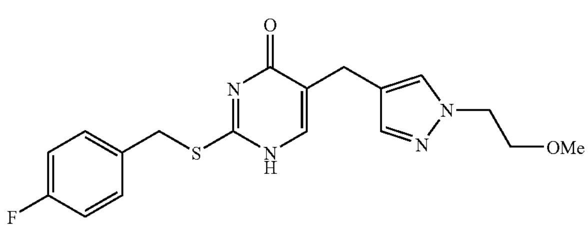 | 2-(4-Fluorobenzylthio)-5-((1-(2-methoxy-ethyl)pyrazol-4-yl)methyl)pyrimidin-4-one |
| B59 | Int. B30 + benzyl chloride | 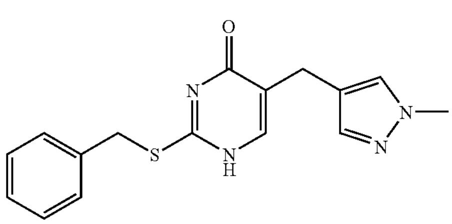 | 2-Benzylthio-5-(1-methylpyrazol-4-yl-methyl)pyrimidin-4-one |

| No | Precursors | Structure | Name |
|---|---|---|---|
| B60 | Int. B30 + 2,6-dimethyl-4-chloromethyl-pyridine | 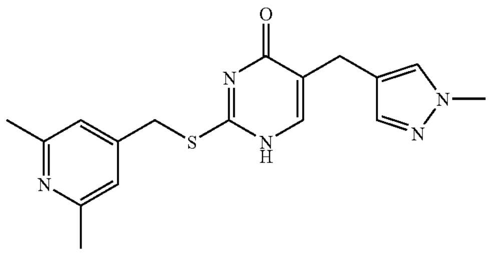 | 2-(2,6-Dimethylpyrid-4-yl)methylthio-5-(1-methylpyrazol-4-ylmethyl)pyrimidin-4-one |
| B61 | Int. B33 + 2,6-dichloro-4-chloromethyl-pyridine | 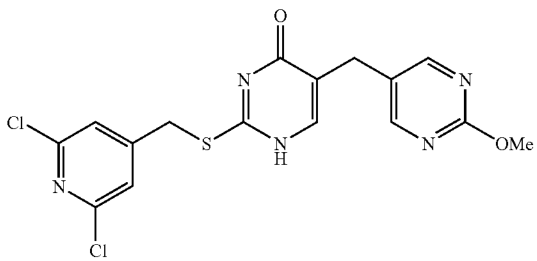 | 2-(2,6-Dichloropyrid-4-yl)methylthio-5-(2-methoxypyrimid-5-ylmethyl)pyrimidin-4-one |
| B62 | Int. B33 + 3-chloro-methylpyridine | 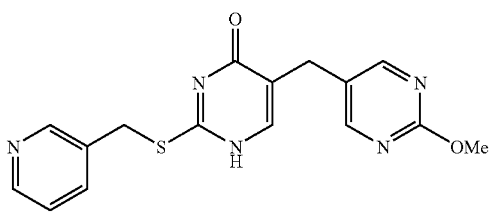 | 2-(Pyrid-3-yl)methylthio-5-(2-methoxy-pyrimid-5-ylmethyl)pyrimidin-4-one |
| B63 | Int. B33 + 4-chloro-methyl2-methylpyridine | 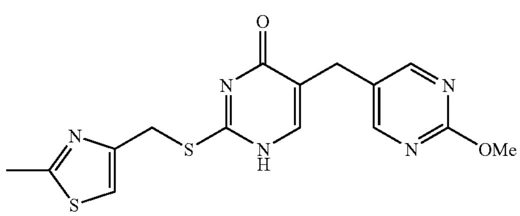 | 2-(2-Methylthiazol-4-yl)methylthio-5-(2-methoxypyrimid-5-ylmethyl)pyrimidin-4-one |
| B64 | Int. B38 | 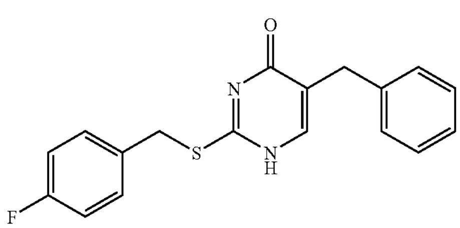 | 2-(4-Fluorobenzylthio)-5-benzylpyrimidin-4-one |
| B65 | Int. B39 | 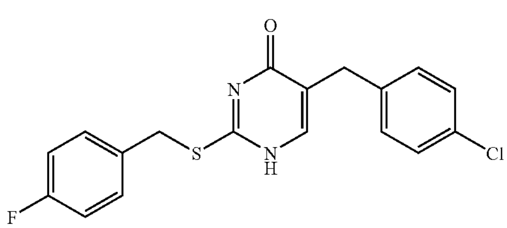 | 2-(4-Fluorobenzylthio)-5-(4-chlorobenzyl)-pyrimidin-4-one |

| No | Precursors | Structure | Name |
|---|---|---|---|
| B66 | Int. B30 + 3,4-difluoro-benzyl chloride | 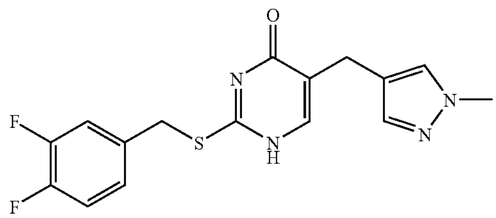 | 2-Benzylthio-5-(1-methylpyrazol-4-yl-methyl)pyrimidin-4-one |

The following intermediates were prepared by the method of intermediate B51:

| No. | Precursors | Structure | Name |
|---|---|---|---|
| B67 | Int. B47 | 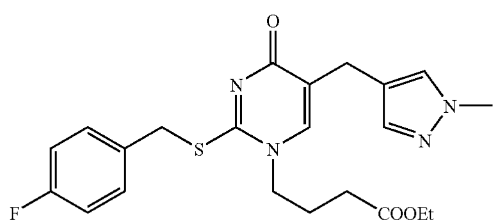 | 1-(3-Ethoxycarbonylprop-1-yl)-2-(4-fluoro-benzyl)thio-5-(1-methylpyrazol-4-ylmethyl)-pyrimidin-4-one |
| B68 | Int. B48 | 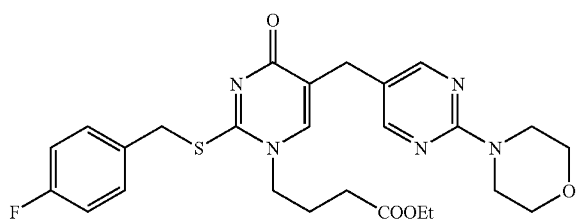 | 1-(3-Ethoxycarbonylprop-1-yl)-2-(4-fluoro-benzyl)thio-5-(2-(4-morpholino)pyrimid-5-yl-methyl)pyrimidin-4-one |

Intermediate B70—1-(tert-Butoxycarbonylmethyl)-2-(4-fluorobenzylthio)-5-((1-methylpyrazol-4-yl)methyl)pyrimidin-4-one

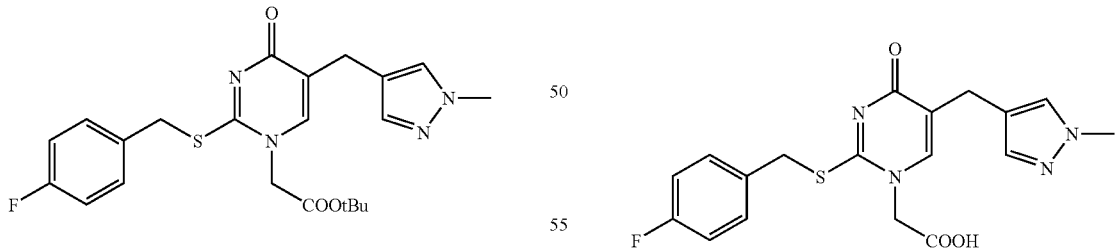

A mixture of 2-(4-fluorobenzylthio)-5-((1-methylpyrazol-4-yl)methyl)pyrimidin-4-one (175 g), tert-butyl iodoacetate (128.3 g), diisopropylethylamine (101.5 ml) and dichloromethane (200 ml) was stirred at room temperature under argon for 48 hours. The solution was washed with aq. sodium bicarbonate then with aq. ammonium chloride, dried and evaporated to a pale viscous oil. Ethyl acetate (300 ml) was added, the precipitate was filtered off and discarded, and the solution was chromatographed (silica, 2.5%–10% methanol+0.5% aq. ammonia in dichloromethane). Product fractions were evaporated to an orange solid which solidified on standing (140 g). $^1$H-NMR (d$_6$-DMSO) δ 1.36 (9H,s), 3.37 (2H,s), 3.76 (3H,s), 4.42 (2H,s), 4.65 (2H,s), 7.13 (2H,m), 7.23 (1H,m), 7.45 (4H,m); MS (APCI+) found (M+1)=445; $C_{22}H_{25}FN_4O_3S$ requires 444.

Intermediate B71—1-(Carboxymethyl)-2-(4-fluorobenzylthio)-5-((1-methylpyrazol-4-yl)methyl)-pyrimidin-4-one 1-(tert-Butoxycarbonylmethyl)-2-(4-fluorobenzylthio)-5-((1-methylpyrazol-4-yl)methyl)pyrimidin-4-one (96.8 g) was dissolved in dichloromethane (195 ml), cooled in ice/water, and trifluoroacetic acid (130 ml) added slowly with rapid stirring. After a further 36 hours stirring, the solvent was evaporated and the glassy residue triturated with ether; yield 78.6 g. $^1$H-NMR (d6-DMSO) δ 3.36 (2H, s), 3.76 (3H, s), 4.41 (2H, s), 4.67 (2H, s), 7.14 (2H, m), 7.23 (1H, s), 7.43–7.49 (4H, m); MS (APCI+) found (M+1)=389; $C_{18}H_{17}FN_4O_3S$ requires 388.

Intermediate B72—1-Ethoxycarbonylmethyl-2-(4-fluorobenzyl)thio-5-(pyrimid-5-ylmethyl)-pyrimidin-4-one

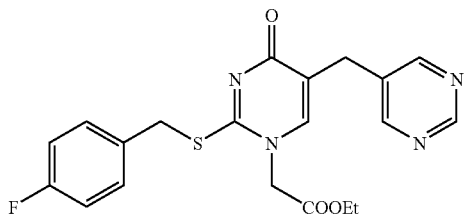

A mixture of intermediate B52 (10 g), ethyl bromoacetate (3.38 ml), diisopropylethylamine (5.84 ml) and dichloromethane (50 ml) was stirred overnight, then the solution was washed sequentially with aqueous ammonium chloride and aqueous sodium bicarbonate. Chromatography (silica, 5–10% methanol in ethyl acetate) and trituration with ether gave the desired product (7.02 g). $^1$H-NMR (CDCl$_3$) δ 1.26 (3H, t), 3.71 (2H, s), 4.26 (2H, q), 4.46 (2H, s), 4.48 (2H, s), 6.91 (1H, s), 6.98 (2H, m), 7.35 (2H, m), 8.70 (2H, s), 9.09 (1H, s); MS(APCI$^+$) M+1=415, $C_{20}H_{19}FN_4O_3S$ requires 414. MPt 145.1° C.

Intermediate B73—1-Carboxymethyl-2-(4-fluorobenzyl)thio-5-(pyrimid-5-ylmethyl)pyrimidin-4-one

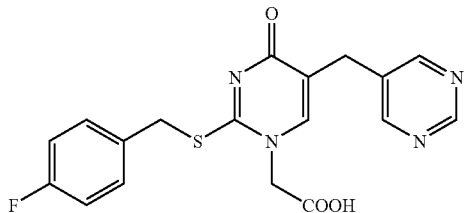

0.5M aqueous sodium hydroxide (33.8 ml) was added slowly to a solution of Intermediate B72 (7.01 g) in dioxan (150 ml). The mixture was stired for 2.5 h at room temperature, then the dioxan was evaporated, water added, and the mixture acidified with aqueous sodium bisulfate. The precipitate was filtered off, washed with water and dried to obtain the desired product (6.31 g). $^1$H-NMR (d$_6$-DMSO) δ 3.59 (2H, s), 4.41 (2H, s), 4.67 (2H, s), 7.11 (2H, m), 7.45 (2H, m), 7.72 (1H, s), 8.70 (2H, s) 9.03 (1H, s), 13.55 (1H, bs); MS (APCI−) M−1=385, $C_{18}H_{15}FN_4O_3S$ requires 386. MPt 206–207° C.

Intermediate B74—1-Ethoxycarbonylmethyl-2-(4-fluorobenzyl)thio-5-(2-oxopyrimid-5-yl-methyl)pyrimidin-4-one

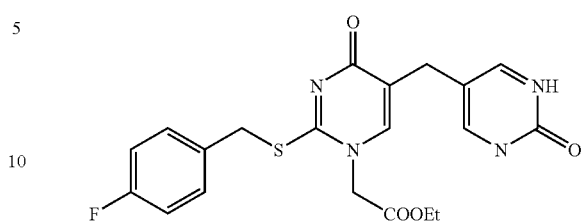

Prepared from Intermediate B86 by the method of Example 21, except using only 2 equivalents of B-bromocatecholborane. $^1$H-NMR (d6-DMSO) δ 1.28 (3H, t), 4.26 (4H, q), 4.53 (2H, s), 4.90 (2H, s), 7.26 (2H, m), 7.57 (2H, m), 7.69 1H, s), 8.25 (2H, br. s); MS (APCI+) found (M+1)=431; $C_{20}H_{19}FN_4O_4S$ requires 430.

Intermediate B75—1-Ethoxycarbonylmethyl-2-(4-fluorobenzyl)thio-5-(1-ethyl-2-oxopyrimid-5-ylmethyl)pyrimidin-4-one

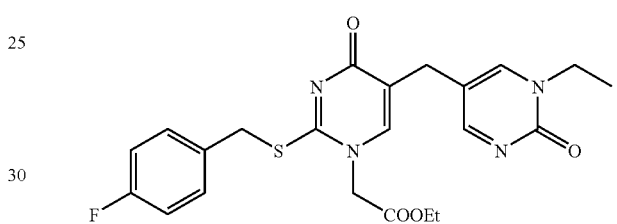

To a solution of Intermediate B74 (3.1 g) in dry dimethylformamide (40 ml) under argon was added ethyl iodide (1.4 g) and anhydrous potassium carbonate (2.5 g). The mixture was stirred at room temperature for 20 h and the solvent removed in vacuo. The residue was partitioned between ethyl acetate and water. The organic layer was washed with brine and added in equal portions to three 10 g silica cartridges. Elution of each column with EtOAc to 18% MeOH:EtOAc and combining appropriate fractions gave the title compound (1.5 g). $^1$H-NMR (CDCl3) δ 1.27t1.39t), 3.46 (2H,s), 3.94 (2H,q), 4.25 (2H,q), 4.48 (2H,s), 4.57 (2H,s), 6.9–7.15 (2H,m), 7.21 (1H,s), 7.3–7.4 (2H,m), 7.9 (1H,m), 8.4 (1H,m), MS (APCI+) found (M+1)=459; $C_{22}H_{23}FN_4O_4S$ requires 458.

The following intermediates were prepared by the method of intermediate B70:

| No. | Precursors | Structure | Name |
|---|---|---|---|
| B76 | Int. B57 | ![structure] | 1-(tert-Butoxycarbonylmethyl)-2-(3,4-difluorobenzyl)thio-5-(2-methoxypyrimid-5-ylmethyl)pyrimidin-4-one |

-continued

| No. | Precursors | Structure | Name |
|---|---|---|---|
| B77 | Int. B58 | 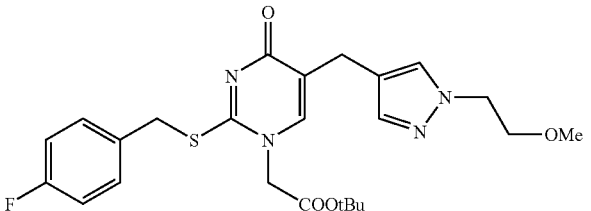 | 1-(tert-Butoxycarbonylmethyl)-2-(4-fluoro-benzylthio)-5-((1-(2-methoxyethyl)pyrazol-4-yl)methyl)pyrimidin-4-one |
| B78 | Int. B60 | 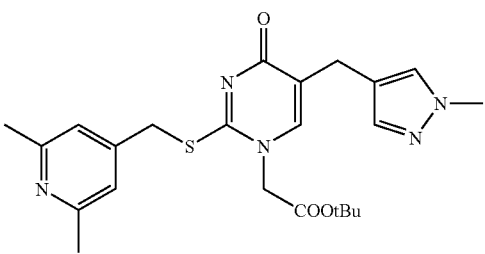 | 1-(tert-Butoxycarbonylmethyl)-2-(2,6-dimethylpyrid-4-ylmethylthio)-5-((1-methyl-pyrazol-4-yl)methyl)pyrimidin-4-one |
| B79 | Int. B64 | 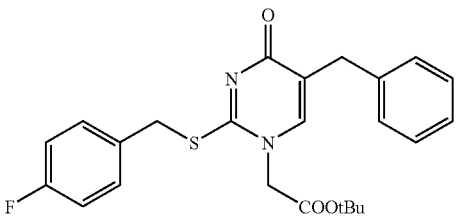 | 1-(tert-Butoxycarbonylmethyl)-2-(4-fluoro-benzylthio)-5-benzylpyrimidin-4-one |
| B80 | Int. B65 | 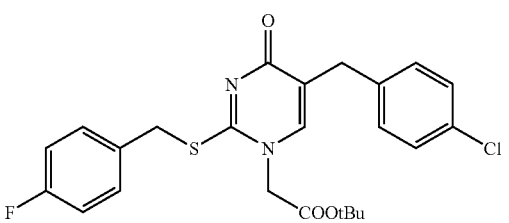 | 1-(tert-Butoxycarbonylmethyl)-2-(4-fluoro-benzylthio)-5-(4-chlorobenzyl)pyrimidin-4-one |
| B81 | Int. B59 | 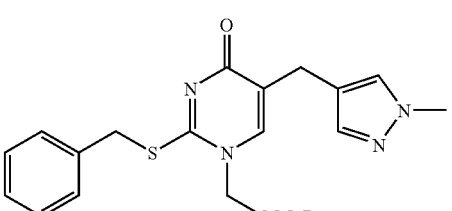 | 1-(tert-Butoxycarbonylmethyl)-2-benzyl-thio-5-((1-methylpyrazol-4-yl)methyl)-pyrimidin-4-one |
| B82 | Int. B66 | 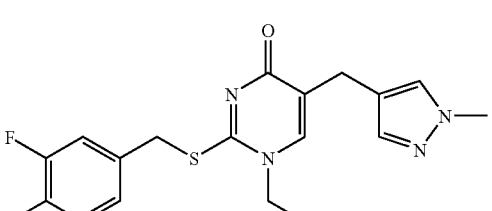 | 1-(tert-Butoxycarbonylmethyl)-2-(3,4-difluorobenzylthio)-5-((1-methylpyrazol-4-yl)methyl)pyrimidin-4-one |

The following intermediates were prepared by the method of intermediate B72:

| No. | Precursors | Structure | Name |
|---|---|---|---|
| B84 | Int. B61 | 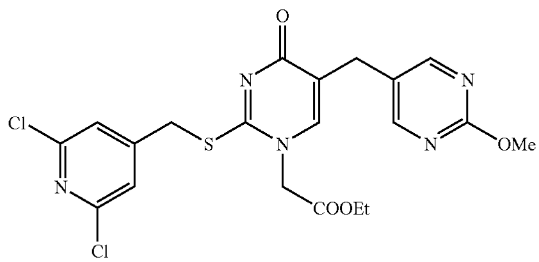 | 1-(Ethoxycarbonylmethyl)-2-(2,6-dichloro-pyrid-4-ylmethylthio)-5-(2-methoxypyrimid-5-ylmethyl)pyrimidin-4-one |
| B85 | Int. B54 | 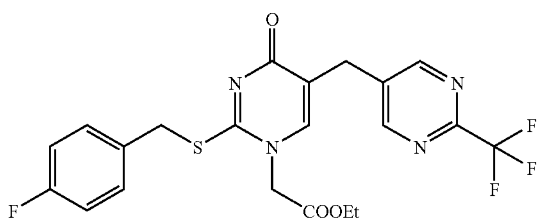 | 1-((Ethoxycarbonylmethyl)-2-(4-fluoro-benzylthio)-5-(2-trifluoromethylpyrimid-5-ylmethyl)pyrimidin-4-one |
| B86 | Int. B53 | 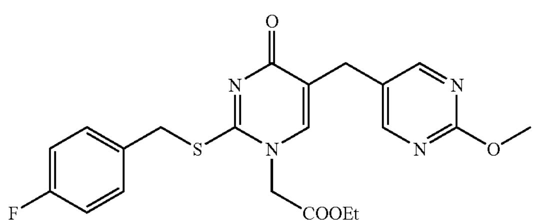 | 1-(Ethoxycarbonylmethyl)-2-(4-fluoro-benzyl)thio-5-(2-methoxypyrimid-5-yl-methyl)pyrimidin-4-one |
| B87 | Int. B55 | 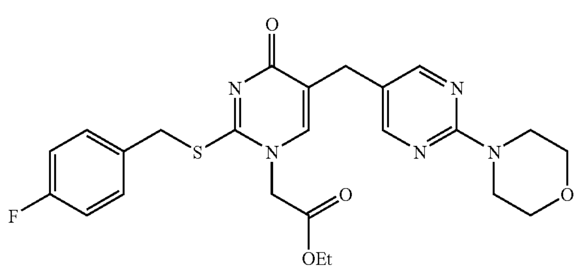 | 1-(Ethoxycarbonylmethyl)-2-(4-fluoro-benzyl)thio-5-(2-(4-morpholino)pyrimid-5-ylmethyl)pyrimidin-4-one |
| B88 | Int. B56 | 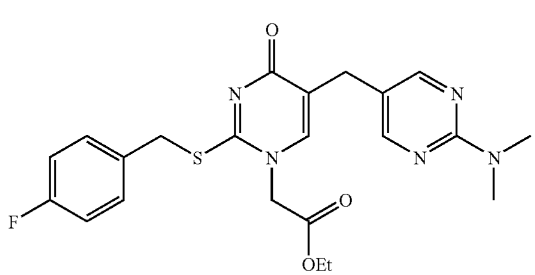 | 1-(Ethoxycarbonylmethyl)-2-(4-fluoro-benzyl)thio-5-(2-dimethylaminopyrimid-5-ylmethyl)pyrimidin-4-one |

The following intermediates were prepared by the method of intermediated B71:

| No. | Precursors | Structure | Name |
|---|---|---|---|
| B89 | Int. B81 | 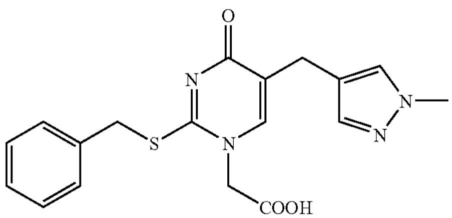 | 1-(Carboxymethyl)-2-benzylthio-5-(1-methylpyrazol-4-ylmethyl)pyrimidin-4-one |
| B90 | Int. B76 | 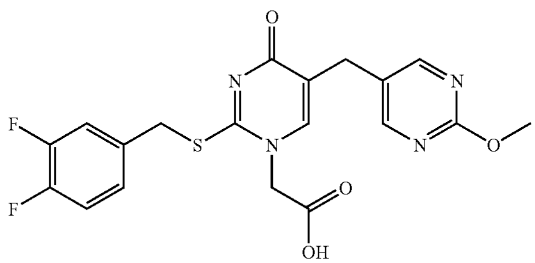 | 1-(Carboxymethyl)-2-(3,4-difluorobenzyl)-thio-5-(2-methoxypyrimid-5-ylmethyl)-pyrimidin-4-one |
| B91 | Int. B82 | 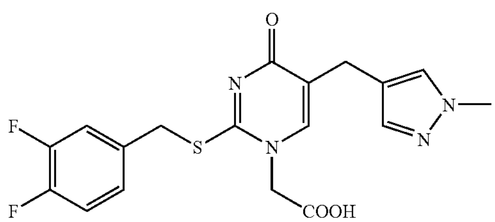 | 1-(Carboxymethyl)-2-(3,4-difluorobenzyl)-thio-5-(1-methylpyrazol-4-ylmethyl)-pyrimidin-4-one |
| B92 | Int. B78 | 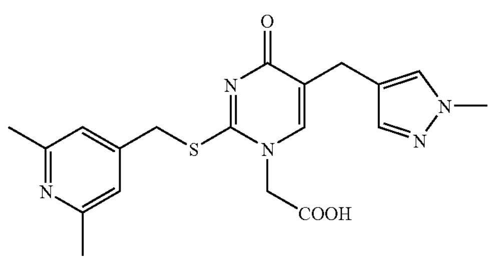 | 1-(Carboxymethyl)-2-(2,6-dimethylpyrimid-4-ylmethylthio)-5-((1-methylpyrazol-4-yl)-methyl)pyrimidin-4-one |
| B93 | Int. B79 | 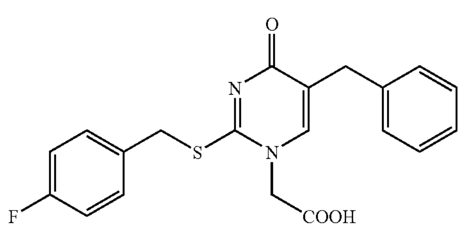 | 1-Carboxymethyl-2-(4-fluorobenzylthio)-5-benzylpyrimidin-4-one |
| B94 | Int. B80 | 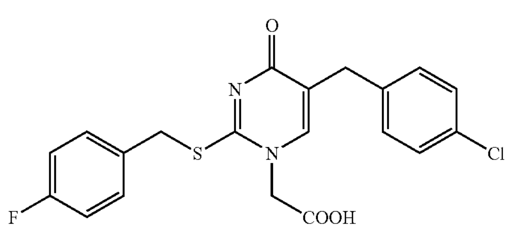 | 1-Carboxymethyl-2-(4-fluorobenzylthio)-5-(4-chlorobenzyl)pyrimidin-4-one |

-continued

| No. | Precursors | Structure | Name |
|---|---|---|---|
| B104 | Int. B77 | 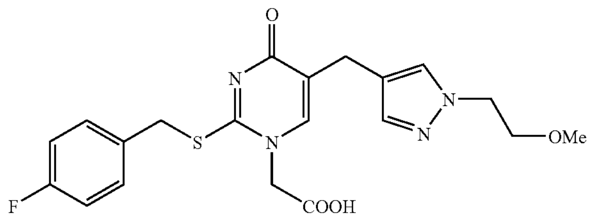 | 1-(Carboxymethyl)-2-(4-fluorobenzylthio)-5-((1-(2-methoxyethyl)pyrazol-4-yl)methyl)pyrimidin-4-one |

The following intermediates were prepared by the method of intermediate B73:

| No. | Precursors | Structure | Name |
|---|---|---|---|
| B96 | Int. B51 | 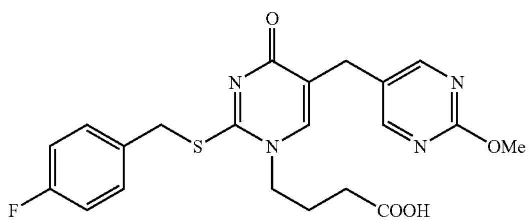 | 1-(3-Carboxyprop-1-yl)-2-(4-fluorobenzyl)thio-5-(2-methoxypyrimid-5-ylmethyl)-pyrimidin-4-one |
| B97 | Int. B67 | 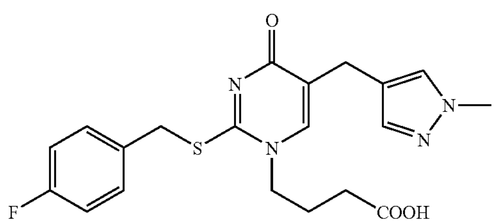 | 1-(3-Carboxyprop-1-yl)-2-(4-fluorobenzyl)thio-5-(2-methylpyrazol-4-ylmethyl)-pyrimidin-4-one |
| B98 | Int. B85 | 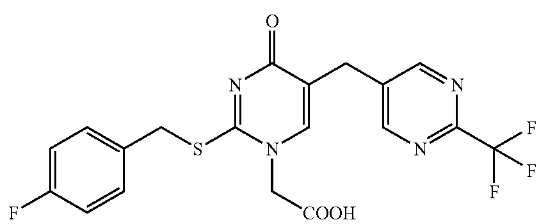 | 1-Carboxymethyl-2-(4-fluorobenzylthio)-5-((2-trifluoromethylpyrimid-5-yl)methyl)pyrimidin-4-one |
| B99 | Int. B68 | 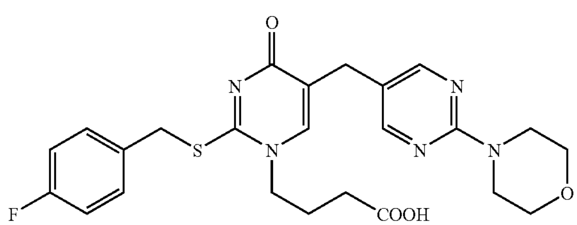 | 1-(3-Carboxyprop-1-yl)-2-(4-fluorobenzyl)thio-5-(2-(4-morpholino)pyrimid-5-yl-methyl)pyrimidin-4-one |
| B100 | Int. B75 | 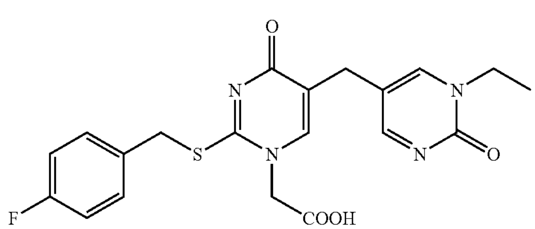 | 1-Carboxymethyl-2-(4-fluorobenzyl)thio-5-(1-ethyl-2-oxopyrimid-5-yl-methyl)pyrimidin-4-one |

| No. | Precursors | Structure | Name |
|---|---|---|---|
| B101 | Int. B87 | 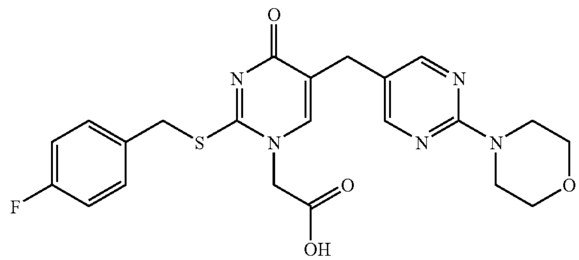 | 1-(Carboxymethyl)-2-(4-fluorobenzyl)thio-5-(2-(4-morpholino)pyrimid-5-yl-methyl)pyrimidin-4-one |
| B102 | Int. B88 | 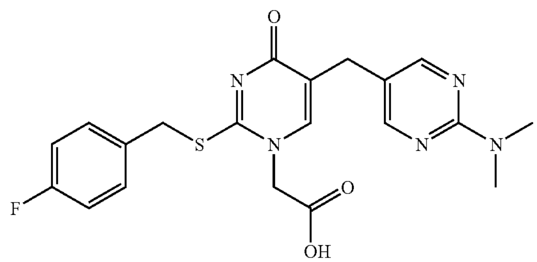 | 1-(Carboxymethyl)-2-(4-fluorobenzyl)thio-5-(2-dimethylaminopyrimid-5-yl-methyl)pyrimidin-4-one |
| B103 | Int. B84 | 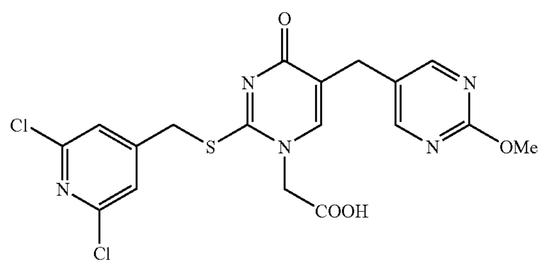 | 1-(Carboxymethyl)-2-(2,6-dichloropyrid-4-ylmethylthio)-5-(2-methoxypyrimid-5-yl methyl)pyrimidin-4-one |
| B104 | Int. B86 | 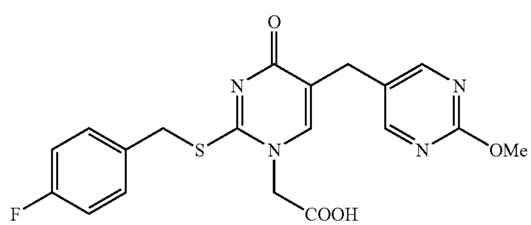 | 1-Carboxymethyl-2-(4-Fluorobenzylthio)-5-(2-methoxypyrimid-5-ylmethyl)pyrimidin-4-one |

Example 1

1-(N-Methyl-N-(4-(4-chlorophenyl)benzyl)aminocarbonylmethyl)-2-(4-fluorobenzyl)thio-5-(1-methylpyrazol-4-ylmethyl)pyrimidin-4-one

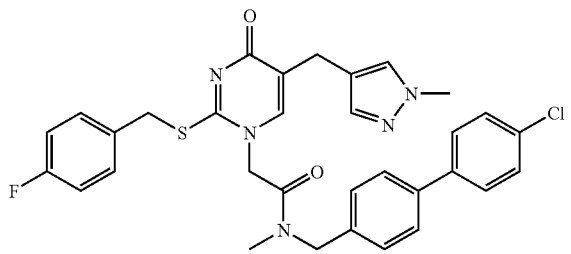

A mixture of Intermediate A2 (0.27 g, 1 equiv), Intermediate B71 (0.45 g, 1 equiv), hydroxybenzotriazole (0.018 g, 0.1 equiv), 1-(3-dimethylaminopropyl)-3-ethylcarbodiimide (0.25 g, 1.1 equiv) and dichloromethane (15 ml) was stirred at room temperature overnight, then diluted with dichloromethane and washed with aqueous sodium bicarbonate. The organic layer was applied directly to a 10 g silica cartridge, which was eluted with 0–10% methanol in ethyl acetate. Product fractions were evaporated to an oil, which was triturated with ether to obtain a white solid (0.39 g). $^1$H-NMR (d$_6$-DMSO) δ 2.95 and 3.08 (3H, 2Xs), 3.61(2H, m), 3.86 (3H, m), 4.46–4.61 (6H, m), 6.74 and 6.80 (1H, 2Xs), 6.91–6.99 (2H, m), 7.21–7.49 (12H, m); MS (APCI+) found (M+1)=602; $C_{32}H_{29}ClFN_5O_2S$ requires 601.

Example 2

1-(N-Methyl-N-(4-(4-trifluoromethylphenyl)benzyl)
aminocarbonylmethyl)-2-(4-fluorobenzyl)thio-5-(1-
methylpyrazol-4-ylmethyl)pyrimidin-4-one

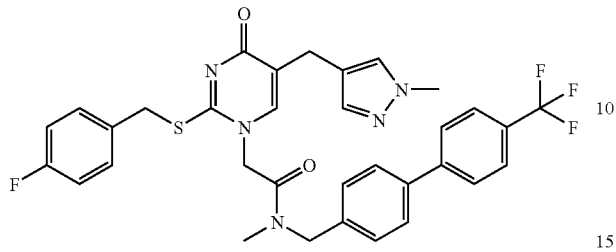

Prepared from Intermediates A45 and B71 by the method of Example 1. $^1$H-NMR (DMSO) δ 2.96 (3H,s), 3.39 (2H, m), 3.77 (3H,s), 4.43 (2H, s), 4.57 (2H,s), 4.97 (2H,s), 7.12 (3H,m), 7.25 (1H,s), 7.34–7.48 (6H, m), 7.62–6.70 (2H,m), 8.84 (4H,m).; MS (APCI+) found (M+1)=636; $C_{33}H_{29}F_4N_5O_2S$ requires 635.

Example 3

1-(N-(2-Dimethylaminoethyl)-N-(4-(4-chlorophenyl)
benzyl)aminocarbonylmethyl)-2-(4-fluorobenzyl)
thio-5-(1-methylpyrazol-4-ylmethyl)pyrimidin-4-one
hydrochloride

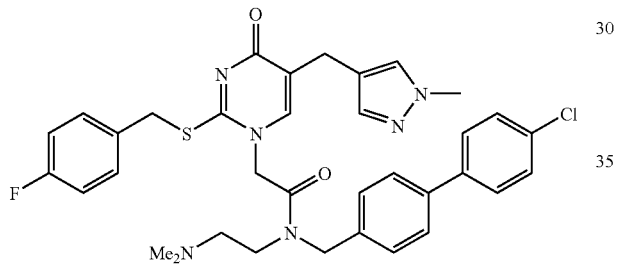

Prepared from Intermediates A61 and B71 by the method of Example 1. $^1$H-NMR (CDCl$_3$) δ 2.95 (3H, s), 2.96(3H, s), 3.19 (2H, m), 3.58 (2H, s), 3.87 (3H, s), 3.91 (2H, m), 4.42 (2H, s), 4.68 (2H, s), 4.99 (2H, s), 6.88–6.93 (2H, m), 7.25–7.29 (6H, m), 7.36–7.45 (6H, m) 7.62 (1H, s); MS (APCI+) found (M+1)=659; $C_{35}H_{36}ClFN_6O_2S$ requires 658.

Example 4

1-(N-Methyl-N-(4-(4chlorophenyl)benzyl)aminocar-
bonylmethyl)-2-(4-fluorobenzyl)thio-5-(2-(4-mor-
pholino)pyrimid-5-ylmethyl)pyrimidin-4-one

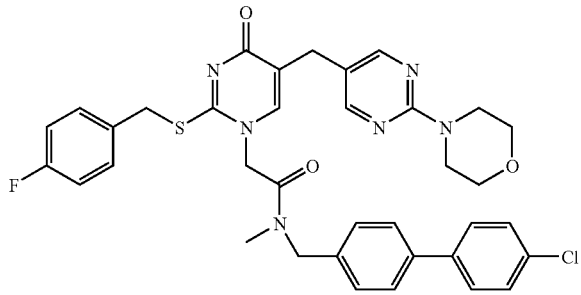

A solution of Intermediate A7 (0.23 g, 1 equiv), Intermediate B55 (0.27 g, 1 equiv) and diisopropyl-ethylamine (0.10 g, 1.2 equiv) in dry dichloromethane (6 ml) was stirred at room temperature under argon for 20 h, then diluted with more dichloromethane and washed successively with water and aqueous ammonium chloride. Drying and evaporation of the organic phase, followed by chromatography (silica, 0–5% methanol in ethyl acetate) gave the desired product as a pale solid (0.19 g). $^1$H-NMR (DMSO-d$_6$) δ: 2.95 (d, 3H), 3.42 (d, 2H), 3.64 (s, 8H), 4.40 (d, 2H), 4.60 (d, 2H), 4.95 (d, 2H), 7.1 (m, 2H), 7.30 (d, 2H), 7.35–7.6 (m, 6H), 7.65 (m, 3H), 8.30 (s, 2H). MS (APCI+) Found (M+1)=685/687; $C_{36}H_{34}ClFN_6O_3S$ requires 685.

Example 5

1-(N-(2-(dimethylamino)ethyl)-N-(4-(4-trifluorom-
ethylphenyl)benzyl)aminocarbonylmethyl)-2-(4-
fluorobenzyl)thio-5-(1-methyl-4-pyrazolylmethyl)
pyrimidin-4-one hydrochloride

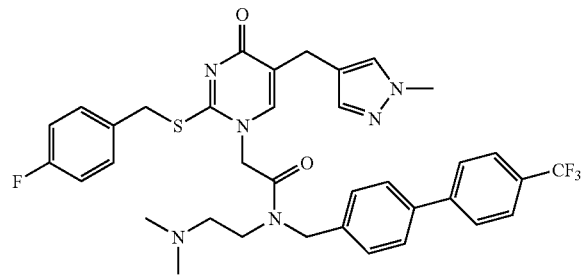

Prepared from Intermediates A72 and B71 by the method of Example 1. $^1$H-NMR (CDCl$_3$) δ 2.98 (3H,s), 2.99 (3H,s), 3.20 (2H,m), 3.60 (2H,s), 3.93 (5H,m), 4.42 (3H,s), 4.69 (2H,s), 5.00 (2H,s), 6.89 (2H,m), 7.2–7.3 (4H,m), 7.47 (4H, m), 7.55 (2H,d), 7.70 (3H,m), 11.7 (1H, br s); MS (APCI+) found (M+1)=693; $C_{36}H_{36}F_4N_6O_2S$ requires 692.

Example 6

1-(N-(2-(diethylamino)ethyl)-N-(4-(4-chlorophenyl)
benzyl)aminocarbonylmethyl)-2-(4-fluorobenzyl)
thio-5-(1-methyl-4-pyrazolylmethyl)pyrimidin-4-one

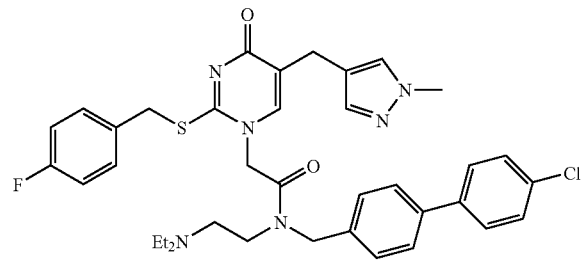

A mixture of Intermediate A3 (82.7 g, 1 equiv), B71 (101.3 g, 1 equiv), hydroxybenzotriazole (39.9 g, 1 equiv), 1-(3-dimethylaminopropyl)-3-ethylcarbodiimide (100.0 g, 2 equiv) and dichloromethane (1200 ml) was stirred under argon at room temperature overnight, then aqueous sodium bicarbonate was added slowly with stirring. The organic layer was separated, the aqueous layer extracted twice more with dichloromethane, and the combined organic extracts dried over potassium carbonate and evaporated to a brown oil. Trituration with ether gave a solid, which was filtered off and purified by chromatography on silica, eluting with methanol/dichloromethane then with methanolic ammonia/dichloromethane. Product fractions were evaporated to a yellow foam (98 g). $^1$H-NMR (CDCl$_3$, rotamer mixture) δ 0.9–1.0 (6H,m) δ 2.4–2.6 (6H,m), 3.23/3.52 (4H,2x t), 3.58/3.61 (4H, 2x s), 3.85 (3H,s), 4.46/4.53/4.64/4.82 (6H, 4x s), 6.75/6.79 (1H,2x s), 6.9 (2H,m), 7.2–7.5 (12H,m); MS (APCI+) found (M+1)=687/689; $C_{37}H_{40}ClFN_6O_2S$ requires 686/688.

Example 7

1-(N-(2-(diethylamino)ethyl)-N-(4-(4-chlorophenyl) benzyl)aminocarbonylmethyl)-2-(4-fluorobenzyl) thio-5-(1-methyl-4-pyrazolylmethyl)pyrimidin-4-one hydrochloride The free base from Example 6 (8.7 g, 1 equiv) was dissolved in dichloromethane (50 ml) and 1M hydrogen chloride in ether (1 equiv) was added dropwise under argon. The mixture was evaporated to ca. half volume and sonicated to obtain a clear solution, which was transferred to a syringe and added dropwise to ether (200 ml) with vigorous stirring. The white solid was filtered off, washed with ether and dried in vacuo; yield 8.55 g. $^1$H-NMR (DMSO, ca 2:1 rotamer mixture) δ 1.14–1.24 (6H,m), 3.1 (6H, m), 3.6 (2H,m), 3.76 (3H,s), 4.38/4.45 (2H,2x s), 4.61/4.70 (2H,2x s), 4.98/5.11 (2H,2x s), 6.75/6.79 (1H,2x s), 7.1–7.7 (15H, m), 10.15/10.75 (1H,2x br s; MS (APCI+) found (M+1) =687/689; $C_{37}H_{40}ClFN_6O_2S$ requires 686/688.

Example 8

1-(N-(2-(diethylamino)ethyl)-N-(4-(4-chlorophenyl) benzyl)aminocarbonylmethyl)-2-(4-fluorobenzyl) thio-5-(1-methyl-4pyrazolylmethyl)pyrimidin-4-one bitartrate A solution of L-tartaric acid (0.75 g, 1 equiv) in 2-propanol (12 ml) was added to a solution of the free base from Example 6 (3.43 g, 1 equiv) in 2-propanol (25 ml) with stirring. The mixture was evaporated to ca. one third volume, diluted with ether, then the solid was filtered off, washed with ether and dried in vacuo; yield 3.87 g. $^1$H-NMR (DMSO, ca. 60:40 rotamer mixture) δ 0.9–1.1 (6H,m), 2.5–2.8 (4H,m), 3.2–3.4 (6H,m), 3.76 (3H,s), 4.20 (2H,s), 4.39/4.43 (2H,2x s), 4.60/4.67 (2H,2x s), 4.92/5.08 (2H,2x s), 7.1–7.7 (15H,m); MS (APCI+) found (M+1)=687/689; $C_{37}H_{40}ClFN_6O_2S$ requires 686/688.

Example 9

1-(N-(2-(diethylamino)ethyl)-N-(4-(4-chlorophenyl) benzyl)aminocarbonylmethyl)-2-(4-fluorobenzyl) thio-5-(1-methyl-4-pyrazolylmethyl)pyrimidin-4-one maleate A solution of maleic acid (0.58 g, 1 equiv) in methanol (10 ml) was added to a solution of the free base from Example 6 (3.43 g, 1 equiv) in methanol (10 ml) with stirring. The mixture was evaporated to ca. half volume, diluted with ether, then the supernatent decanted off. The oil was triturated with ether to obtain a solid, which was filtered off, washed with ether and dried in vacuo; yield 3.69 g. $^1$H-NMR (DMSO, ca. 3:1 rotamer mixture) essentially similar to Example 7, plus δ 2.33 (3H,s); MS (APCI+) found (M+1) =687/689; $C_{37}H_{40}ClFN_6O_2S$ requires 686/688.

Example 10

1-(N-(2-(diethylamino)ethyl)-N-(4-(4-chlorophenyl) benzyl)aminocarbonylmethyl)-2-(4-fluorobenzyl) thio-5-(1-methyl-4-pyrazolylmethyl)pyrimidin-4-one mesylate Prepared by the method of example 9, using methanesulfonic acid (0.32 ml, 1 equiv) in place of maleic acid; yield 3.59 g. $^1$H-NMR (DMSO, ca. 3:1 rotamer mixture) essentially similar to Example 7, plus δ 6.03 (2H,s); MS (APCI+) found (M+1)=687/689; $C_{37}H_{40}ClFN_6O_2S$ requires 686/688.

Example 11

1-(N-(2-(diethylamino)ethyl)-N-(4-(4-chlorophenyl) benzyl)aminocarbonylmethyl)-2-(4-fluorobenzyl) thio-5-(1-methyl-4-pyrazolylmethyl)pyrimidin-4-one taurocholate Prepared by the method of example 9, using taurocholic acid (2.57 g, 1 equiv) in place of maleic acid; yield 5.56 g. $^1$H-NMR (DMSO, ca. 3:1 rotamer mixture) essentially similar to Example 7, plus (inter alia) δ 0.58 (3H,s), 0.81 (3H,s), 0.91 (3H,d), 1.14 (3H,s); MS (APCI+) found (M+1)=687/689; $C_{37}H_{40}ClFN_6O_2S$ requires 686/688.

Example 12

1-(N-(2-(diethylamino)ethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4-one

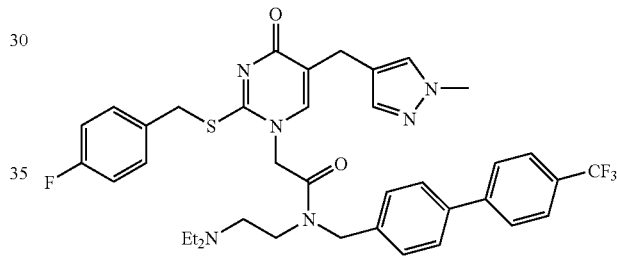

Prepared from Intermediates A73 and B71 by the method of Example 1. $^1$H-NMR (CDCl$_3$, rotamer mixture) δ 0.9–1.0 (6H,m) δ 2.4–2.6 (6H,m), 3.24/3.4–3.6 (4H,2x m), 3.85 (3H,s), 4.46/4.53/4.66/4.83 (6H,4x s), 6.75/6.8 (1H,2x s), 6.9–7.0 (2H,m), 7.3–7.7 (12H,m); MS (APCI+) found (M+1)=721; $C_{38}H_{40}F_4N_6O_2S$ requires 720.

Example 13

1-(N-(2-(diethylamino)ethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4one hydrochloride The free base from Example 12 (0.75 g, 1 equiv) was dissolved in dichloromethane (5 ml) and 1M hydrogen chloride in ether (1 equiv) was added dropwise under argon, then excess ether was added with vigorous stirring. The white solid was filtered off, washed with ether and dried in vacuo; yield 0.73 g. $^1$H-NMR (DMSO, ca. 3:1 rotamer mixture) δ 1.1–1.2 (6H,m), 3.1 (6H, m), 3.37 (2H+H$_2$O,m), 3.66 (2H,m), 3.76 (3H,s), 4.37/4.45 (2H,2x s), 4.63/4.72 (2H,2x s), 4.97/5.12 (2H,2x s), 7.1 (2H,m), 7.24/7.26 (1H,2x s), 7.4–7.5 (6H,m),6.62/6.71 (2H, 2x d), 7.84 (4H,m), 10.1/10.65 (1H,2x br s); MS (APCI+) found (M+1)=721; $C_{38}H_{40}F_4N_6O_2S$ requires 720.

Example 14

1-(N-(2-(diethylamino)ethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4-one bitartrate Prepared from the free base of Example 12 by the method of Example 8. $^1$H-NMR (DMSO, ca. 60:40 rotamer mixture) δ 0.9–1.0 (6H,m), 2.5–2.8 (4H,m), 3.2–3.5 (6H,m), 3.76 (3H,s), 4.19 (2H,s), 4.38/4.43 (2H,2x s), 4.62/4.69 (2H,2x s), 4.92/5.10 (2H,2x s), 7.0–7.5 (12H,m), 7.6/7.7 (1H, 2x d), 7.84 (2H,m); MS (APCI+) found (M+1)=721; $C_{38}H_{40}F_4N_6O_2S$ requires 720.

Example 15

1-(N-(2-(diethylamino)ethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4-one citrate Free base from Example 12 (0.69 g, 1 equiv) was added to acetone (10 ml) followed by citric acid (0.20 g, 1 equiv). The mixture was warmed to dissolve the solids then allowed to cool, whereupon the solids were filtered off and dried in vacuo; yield 0.80 g, 90%, m.p. 130–133° C. $^1$H-NMR (d6-DMSO, ca. 1:1 rotamer mixture) essentially similar to Example 14, plus δ 2.61 (2H,d); MS (APCI+) found (M+1) =721; $C_{38}H_{40}F_4N_6O_2S$ requires 720.

Example 16

1-(N-(2-(diethylamino)ethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4-one tosylate Free base from Example 12 (1.0 g, 1 equiv) and tosic acid (0.26 g, 1 equiv) were dissolved in acetone (20 ml) at room temperature, then isopropyl acetate (60 ml) was added with stirring. After stirring for a further 2 hours, the mixture was allowed to stand overnight then the solid was filtered off, washed with 3:1 isopropyl acetate/acetone, and dried in vacuo; yield 0.87 g, m p. 147° C. $^1$H-NMR (d6-DMSO, ca. 3:1 rotamer mixture) essentially similar to Example 13, plus (inter alia) δ 2.28 (3H,s); MS (APCI+) found (M+1)=721; $C_{38}H_{40}F_4N_6O_2S$ requires 720

Example 17

1-(N-(2-(diethylamino)ethyl)-N-(2-(4-trifluoromethylphenyl)pyrid-5-ylmethyl)aminocarbonylmethyl)-2-(4-fluorobenzyl)thio-5-(1-methyl-4-pyrazolylmethyl)pyrimidin-4-one

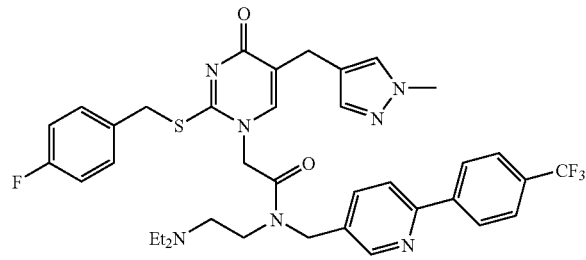

A mixture of Intermediate A106 (0.523 g, 1 equiv), Intermediate B71 (0.473 g, 1 equiv), HATU (0.55 g, 1.2 equiv), diisopropylethylamine (0.622 ml, 2.4 equiv) and dichloromethane (20 ml) was stirred under argon at room temperature overnight, then washed with aqueous ammonium chloride and aqueous sodium bicarbonate. The organic layer was dried and evaporated, and the free-base product isolated by chromatography (silica, 3–8% methanol in dichloromethane) as a pale foam (0.39 g). $^1$H-NMR (CDCl$_3$, major rotamer) δ 0.94 (6H,t), 2.47 (4H,q), 2.58 (2H,m), 3.26 (2H,m), 3.61 (2H,s), 3.85 (3H,s), 4.52 (2H,s), 4.66 (2H,s), 4.82 (2H,s), 6.78 (1H,s), 6.98 (2H,m), 7.3–7.4 (4H,m), 7.6–7.8 (2H,m), 8.08 (2H,m), 8.57 (1H,m); MS (APCI+) found (M+1)=722; $C_{37}H_{39}F_4N_7O_2S$ requires 721.

Example 18

1-(N-(2-(Diethylamino)ethyl)-N-(2-(4-trifluoromethylphenyl)pyrid-5-ylmethyl)aminocarbonylmethyl)-2-(4-fluorobenzyl)thio-5-(1-methyl-4-pyrazolylmethyl) pyrimidin-4-one hydrochloride The free base from Example 17 (0.373 g, 1 equiv) was dissolved in dichloromethane (10 ml), and a solution of hydrogen chloride in ether (0.517 ml, 1.0M solution, 1 equiv) was added dropwise with stirring. The solvent was removed in vacuo, and the residue triturated with ether to obtain a white solid (0.362 g). $^1$H-NMR (DMSO, ca. 60:40 rotamer mixture) δ 1.1–1.3 (6H,m), 3.77 (3H,s), 4.38/4.43 (2H,s), 4.65/4.76 (2H,s), 5.00/5.08 (2H,s), 7.10 (2H,m), 7.25 (1H,m), 7.3–7.5 (4H,m) 7.78 (1H,m), 7.87 (2H,d), 7.97/8.06 (1H,d), 8.28 (2H,d), 8.61/8.70 (1H,m); MS (APCI+) found (M+1)=722; $C_{37}H_{39}F_4N_7O_2S$ requires 721.

Example 19

1-(N-(2-(Diethylamino)ethyl)-N-(2-(4-trifluoromethylphenyl)pyrid-5-ylmethyl)aminocarbonylmethyl)-2-(4-fluorobenzyl)thio-5-(1-methyl-4-pyrazolylmethyl) pyrimidin-4one bitartrate Prepared from the free base of Example 17 by the method of Example 8. $^1$H-NMR (DMSO, ca. 60:40 rotamer mixture) δ 0.88–1.05 (6H,m), 3.76 (3H,s), 4.39/4.42 (2H,s), 4.65/4.74 (2H,s), 4.97/5.10 (2H,s), 7.11 (2H,m), 7.25 (1H,m), 7.3–7.5 (4H,m), 7.78 (1H,m), 7.87 (2H,m), 7.98/8.07 (1H,d), 8.28 (2H,d), 8.61/8.70 (1H,m); MS (APCI+) found (M+1)=722; $C_{37}H_{39}F_4N_7O_2S$ requires 721.

Example 20

1-(N-(2-(1-Piperidino)ethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4-one bitartrate

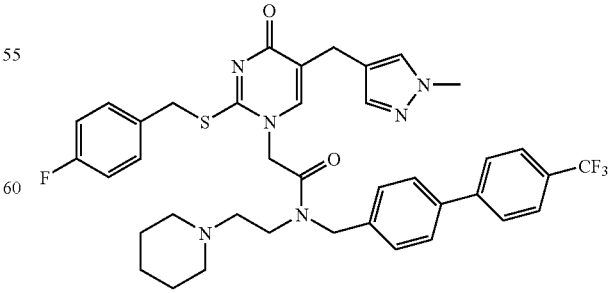

The free base was prepared from Intermediates A108 and B71 by the method of Example 1, then converted to bitartrate salt by the method of Example 8. ¹H-NMR (DMSO, ca 60:40 rotamer mixture) δ 1.3–1.6 (6H,m) δ 2.3–2.7 (6H,m), 3.3–3.6 (4H,m), 3.77 (3H,s), 4.22 (2H,s), 4.37/4.44 (2H,2x s), 4.62/4.69 (2H,2x s), 4.88/5.08 (2H,2x s), 7.1–7.5 (12H, m), 7.6/7.7 (1H, 2x d), 7.83 (2H,m); MS (APCI+) found (M+1)=733; $C_{39}H_{40}F_4N_6O_2S$ requires 732.

Example 21

1-(N-(Carboxymethyl)-N-(4-(4-trifluoromethylphenyl)benzyl)aminocarbonylmethyl)-2-(4-fluorobenzyl)thio-5-(1-methyl-4-pyrazolylmethyl)pyrimidin-4-one sodium salt

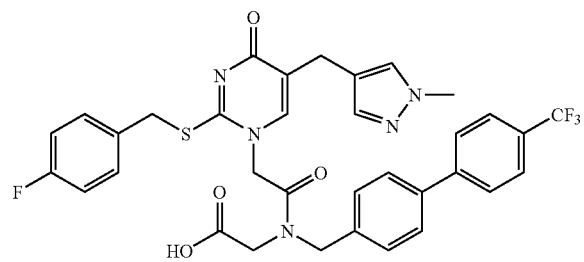

Example 102 (130 mg) was added to a solution of sodium bicarbonate (16 mg) in water (4 ml) and stirred for 1 hour at room temperature. A small proportion of methanol was added to obtain a clear solution on warming and sonication. Filtration and lyophilisation gave the desired sodium salt as a white solid. ¹H-NMR (DMSO) δ 3.49 (2H,s), 3.76 (3H,s), 4.42 (2H,s), 4.85 (2H,s), 7.14 (2H,m), 7.26 (1H,s), 7.36 (3H,m), 7.49 (3H,m), 7.60 (2H,m), 7.84 (4H,m); MS (APCI−) found (M+1)=678; $C_{34}H_{29}F_4N_5O_4S$ requires 679.

Example 22

1-(N-(2-aminoethyl)-N-(4-(4chlorophenyl)benzyl)aminocarbonylmethyl)-2-(4-fluorobenzyl)thio-5-(1-methyl-4-pyrazolylmethyl)pyrimidin-4-neohydrochloride

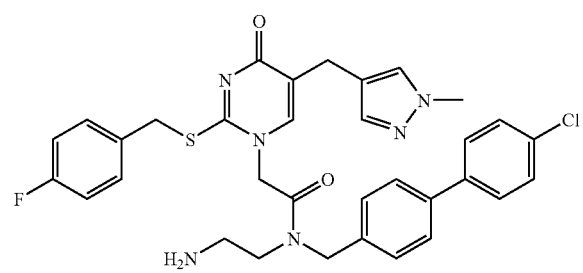

The Boc-protected product was prepared from Intermediates A84 and B71 by the method of Example 1, then deprotected by suspending in dioxan and treating with excess hydrogen chloride (4M solution in dioxan). After stirring for 1 hour, excess ether was added and stirring continued until a fine white solid was obtained. This was filtered off, washed with ether and dried to obtain the crude product, which was purified by chromatography (silica, 10–20% methanol in dichloromethane). ¹H-NMR (DMSO, ca. 60:40 rotamer mixture) δ 2.97/3.04 (2H,m) δ 3.37 (2H,m), 3.55 (2H,m), 3.77 (3H,s), 4.36/4.45 (2H,2x s), 4.60 4.67 (2H,2x s), 4.93/5.09 (2H,2x s), 7.0–7.7 (15H,m), 8.05/8.20 (2H,2x br s); MS (APCI+) found (M+1)=733; $C_{39}H_{40}F_4N_6O_2S$ requires 732.

Example 23

1-(N-Methyl-N-(4-(4clorophenyl)benzyl)aminocarbonylmethyl)-2-(4-fluorobenzyl)thio-5-(2-oxopyrimid-5-ylmethyl)pyrimidin-4-one

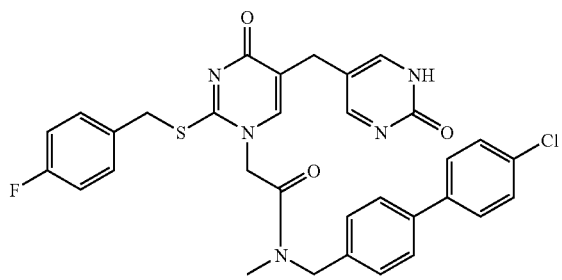

A mixture of Example 121 (0.73 g, 1.2 mmol), B-bromocatecholborane (1.01 g, 5.1 mmol) and dry dichloromethane (20 ml) was stirred under argon at room temperature overnight, giving a clear orange solution. Water was added and stirring continued for 30 min, then the organic layer was separated and applied directly to a 10 g silica cartridge, which was eluted with 0–14% methanol in dichloromethane. Product fractions were evaporated to obtain a pale yellow solid (0.36 g). ¹H-NMR (DMSO) δ 2.80–3.06 (3H, 2x s), 3.37 (2H, s), 4.33–4.49 (2H, 2x s), 4.50–4.72 (2H, 2x s), 4.87–5.06 (2H, m), 7.04–7.75 (13H, m), 8.19 (2H, s); MS (APCI−) found (M−1)=614; $C_{32}H_{27}N_5O_3SFCl$ requires 615.

The following Examples were made either by the method of Example 1 (EDC coupling) or Example 15 (HATU coupling); where indicated, the salts were subsequently prepared by the methods of Examples 7–8 as appropriate:

| Ex. No. | Precursors | Structure | Name |
|---|---|---|---|
| 30 | Int. A2<br>Int. B97 | 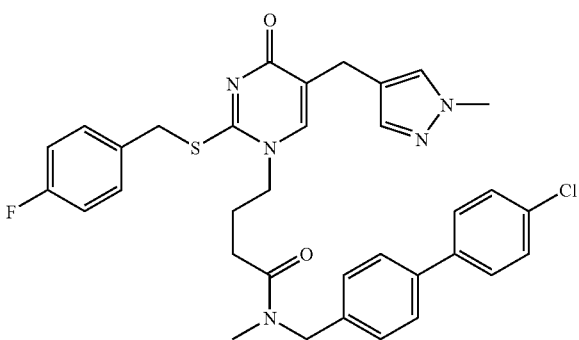 | 1-(3-(N-methyl-N-(4-(4-chlorophenyl)-benzyl)aminocarbonyl)prop-1-yl)-2-(4-fluorobenzyl)thio-5-(1-methyl-4-pyrazolylmethyl)pyrimidin-4-one |
| 31 | Int. A120<br>Int. B97 | 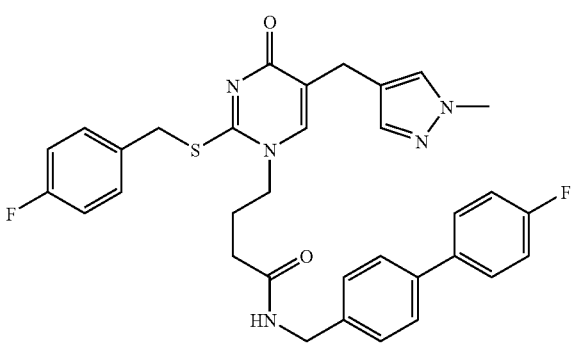 | 1-(3-(4-(4-fluorophenyl)benzylaminocarbonyl)prop-1-yl)-2-(4-fluorobenzyl)thio-5-(1-methyl-4-pyrazolylmethyl)pyrimidin-4-one |
| 32 | Int. A44<br>Int. B97 | 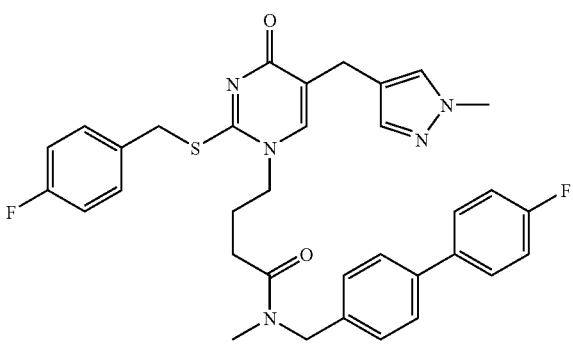 | 1-(3-(N-methyl-N-(4-(4-fluorophenyl)-benzyl)aminocarbonyl)prop-1-yl)-2-(4-fluorobenzyl)thio-5-(1-methyl-4-pyrazolylmethyl)pyrimidin-4-one |
| 33 | Int. A124<br>Int. B97 | 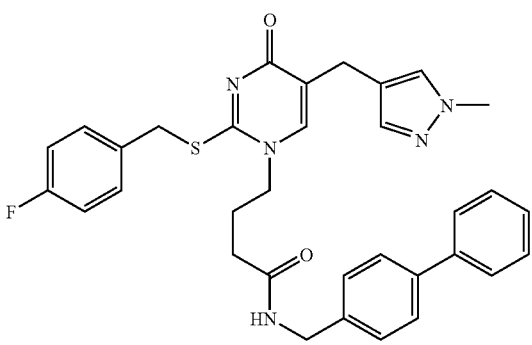 | 1-(3-(4-phenylbenzylaminocarbonyl)-prop-1-yl)-2-(4-fluorobenzyl)thio-5-(1-methyl-4-pyrazolylmethyl)pyrimidin-4-one |

-continued

| Ex. No. | Precursors | Structure | Name |
|---|---|---|---|
| 34 | Int. A6<br>Int. B99 | 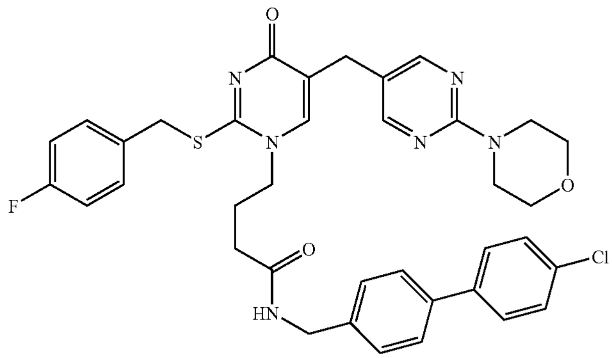 | 1-(3-(4-(4-chlorophenyl)benzylaminocarbonyl)prop-1-yl)-2-(4-fluorobenzyl)-thio-5-(2-(4-morpholino)-5-pyrimidylmethyl)pyrimidin-4-one |
| 35 | Int. A2<br>Int. B99 | 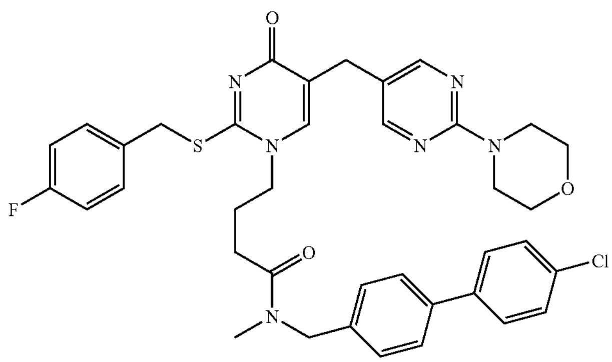 | 1-(3-(N-methyl-N-(4-(4-chlorophenyl)-benzyl)aminocarbonyl)prop-1-yl)-2-(4-fluorobenzyl)thio-5-(2-(4-morpholino)-5-pyrimidylmethyl)pyrimidin-4-one |
| 36 | Int. A6<br>Int. B96 | 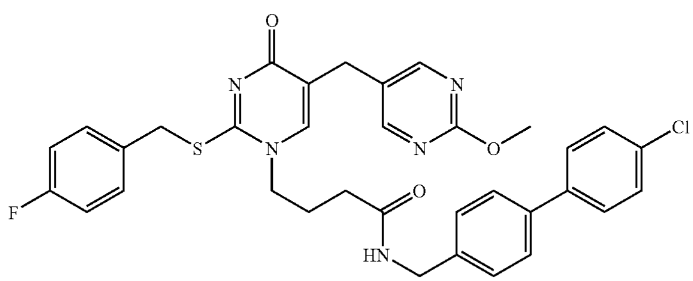 | 1-(3-(4-(4-chlorophenyl)benzylaminocarbonyl)prop-1-yl)-2-(4-fluorobenzyl)-thio-5-(2-methoxy-5-pyrimidylmethyl)-pyrimidin-4-one |
| 37 | Int. A2<br>Int. B96 | 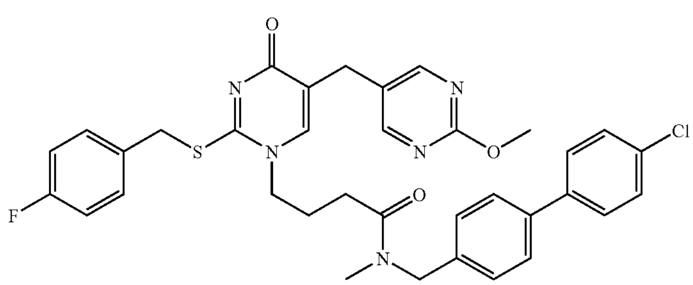 | 1-(3-(N-methyl-N-(4-(4-chlorophenyl)-benzyl)aminocarbonyl)prop-1-yl)-2-(4-fluorobenzyl)thio-5-(2-methoxy-5-pyrimidylmethyl)pyrimidin-4-one |
| 38 | Int. A120<br>Int. B96 | 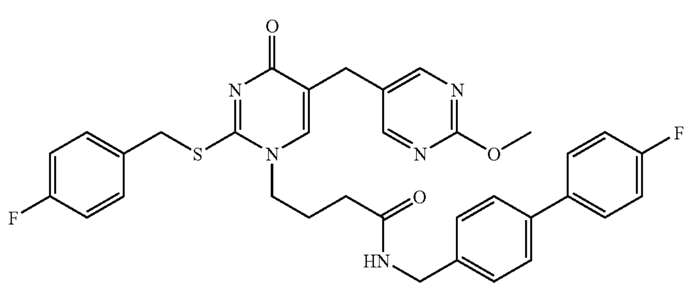 | 1-(3-(4-(4-fluorophenyl)benzylaminocarbonyl)prop-1-yl)-2-(4-fluorobenzyl)-thio-5-(2-methoxy-5-pyrimidylmethyl)-pyrimidin-4-one |

-continued

| Ex. No. | Precursors | Structure | Name |
|---|---|---|---|
| 39 | Int. A44<br>Int. B96 | 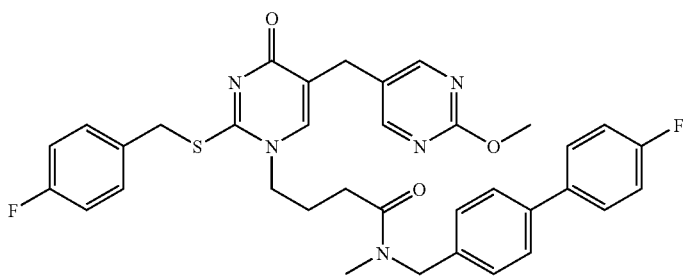 | 1-(3-(N-methyl-N-(4-(4-fluorophenyl)-benzyl)aminocarbonyl)prop-1-yl)-2-(4-fluorobenzyl)thio-5-(2-methoxy-5-pyrimidylmethyl)pyrimidin-4-one |
| 40 | Int. A124<br>Int. B96 | 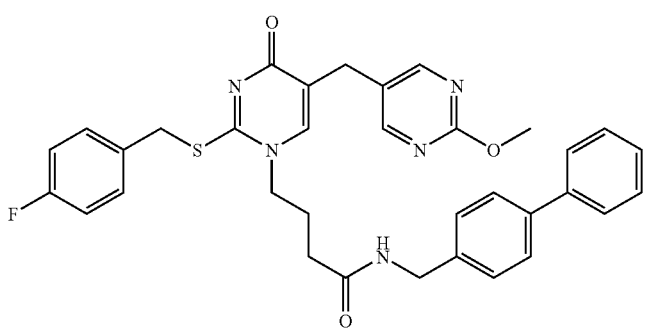 | 1-(3-(4-phenylbenzylaminocarbonyl)-prop-1-yl)-2-(4-fluorobenzyl)thio-5-(2-methoxy-5-pyrimidylmethyl)pyrimidin-4-one |
| 41 | Int. A64<br>Int. B96 | 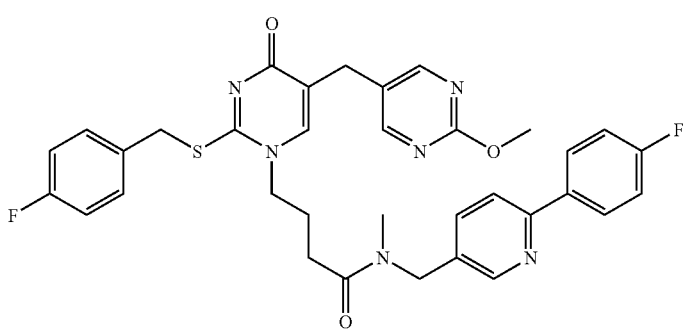 | 1-(3-(N-methyl-N-(2-(4-fluorophenyl)-pyrid-5-ylmethyl)aminocarbonyl)prop-1-yl)-2-(4-fluorobenzyl)thio-5-(2-methoxy-5-pyrimidylmethyl)pyrimidin-4-one |
| 42 | Int. A3<br>Int. B104 | 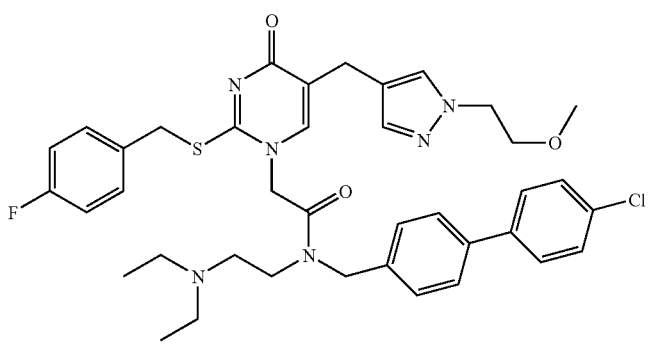 | 1-(N-(2-(diethylamino)ethyl)-N-(4-(4-chlorophenyl)benzyl)aminocarbonyl-methyl)-2-(4-fluorobenzyl)thio-5-(1-(2-methoxyethyl)-4-pyrazolylmethyl)-pyrimidin-4-one bitartrate |

-continued

| Ex. No. | Precursors | Structure | Name |
|---|---|---|---|
| 43 | Int. A73<br>Int. B104 | 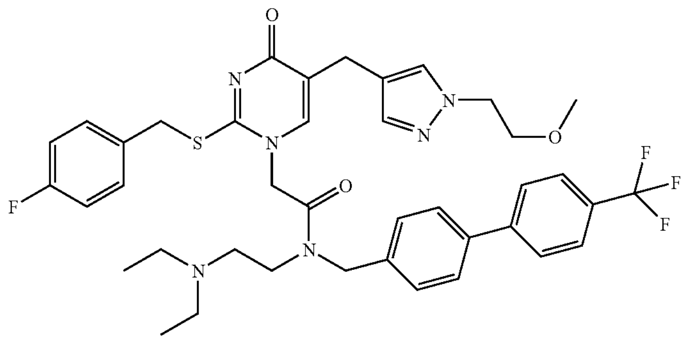 | 1-(N-(2-(diethylamino)ethyl)-N-(4-(4-trifluoromethylphenyl)benzyl)aminocarbonylmethyl)-2-(4-fluorobenzyl)thio-5-(1-(2-methoxyethyl)-4-pyrazolylmethyl)pyrimidin-4-one bitartrate |
| 44 | Int. A6<br>Int. B100 | 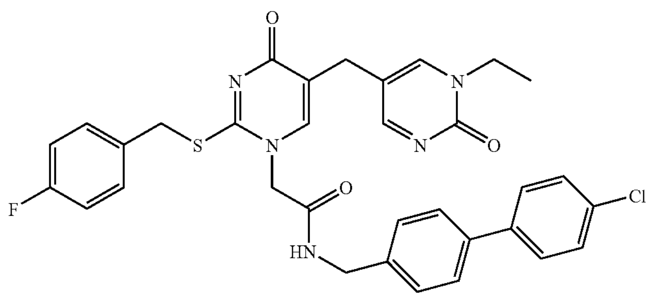 | 1-(4-(4-chlorophenyl)benzylaminocarbonylmethyl)-2-(4-fluorobenzyl)thio-5-(1-ethyl-2-oxo-5-pyrimidylmethyl)pyrimidin-4-one |
| 45 | Int. A2<br>Int. B100 | 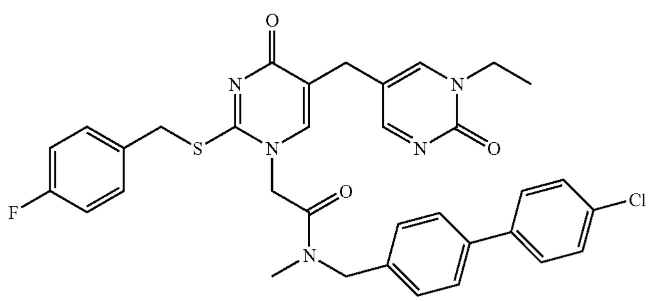 | 1-(N-methyl-N-(4-(4-chlorophenyl)benzyl)aminocarbonylmethyl)-2-(4-fluorobenzyl)thio-5-(1-ethyl-2-oxo-5-pyrimidylmethyl)pyrimidin-4-one |
| 46 | Int. A44<br>Int. B100 | 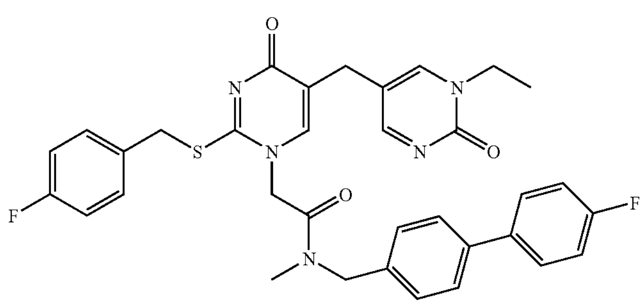 | 1-(N-methyl-N-(4-(4-fluorophenyl)benzyl)aminocarbonylmethyl)-2-(4-fluorobenzyl)thio-5-(1-ethyl-2-oxo-5-pyrimidylmethyl)pyrimidin-4-one |
| 47 | Int. A2<br>Int. B92 | 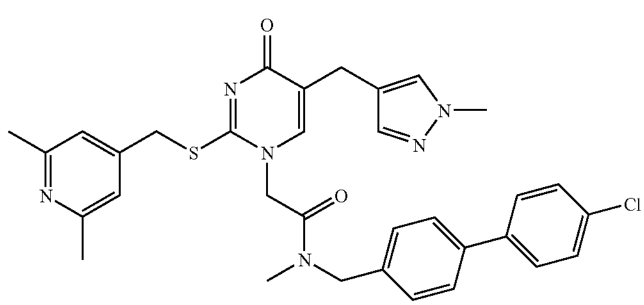 | 1-(N-methyl-N-(4-(4-chlorophenyl)benzyl)aminocarbonylmethyl)-2-(2,6-dimethylpyrid-4-yl)methylthio-5-(1-methyl-4-pyrazolylmethyl)pyrimidin-4-one |

-continued

| Ex. No. | Precursors | Structure | Name |
|---|---|---|---|
| 48 | Int. A3<br>Int. B90 | 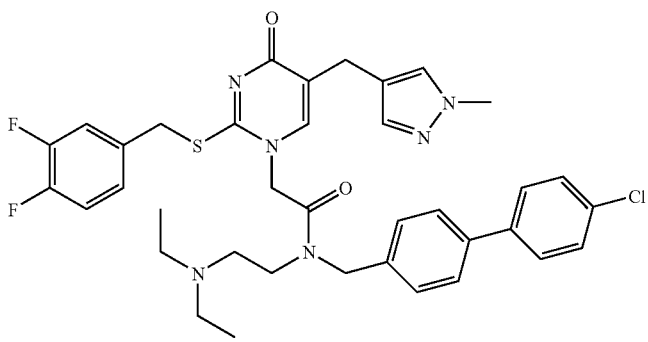 | 1-(N-(2-(diethylamino)ethyl)-N-(4-(4-chlorophenyl)benzyl)aminocarbonyl-methyl)-2-(3,4-difluorobenzyl)thio-5-(1-methyl-4-pyrazolylmethyl)pyrimidin-4-one hydrochloride |
| 49 | Int. A45<br>Int. B90 | 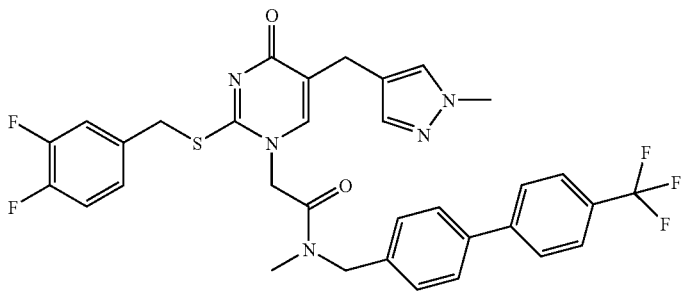 | 1-(N-methyl-N-(4-(4-trifluoromethyl-phenyl)benzyl)aminocarbonylmethyl)-2-(3,4-difluorobenzyl)thio-5-(1-methyl-4-pyrazolylmethyl)pyrimidin-4-one |
| 50 | Int. A46<br>Int. B71 | 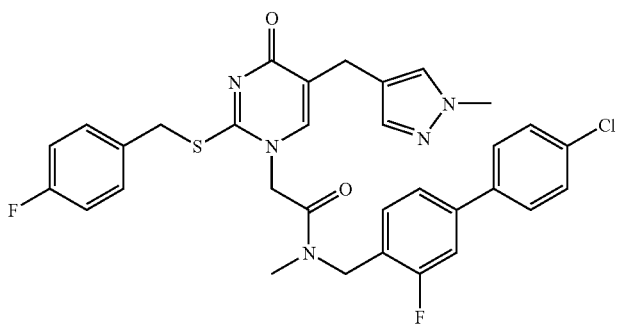 | 1-(N-methyl-N-(4-(4-chlorophenyl)-2-fluorobenzyl)aminocarbonylmethyl)-2-(4-fluorobenzyl)thio-5-(1-methyl-4-pyrazolylmethyl)pyrimidin-4-one |
| 51 | Int. A56<br>Int. B71 | 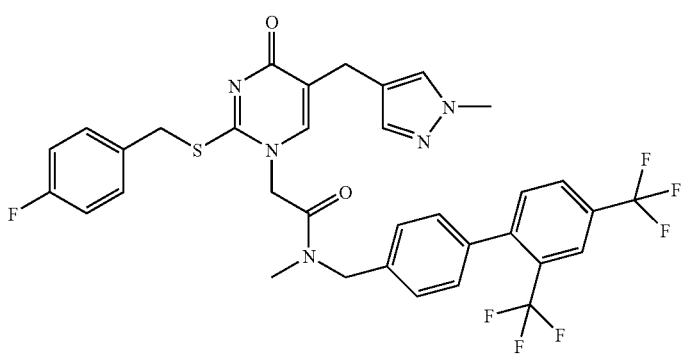 | 1-(N-methyl-N-(4-(2,4-bis(trifluoro-methyl)phenyl)benzyl)aminocarbonyl-methyl)-2-(4-fluorobenzyl)thio-5-(1-methyl-4-pyrazolylmethyl)pyrimidin-4-one |

| Ex. No. | Precursors | Structure | Name |
|---|---|---|---|
| 52 | Int. A60<br>Int. B71 | 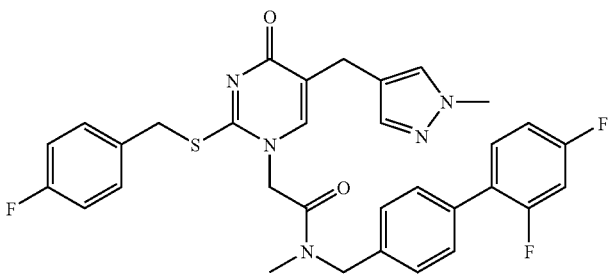 | 1-(N-methyl-N-(4-(2,4-difluorophenyl)-benzyl)aminocarbonylmethyl)-2-(4-fluorobenzyl)thio-5-(1-methyl-4-pyrazolylmethyl)pyrimidin-4-one |
| 53 | Int. A59<br>Int. B71 | 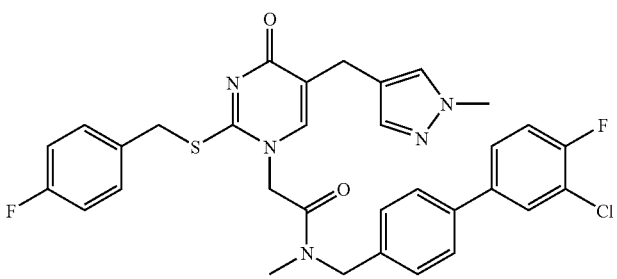 | 1-(N-methyl-N-(4-(3-chloro-4-fluoro-phenyl)benzyl)aminocarbonylmethyl)-2-(4-fluorobenzyl)thio-5-(1-methyl-4-pyrazolylmethyl)pyrimidin-4-one |
| 54 | Int. A53<br>Int. B71 | 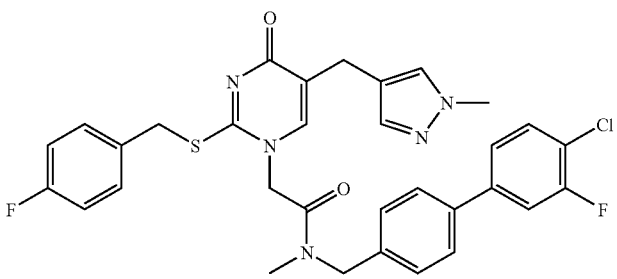 | 1-(N-methyl-N-(4-(3-fluoro-4-chlororo-phenyl)benzyl)aminocarbonylmethyl)-2-(4-fluorobenzyl)thio-5-(1-methyl-4-pyrazolylmethyl)pyrimidin-4-one |
| 55 | Int. A107<br>Int. B71 | 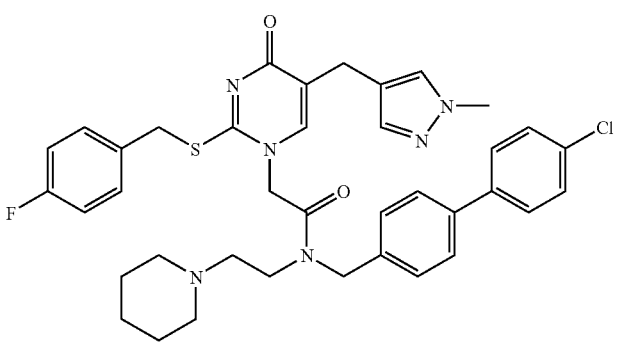 | 1-(N-(2-(1-piperidino)ethyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 56 | Int. A75<br>Int. B71 | 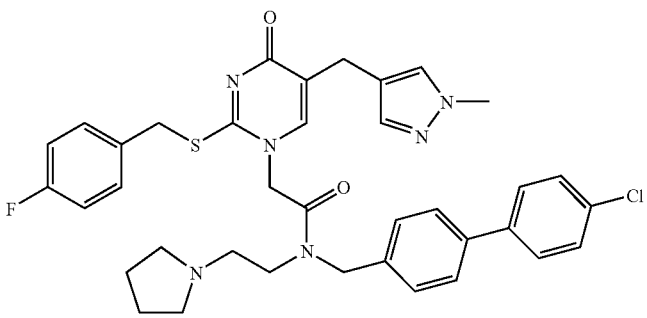 | 1-(N-(2-(1-pyrrolidino)ethyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |

| Ex. No. | Precursors | Structure | Name |
|---|---|---|---|
| 57 | Int. A76<br>Int. B71 | 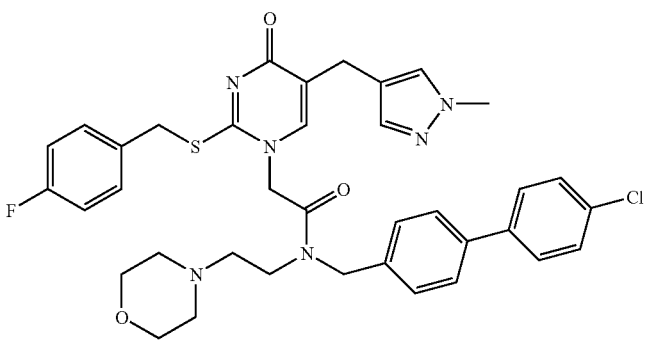 | 1-(N-(2-(4-morpholino)ethyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 58 | Int. A95<br>Int. B71 | 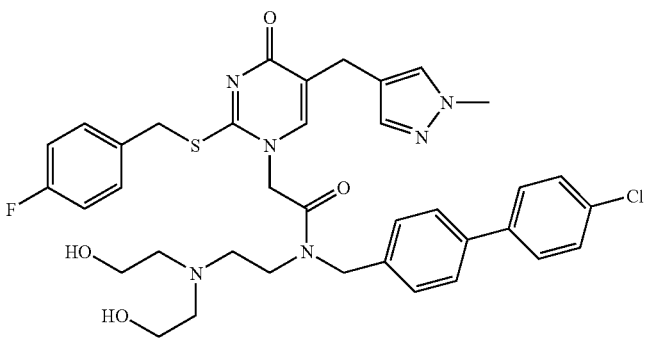 | 1-(N-(2-(bis(2-hydroxyethyl)amino)-ethyl)-N-(4-(4-chlorophenyl)benzyl)_aminocarbonylmethyl)-2-(4-fluoro-benzyl)thio-5-(1-methyl-4-pyrazolyl-methyl)pyrimidin-4-one |
| 59 | Int. A74<br>Int. B71 | 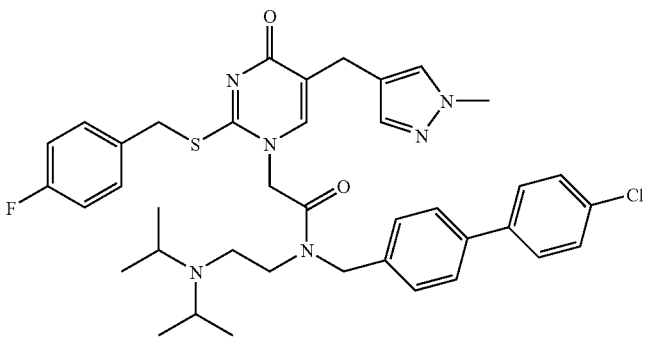 | 1-(N-(2-(di-isopropylamino)ethyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 60 | Int. A94<br>Int. B71 | 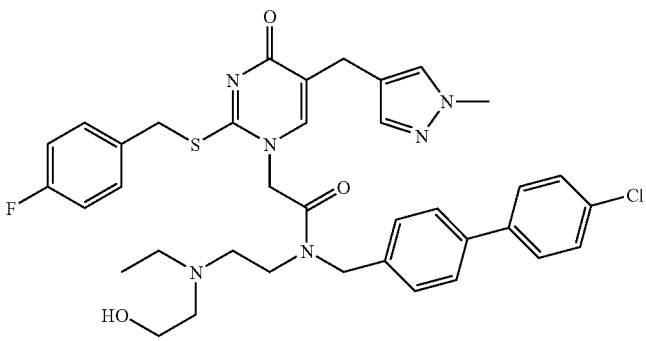 | 1-(N-(2-(N-(2-hydroxyethyl)-N-ethyl-amino)ethyl)-N-(4-(4-chlorophenyl)-benzyl)aminocarbonylmethyl)-2-(4-fluorobenzyl)thio-5-(1-methyl-4-pyrazolylmethyl)pyrimidin-4-one bitartrate |

-continued

| Ex. No. | Precursors | Structure | Name |
|---|---|---|---|
| 61 | Int. A70<br>Int. B71 | 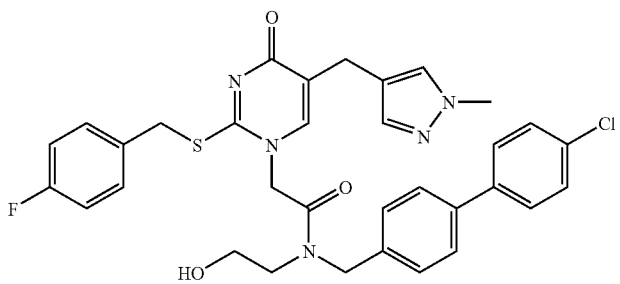 | 1-(N-(2-hydroxyethyl)-N-(4-(4-chlorophenyl)benzyl)aminocarbonylmethyl)-2-(4-fluorobenzyl)thio-5-(1-methyl-4-pyrazolylmethyl)pyrimidin-4-one |
| 62 | Int. A51<br>Int. B71 | 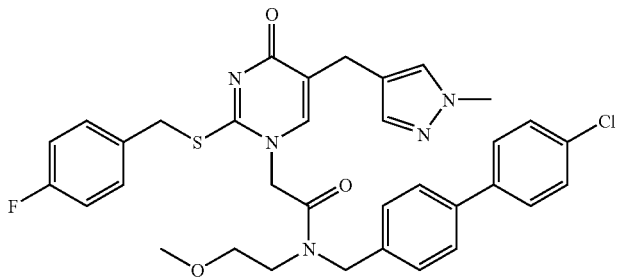 | 1-(N-(2-methoxyethyl)-N-(4-(4-chlorophenyl)benzyl)aminocarbonylmethyl)-2-(4-fluorobenzyl)thio-5-(1-methyl-4-pyrazolylmethyl)pyrimidin-4-one |
| 63 | Int. A80<br>Int. B71 | 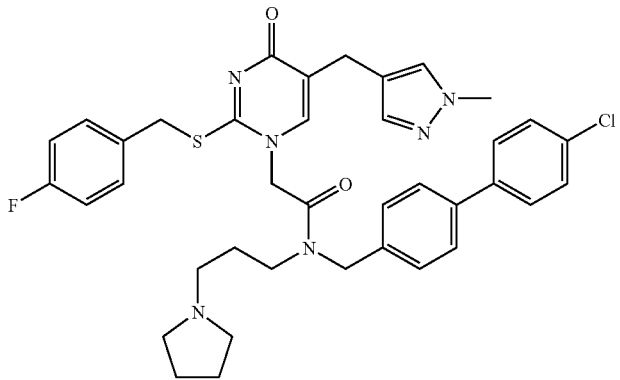 | 1-(N-(3-(1-pyrrolidino)propyl)-N-(4-(4-chlorophenyl)benzyl)aminocarbonylmethyl)-2-(4-fluorobenzyl)thio-5-(1-methyl-4-pyrazolylmethyl)pyrimidin-4-one hydrochloride |
| 64 | Int. A83<br>Int. B71 | 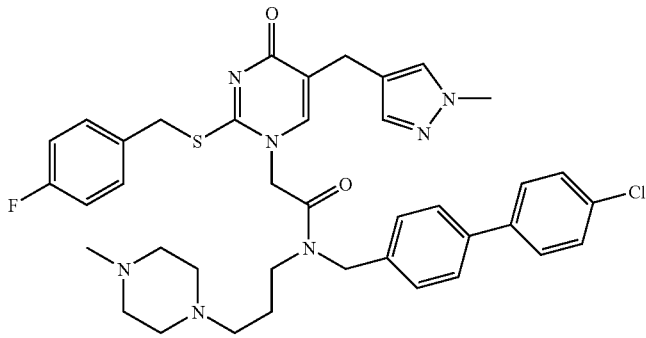 | 1-(N-(3-(4-methyl-1-piperazino)propyl)-N-(4-(4-chlorophenyl)benzyl)aminocarbonylmethyl)-2-(4-fluorobenzyl)thio-5-(1-methyl-4-pyrazolylmethyl)-pyrimidin-4-one hydrochloride |

| Ex. No. | Precursors | Structure | Name |
|---|---|---|---|
| 65 | Int. A82<br>Int. B71 | 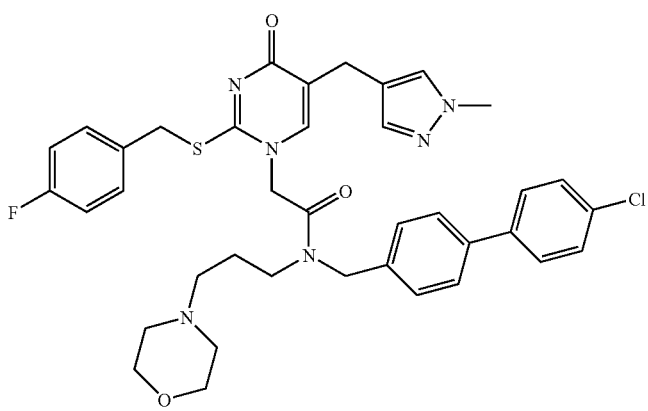 | 1-(N-(3-(4-morpholino)propyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 66 | Int. A79<br>Int. B71 | 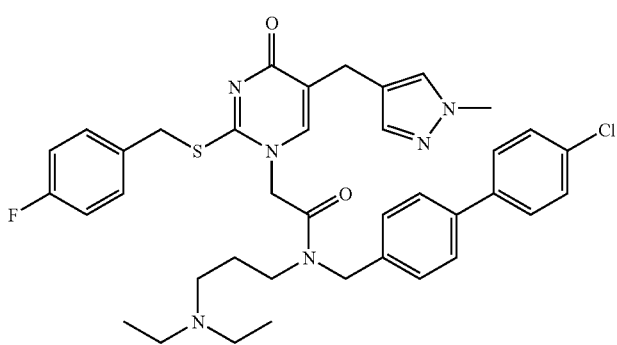 | 1-(N-(3-(diethylamino)propyl)-N-(4-(4-chlorophenyl)benzyl)aminocarbonyl-methyl)-2-(4-fluorobenzyl)thio-5-(1-methyl-4-pyrazolylmethyl)pyrimidin-4-one |
| 67 | Int. A62<br>Int. B71 | 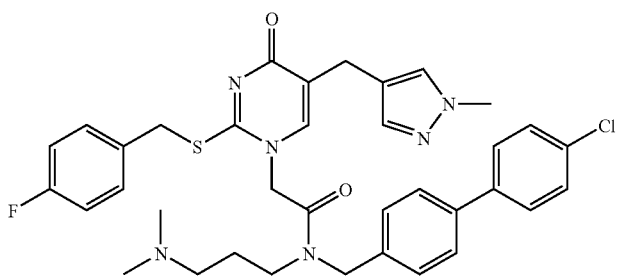 | 1-(N-(3-(dimethylamino)propyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 68 | Int. A50<br>Int. B71 | 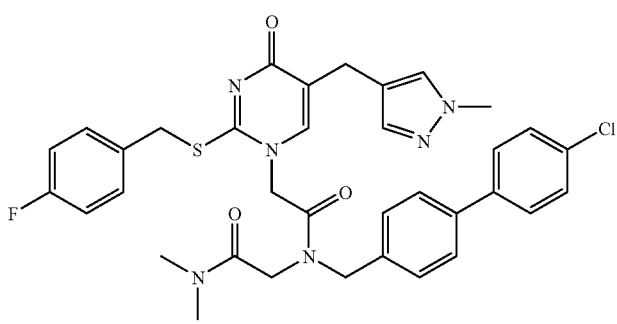 | 1-(N-(dimethylaminocarbonylmethyl)-N-(4-(4-chlorophenyl)benzyl)amino-carbonylmethyl)-2-(4-fluorobenzyl)thio-5-(1-methyl-4-pyrazolylmethyl)-pyrimidin-4-one |

| Ex. No. | Precursors | Structure | Name |
|---|---|---|---|
| 69 | Int. A48<br>Int. B71 | 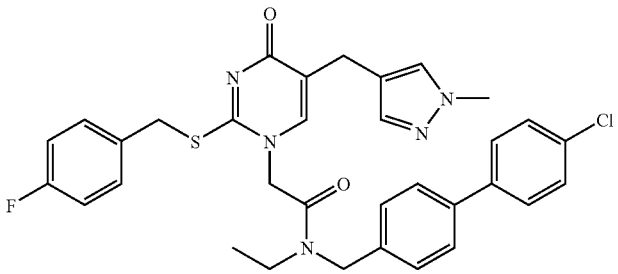 | 1-(N-ethyl-N-(4-(4-chlorophenyl)-benzyl)aminocarbonylmethyl)-2-(4-fluorobenzyl)thio-5-(1-methyl-4-pyrazolylmethyl)pyrimidin-4-one |
| 70 | Int. A6<br>Int. B71 | 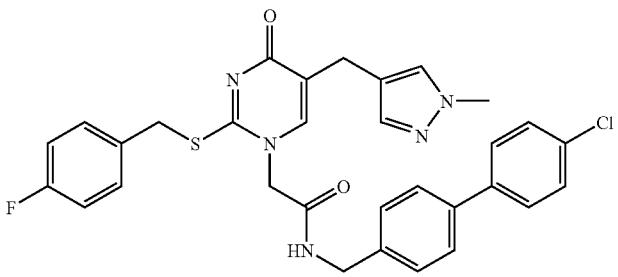 | 1-(4-(4-chlorophenyl)benzyl)amino-carbonylmethyl)-2-(4-fluorobenzyl)thio-5-(1-methyl-4-pyrazolylmethyl)-pyrimidin-4-one |
| 71 | Int. A93<br>Int. B71 | 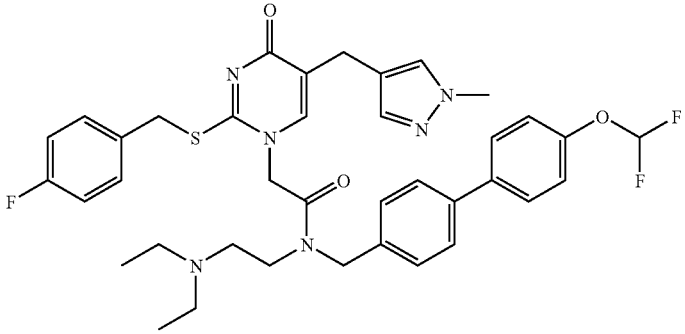 | 1-(N-(2-(diethylamino)ethyl)-N-(4-(4-difluoromethoxyphenyl)benzyl)amino-carbonylmethyl)-2-(4-fluorobenzyl)thio-5-(1-methyl-4-pyrazolylmethyl)-pyrimidin-4-one hydrochloride |
| 72 | Int. A120<br>Int. B71 | 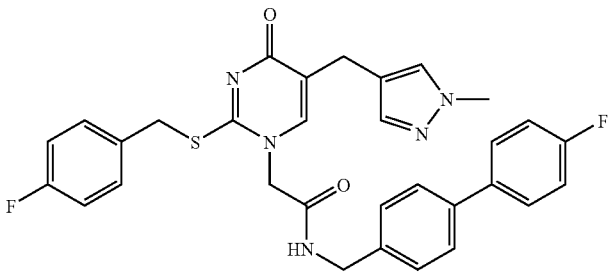 | 1-(4-(4-fluorophenyl)benzylamino-carbonylmethyl)-2-(4-fluorobenzyl)thi -5-(1-methyl-4-pyrazolylmethyl)-pyrimidin-4-one |
| 73 | Int. A44<br>Int. B71 | 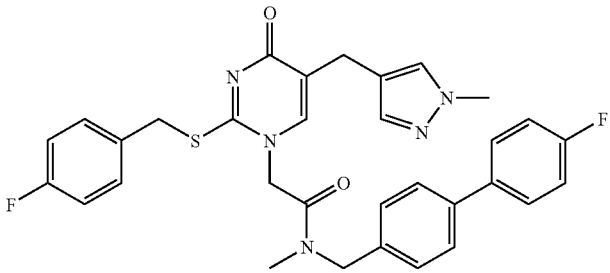 | 1-(N-methyl-N-(4-(4-fluorophenyl)-benzyl)aminocarbonylmethyl)-2-(4-fluorobenzyl)thio-5-(1-methyl-4-pyrazolylmethyl)pyrimidin-4-one |

| Ex. No. | Precursors | Structure | Name |
|---|---|---|---|
| 74 | Int. A54<br>Int. B71 | 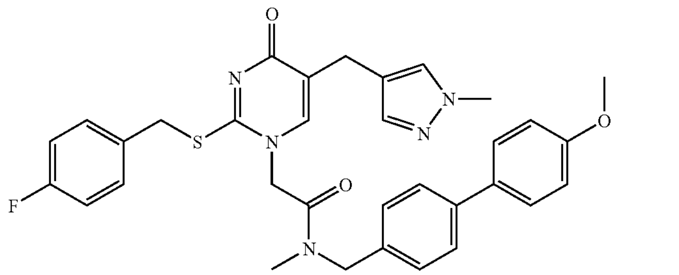 | 1-(N-methyl-N-(4-(4-methoxyphenyl)-benzyl)aminocarbonylmethyl)-2-(4-fluorobenzyl)thio-5-(1-methyl-4-pyrazolylmethyl)pyrimidin-4-one |
| 75 | Int. A92<br>Int. B71 | 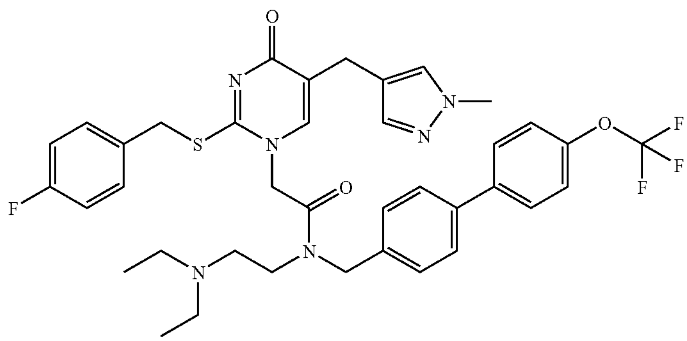 | 1-(N-(2-(diethylamino)ethyl)-N-(4-(4-trifluoromethoxyphenyl)benzyl)aminocarbonylmethyl)-2-(4-fluorobenzyl)thio-5-(1-methyl-4-pyrazolylmethyl)-pyrimidin-4-one hydrochloride |
| 76 | Int. A71<br>Int. B71 | 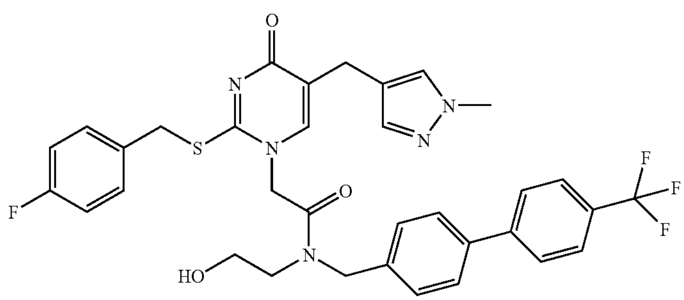 | 1-(N-(2-hydroxyethyl)-N-(4-(4-trifluoromethylphenyl)benzyl)aminocarbonylmethyl)-2-(4-fluorobenzyl)thio-5-(1-methyl-4-pyrazolylmethyl)-pyrimidin-4-one |
| 77 | Int. A78<br>Int. B71 | 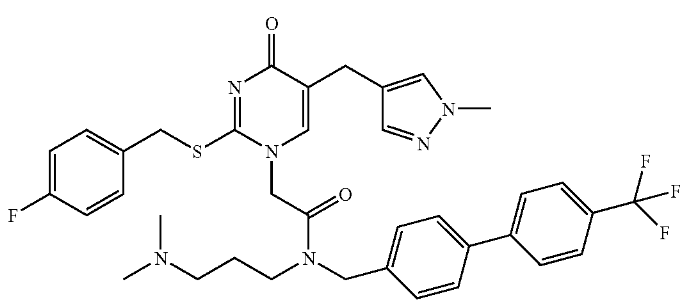 | 1-(N-(3-(dimethylamino)propyl)-N-(4-(4-trifluoromethylphenyl)benzyl)-aminocarbonylmethyl)-2-(4-fluoro-benzyl)thio-5-(1-methyl-4-pyrazolyl-methyl)pyrimidin-4-one hydrochloride |
| 78 | Int. A97<br>Int. B71 | 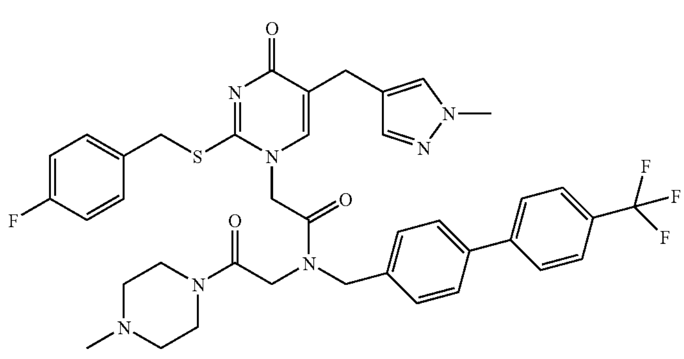 | 1-(N-(4-methyl-1-piperazinocarbonyl-methyl)-N-(4-(4-trifluoromethylphenyl)-benzyl)aminocarbonylmethyl)-2-(4-fluorobenzyl)thio-5-(1-methyl-4-pyrazolylmethyl)pyrimidin-4-one hydrochloride |

-continued

| Ex. No. | Precursors | Structure | Name |
|---|---|---|---|
| 79 | Int. A96<br>Int. B71 | 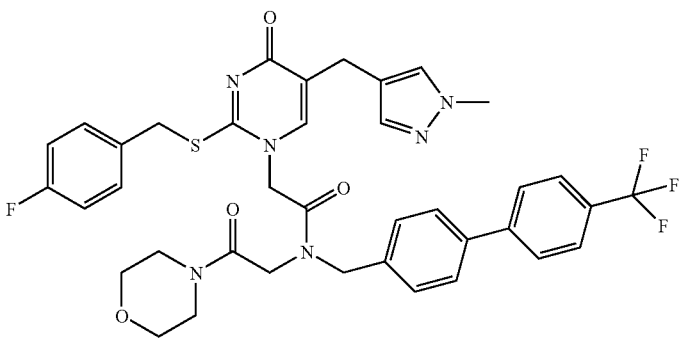 | 1-(N-(4-morpholinocarbonylmethyl)-N-(4-(4-trifluoromethylphenyl)benzyl)-aminocarbonylmethyl)-2-(4-fluoro-benzyl)thio-5-(1-methyl-4-pyrazolyl-methyl)pyrimidin-4-one |
| 80 | Int. A52<br>Int. B71 | 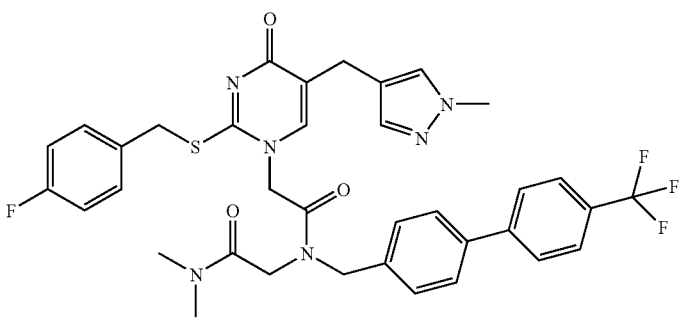 | 1-(N-(dimethylaminocarbonylmethyl)-N-(4-(4-trifluoromethylphenyl)benzyl)-aminocarbonylmethyl)-2-(4-fluoro-benzyl)thio-5-(1-methyl-4-pyrazolyl-methyl)pyrimidin-4-one |
| 81 | Int. A121<br>Int. B71 | 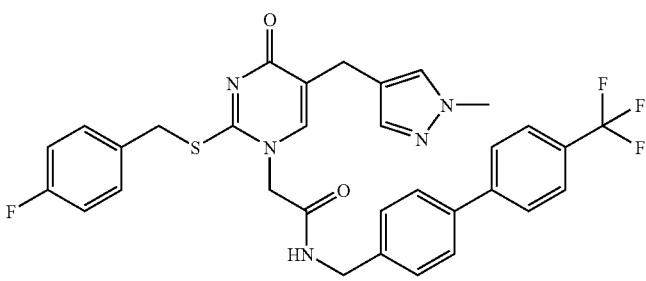 | 1-(4-(4-trifluoromethylphenyl)benzyl-aminocarbonylmethyl)-2-(4-fluoro-benzyl)thio-5-(1-methyl-4-pyrazolyl-methyl)pyrimidin-4-one |
| 82 | Int. A98<br>Int. B71 | 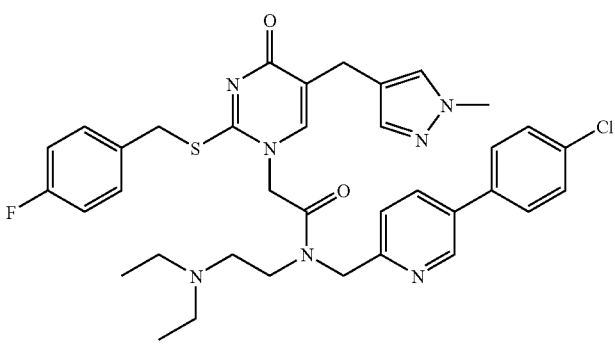 | 1-(N-(2-(diethylamino)ethyl)-N-(5-(4-chlorophenyl)pyrid-2-ylmethyl)amino-carbonylmethyl)-2-(4-fluorobenzyl)thio-5-(1-methyl-4-pyrazolylmethyl)-pyrimidin-4-one hydrochloride |

-continued

| Ex. No. | Precursors | Structure | Name |
|---|---|---|---|
| 83 | Int. A102<br>Int. B71 | 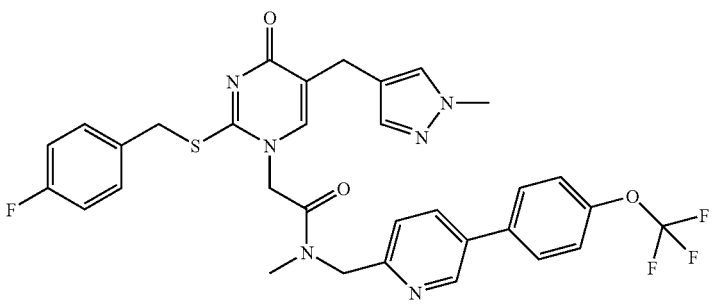 | 1-(N-(2-(dimethylamino)ethyl)-N-(5-(4-trifluoromethoxyphenyl)pyrid-2-yl-methyl)aminocarbonylmethyl)-2-(4-fluorobenzyl)thio-5-(1-methyl-4-pyrazolylmethyl)pyrimidin-4-one |
| 84 | Int. A99<br>Int. B71 | 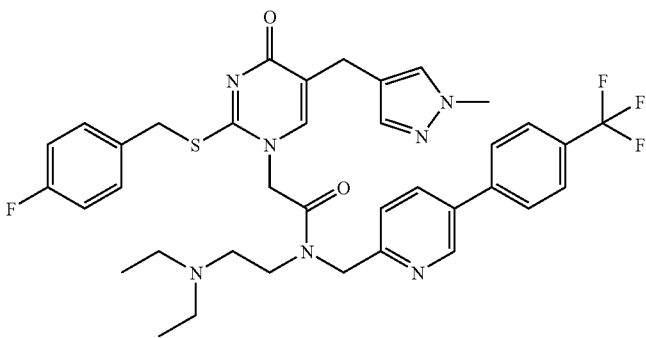 | 1-(N-(2-(diethylamino)ethyl)-N-(5-(4-trifluoromethylphenyl)pyrid-2-yl-methyl)aminocarbonylmethyl)-2-(4-fluorobenzyl)thio-5-(1-methyl-4-pyrazolylmethyl)pyrimidin-4-one hydrochloride |
| 85 | Int. A101<br>Int. B71 | 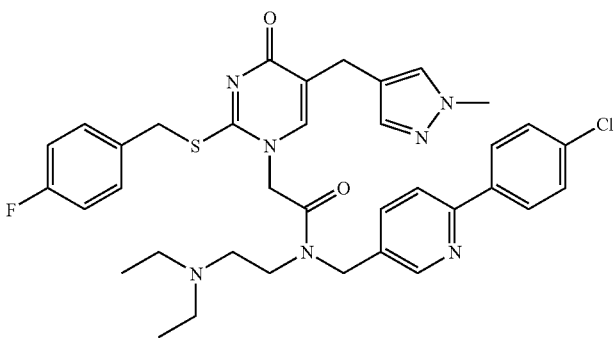 | 1-(N-(2-(diethylamino)ethyl)-N-(2-(4-chlorophenyl)pyrid-5-ylmethyl)amino-carbonylmethyl)-2-(4-fluorobenzyl)thio-5-(1-methyl-4-pyrazolylmethyl)-pyrimidin-4-one hydrochloride |
| 86 | Int. A103<br>Int. B71 | 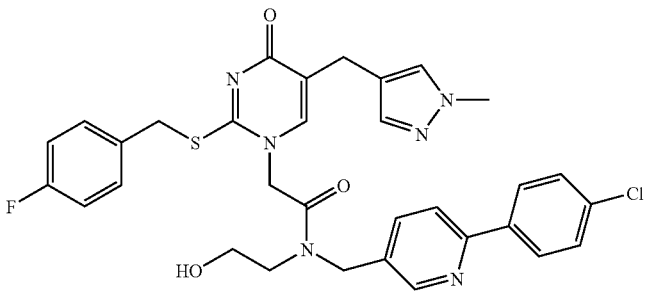 | 1-(N-(2-hydroxyethyl)-N-(2-(4-chloro-phenyl)pyrid-5-yl-methyl)amino-carbonylmethyl)-2-(4-fluorobenzyl)thio-5-(1-methyl-4-pyrazolylmethyl)-pyrimidin-4-one |

| Ex. No. | Precursors | Structure | Name |
|---|---|---|---|
| 87 | Int. A122<br>Int. B71 | 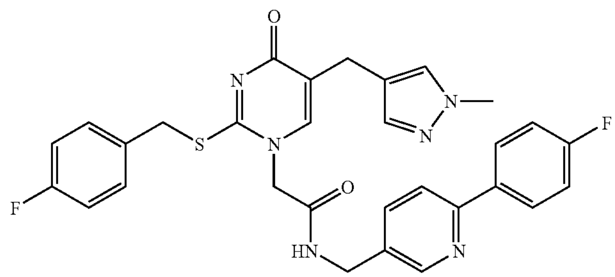 | 1-(2-(4-fluorophenyl)pyrid-5-ylmethyl-aminocarbonylmethyl)-2-(4-fluoro-benzyl)thio-5-(1-methyl-4-pyrazolyl-methyl)pyrimidin-4-one |
| 88 | Int. A64<br>Int. B71 | 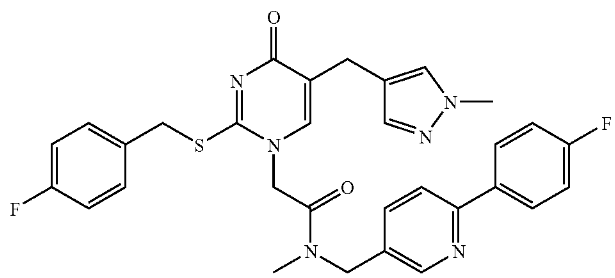 | 1-(N-methyl-N-(2-(4-fluorophenyl)-pyrid-5-ylmethyl)aminocarbonyl-methyl)-2-(4-fluorobenzyl)thio-5-(1-methyl-4-pyrazolylmethyl)pyrimidin-4-one |
| 89 | Int. A100<br>Int. B71 | 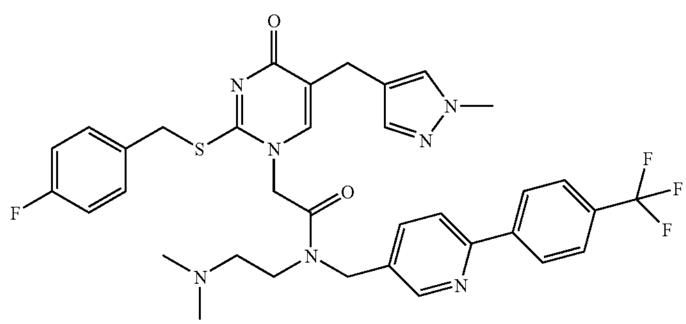 | 1-(N-(2-(dimethylamino)ethyl)-N-(2-(4-trifluoromethylphenyl)pyrid-5-ylmethyl)aminocarbonylmethyl)-2-(4-fluorobenzyl)thio-5-(1-methyl-4-pyrazolylmethyl)pyrimidin-4-one hydrochloride |
| 90 | Int. A104<br>Int. B71 | 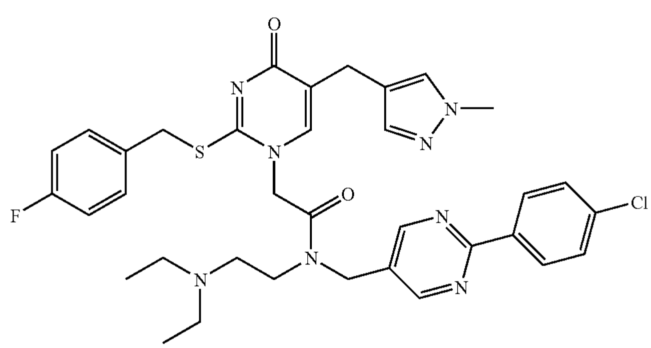 | 1-(N-(2-(diethylamino)ethyl)-N-(2-(4-chlorophenyl)pyrimid-5-ylmethyl)-aminocarbonylmethyl)-2-(4-fluoro-benzyl)thio-5-(1-methyl-4-pyrazolyl-methyl)pyrimidin-4-one bitartrate |
| 91 | Int. A123<br>Int. B71 | 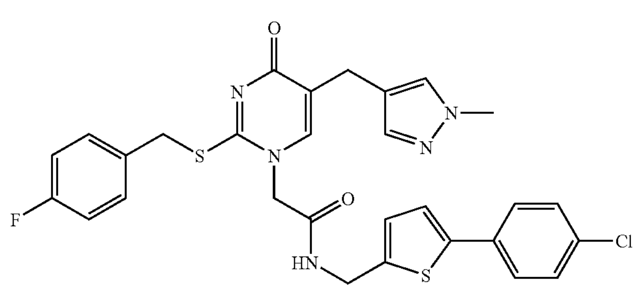 | 1-(5-(4-chlorophenyl)thien-2-ylmethyl-aminocarbonylmethyl)-2-(4-fluoro-benzyl)thio-5-(1-methyl-4-pyrazolyl-methyl)pyrimidin-4-one |

-continued

| Ex. No. | Precursors | Structure | Name |
|---|---|---|---|
| 92 | Int. A66<br>Int. B71 | 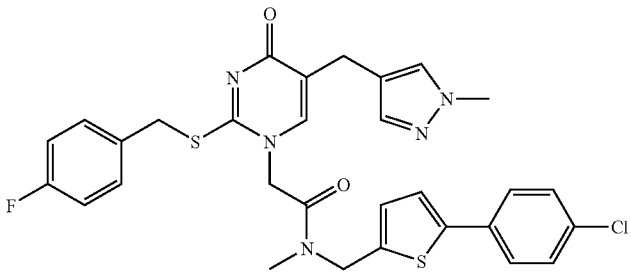 | 1-(N-methyl-N-(5-(4-chlorophenyl)-thien-2-ylmethyl)aminocarbonylmethyl)-2-(4-fluorobenzyl)thio-5-(1-methyl-4-pyrazolylmethyl)pyrimidin-4-one |
| 93 | Int. A63<br>Int. B71 | 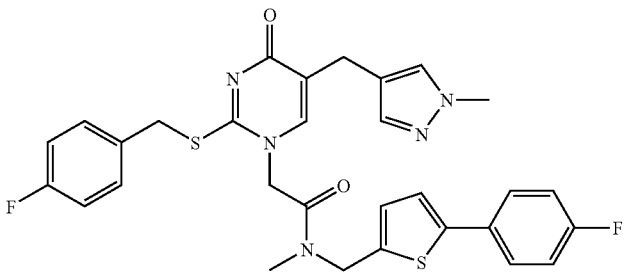 | 1-(N-methyl-N-(5-(4-fluorophenyl)-thien-2-ylmethyl)aminocarbonylmethyl)-2-(4-fluorobenzyl)thio-5-(1-methyl-4-pyrazolylmethyl)pyrimidin-4-one |
| 94 | Int. A3<br>Int. B89 | 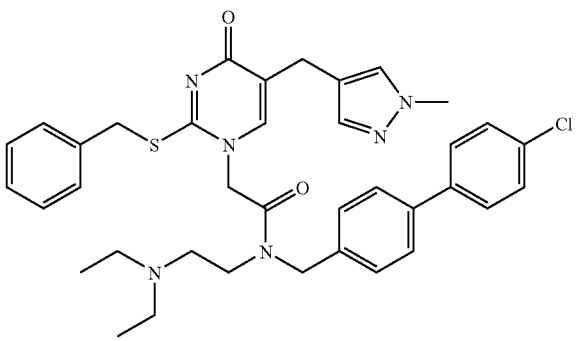 | 1-(N-(2-(diethylamino)ethyl)-N-(4-(4-chlorophenyl)benzyl)aminocarbonylmethyl)-2-benzylthio-5-(1-methyl-4-pyrazolylmethyl)pyrimidin-4-one hydrochloride |
| 95 | Int. A83<br>Int. B101 | 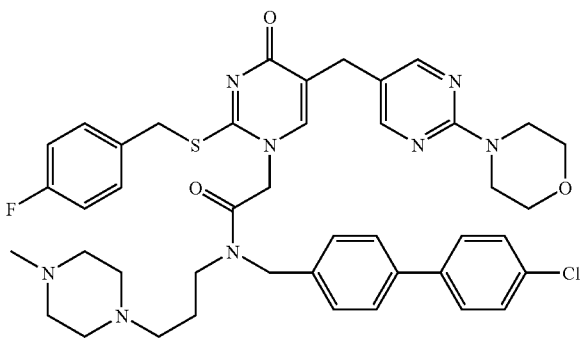 | 1-(N-(3-(4-methyl-1-piperazino)propyl)-N-(4-(4-chlorophenyl)benzyl)aminocarbonylmethyl)-2-(4-fluorobenzyl)thio-5-(2-(4-morpholino)-5-pyrimidylmethyl)pyrimidin-4-one bitartrate |
| 96 | Int. A45<br>Int. B101 | 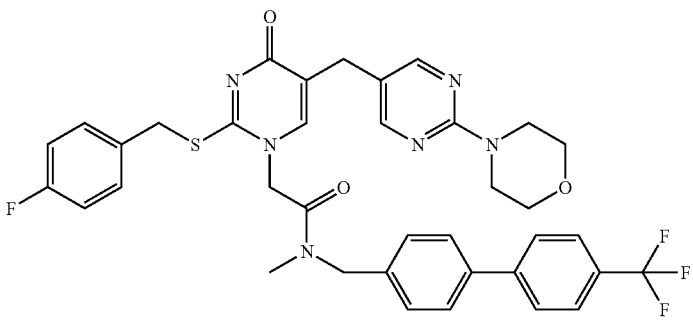 | 1-(N-methyl-N-(4-(4-trifluoromethylphenyl)benzyl)aminocarbonylmethyl)-2-(4-fluorobenzyl)thio-5-(2-(4-morpholino)-5-pyrimidylmethyl)-pyrimidin-4-one |

-continued

| Ex. No. | Precursors | Structure | Name |
|---|---|---|---|
| 97 | Int. A83<br>Int. B102 | 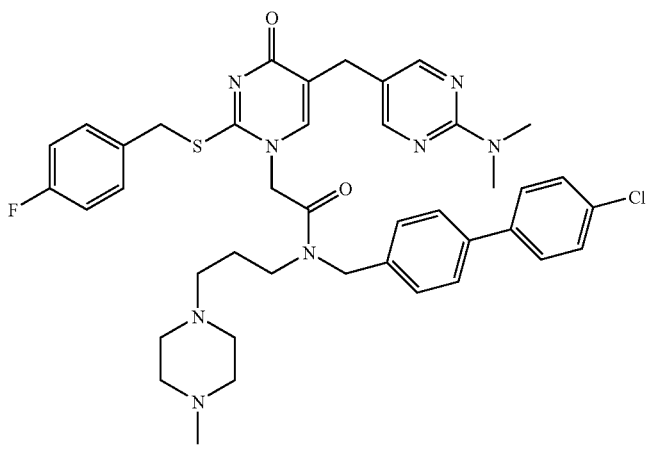 | 1-(N-(3-(4-methyl-1-piperazino)propyl)-N-(4-(4-chlorophenyl)benzyl)amino-carbonylmethyl)-2-(4-fluorobenzyl)thio-5-(2-dimethylamino-5-pyrimidyl-methyl)pyrimidin-4-one bitartrate |
| 98 | Int. A2<br>Int. B102 | 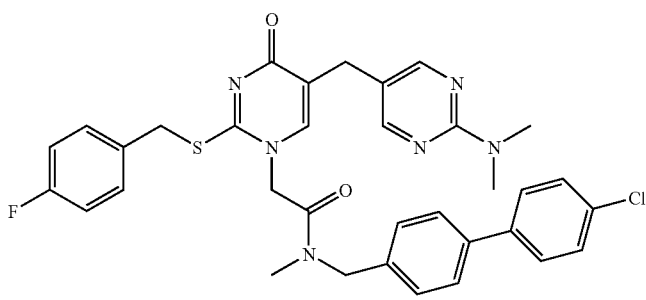 | 1-(N-methyl-N-(4-(4-chlorophenyl)-benzyl)aminocarbonylmethyl)-2-(4-fluorobenzyl)thio-5-(2-dimethylamino-5-pyrimidylmethyl)pyrimidin-4-one |
| 99 | Int. A45<br>Int. B102 | 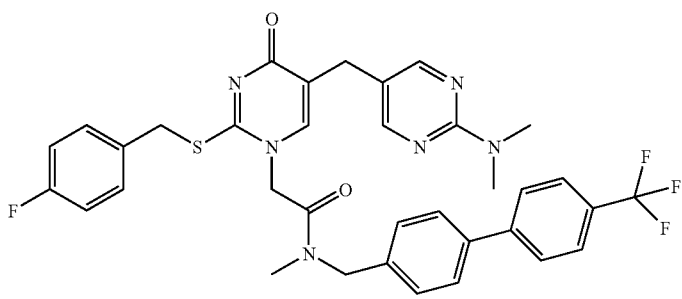 | 1-(N-methyl-N-(4-(4-trifluoromethyl-phenyl)benzyl)aminocarbonylmethyl)-2-(4-fluorobenzyl)thio-5-(2-dimethyl-amino-5-pyrimidylmethyl)pyrimidin-4-one |
| 100 | Int. A73<br>Int. B103 | 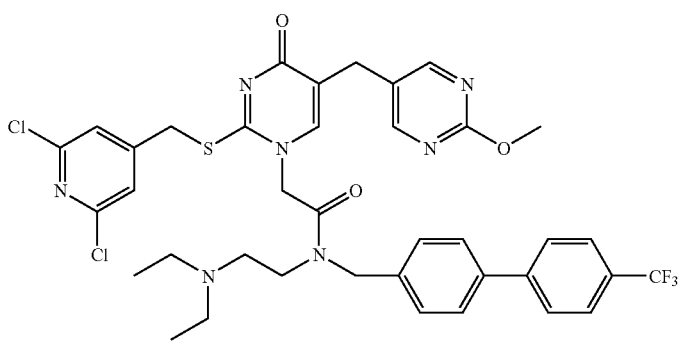 | 1-(N-(2-(diethylamino)ethyl)-N-(4-(4-trifluoromethylphenyl)benzyl)amino-carbonylmethyl)-2-(2,6-dichloropyrid-4-yl)methylthio-5-(2-methoxy-5-pyrimidylmethyl)pyrimidin-4-one bitartrate |

-continued

| Ex. No. | Precursors | Structure | Name |
|---|---|---|---|
| 101 | Int. A45<br>Int. B103 | 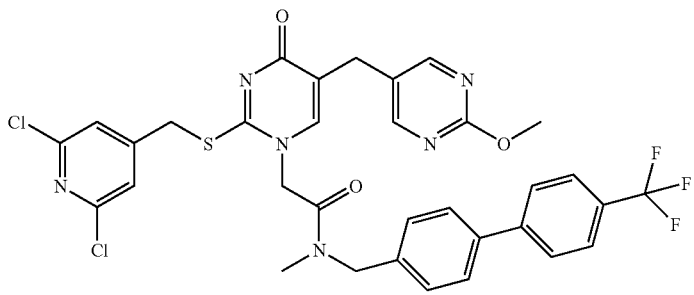 | 1-(N-methyl-N-(4-(4-trifluoromethyl-phenyl)benzyl)aminocarbonylmethyl)-2-(2,6-dichloropyrid-4-yl)methylthio-5-(2-methoxy-5-pyrimidylmethyl)pyrimidin-4-one |
| 102 | Int. A160<br>Int. B71 | 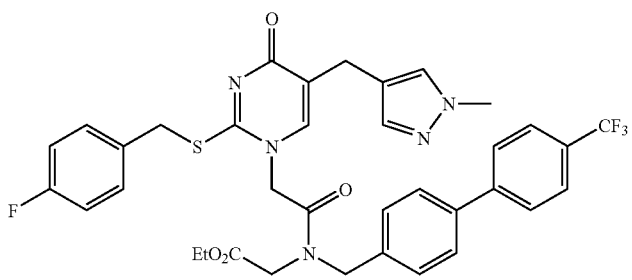 | 1-(N-(Ethoxycarbonylmethyl)-N-(4-(4-trifluoromethylphenyl)benzyl)amino-carbonylmethyl)-2-(4-fluorobenzyl)thio-5-(1-methyl-4-pyrazolyl-methyl)pyrimidin-4-one |
| 103 | Int. A2<br>Int. B90 | 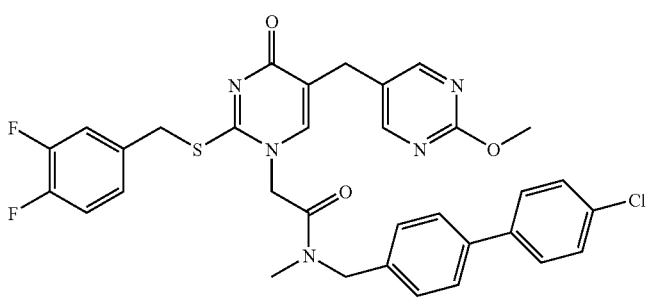 | 1-(N-methyl-N-(4-(4-chlorophenyl)-benzyl)aminocarbonylmethyl)-2-(3,4-difluorobenzyl)thio-5-(2-methoxy-5-pyrimidylmethyl)pyrimidin-4-one |
| 104 | Int. A45<br>Int. B90 | 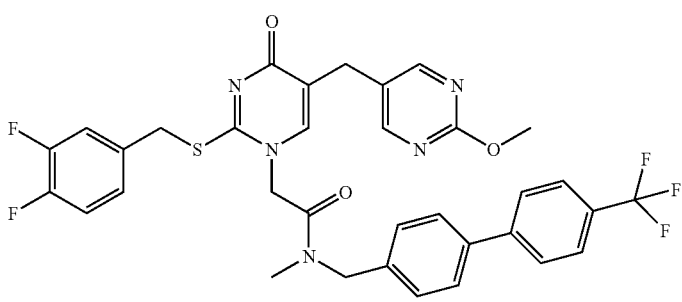 | 1-(N-methyl-N-(4-(4-trifluoromethyl-phenyl)benzyl)aminocarbonylmethyl)-2-(3,4-difluorobenzyl)thio-5-(2-methoxy-5-pyrimidylmethyl)pyrimidin-4-one |
| 105 | Int. A46<br>Int. B104 | 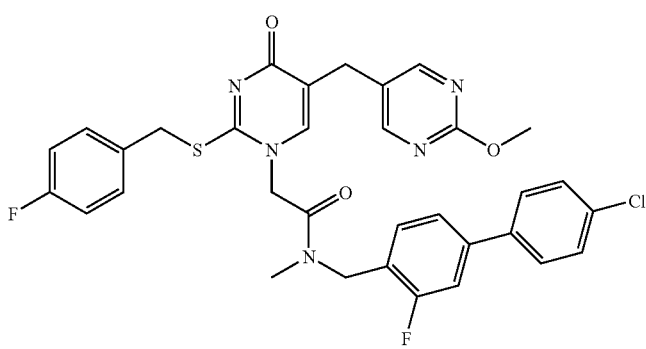 | 1-(N-methyl-N-(4-(4-chlorophenyl)-2-fluorobenzyl)aminocarbonylmethyl)-2-(4-fluorobenzyl)thio-5-(2-methoxy-5-pyrimidylmethyl)pyrimidin-4-one |

-continued

| Ex. No. | Precursors | Structure | Name |
|---|---|---|---|
| 106 | Int. A58<br>Int. B104 | 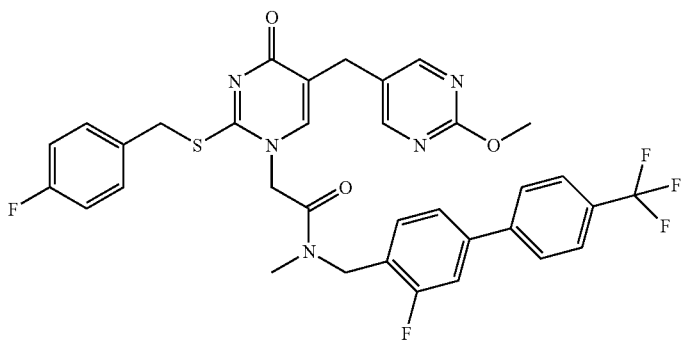 | 1-(N-methyl-N-(4-(4-trifluoromethyl-phenyl)-2-fluorobenzyl)aminocarbonyl-methyl)-2-(4-fluorobenzyl)thio-5-(2-methoxy-5-pyrimidylmethyl)pyrimidin-4-one |
| 107 | Int. A10<br>Int. B104 | 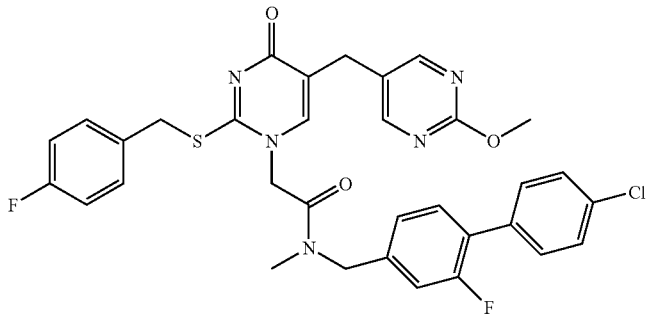 | 1-(N-methyl-N-(4-(4-chlorophenyl)-3-fluorobenzyl)aminocarbonylmethyl)-2-(4-fluorobenzyl)thio-5-(2-methoxy-5-pyrimidylmethyl)pyrimidin-4-one |
| 108 | Int. A57<br>Int. B104 | 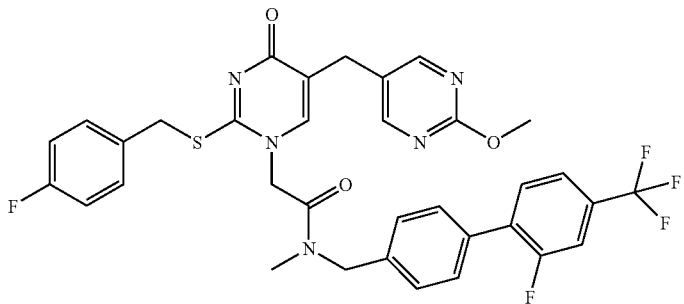 | 1-(N-methyl-N-(4-(2-fluoro-4-trifluoro-methylphenyl)benzyl)aminocarbonyl-methyl)-2-(4-fluorobenzyl)thio-5-(2-methoxy-5-pyrimidylmethyl)pyrimidin-4-one |
| 109 | Int. A60<br>Int. B104 | 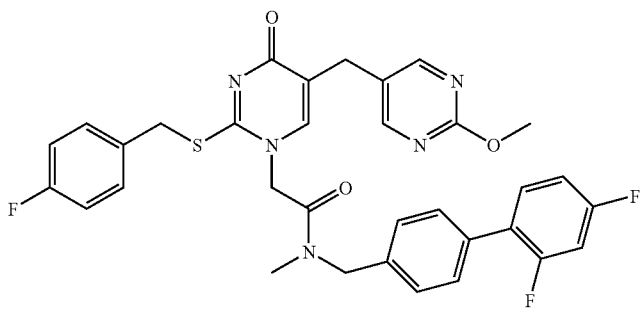 | 1-(N-methyl-N-(4-(2,4-difluorophenyl)-benzyl)aminocarbonylmethyl)-2-(4-fluorobenzyl)thio-5-(2-methoxy-5-pyrimidylmethyl)pyrimidin-4-one |

-continued

| Ex. No. | Precursors | Structure | Name |
|---|---|---|---|
| 110 | Int. A55<br>Int. B104 | 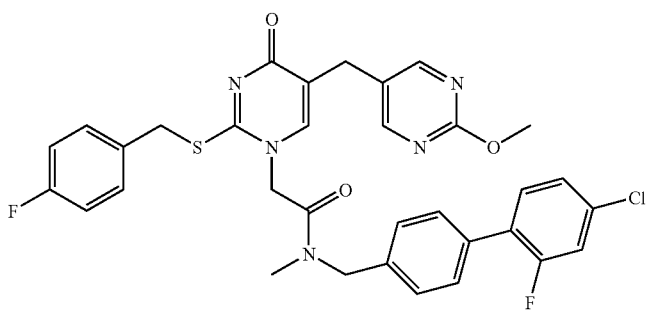 | 1-(N-methyl-N-(4-(2-fluoro-4-chloro-phenyl)benzyl)aminocarbonylmethyl)-2-(4-fluorobenzyl)thio-5-(2-methoxy-5-pyrimidylmethyl)pyrimidin-4-one |
| 111 | Int. A59<br>Int. B104 | 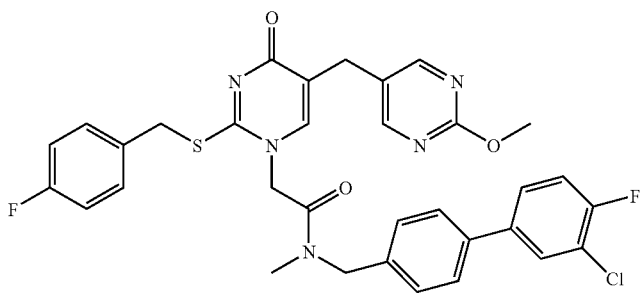 | 1-(N-methyl-N-(4-(3-chloro-4-fluoro-phenyl)benzyl)aminocarbonylmethyl)-2-(4-fluorobenzyl)thio-5-(2-methoxy-5-pyrimidylmethyl)pyrimidin-4-one |
| 112 | Int. A53<br>Int. B104 | 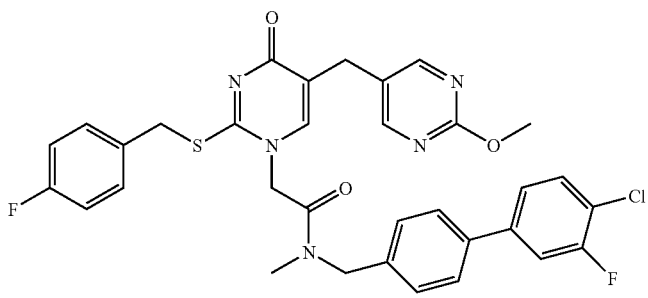 | 1-(N-methyl-N-(4-(3-fluoro-4-chloro-phenyl)benzyl)aminocarbonylmethyl)-2-(4-fluorobenzyl)thio-5-(2-methoxy-5-pyrimidylmethyl)pyrimidin-4-one |
| 113 | Int. A3<br>Int. B104 | 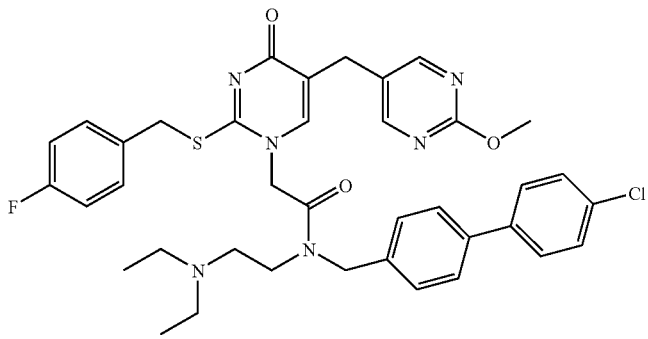 | 1-(N-(2-(diethylamino)ethyl)-N-(4-(4-chlorophenyl)benzyl)aminocarbonyl-methyl)-2-(4-fluorobenzyl)thio-5-(2-methoxy-5-pyrimidylmethyl)pyrimidin-4-one hydrochloride |

-continued

| Ex. No. | Precursors | Structure | Name |
|---|---|---|---|
| 114 | Int. A61<br>Int. B104 | 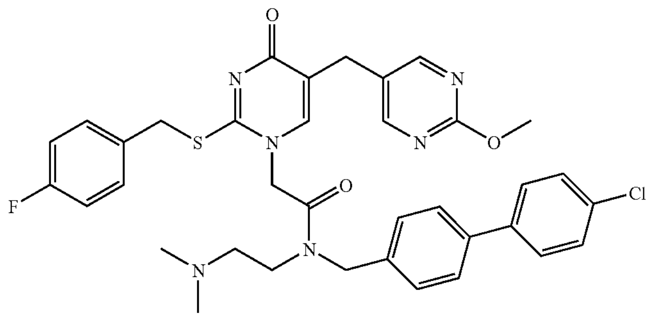 | 1-(N-(2-(dimethylamino)ethyl)-N-(4-(4-chlorophenyl)benzyl)aminocarbonylmethyl)-2-(4-fluorobenzyl)thio-5-(2-methoxy-5-pyrimidylmethyl)pyrimidin-4-one hydrochloride |
| 115 | Int. A70<br>Int. B104 | 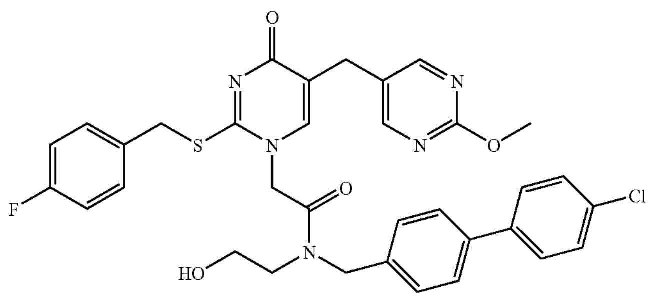 | 1-(N-(2-hydroxyethyl)-N-(4-(4-chlorophenyl)benzyl)aminocarbonylmethyl)-2-(4-fluorobenzyl)thio-5-(2-methoxy-5-pyrimidylmethyl)pyrimidin-4-one |
| 116 | Int. A51<br>Int. B104 | 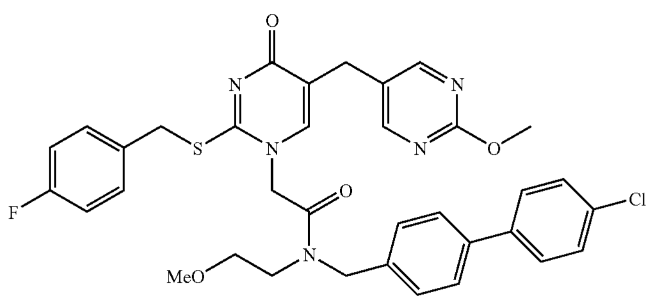 | 1-(N-(2-methoxyethyl)-N-(4-(4-chlorophenyl)benzyl)aminocarbonylmethyl)-2-(4-fluorobenzyl)thio-5-(2-methoxy-5-pyrimidylmethyl)pyrimidin-4-one |
| 117 | Int. A50<br>Int. B104 | 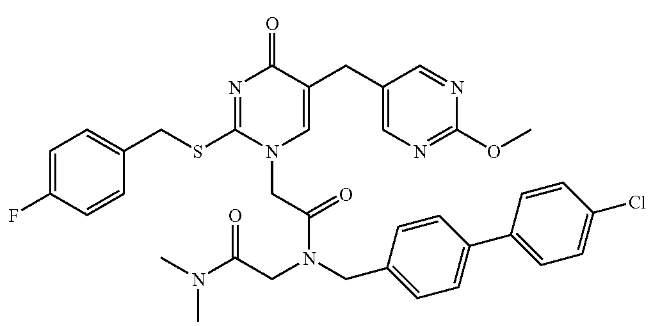 | 1-(N-(dimethylaminocarbonylmethyl)-N-(4-(4-chlorophenyl)benzyl)aminocarbonylmethyl)-2-(4-fluorobenzyl)thio-5-(2-methoxy-5-pyrimidylmethyl)-pyrimidin-4-one |
| 118 | Int. A11<br>Int. B104 | 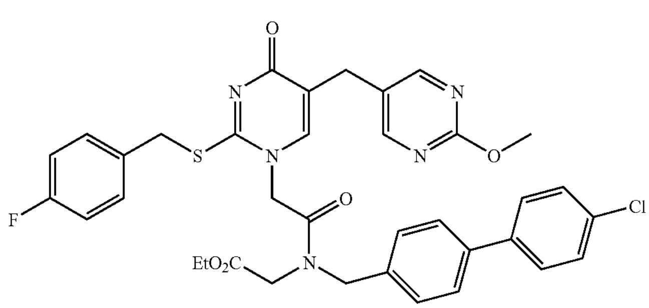 | 1-(N-(ethoxycarbonylmethyl)-N-(4-(4-chlorophenyl)benzyl)aminocarbonylmethyl)-2-(4-fluorobenzyl)thio-5-(2-methoxy-5-pyrimidylmethyl)pyrimidin-4-one |

| Ex. No. | Precursors | Structure | Name |
|---|---|---|---|
| 119 | Int. A48<br>Int. B104 | 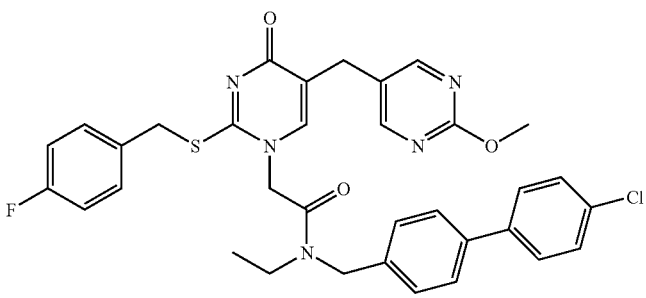 | 1-(N-ethyl-N-(4-(4-chlorophenyl)-benzyl)aminocarbonylmethyl)-2-(4-fluorobenzyl)thio-5-(2-methoxy-5-pyrimidylmethyl)pyrimidin-4-one |
| 120 | Int. A6<br>Int. B104 | 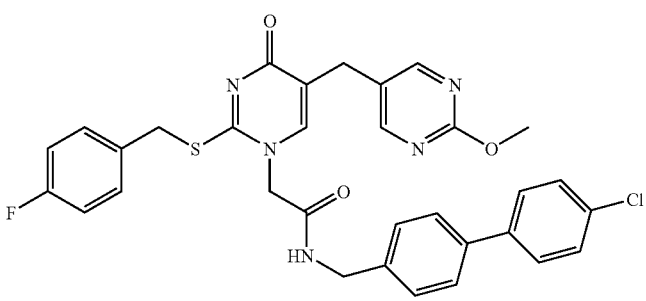 | 1-(4-(4-chlorophenyl)benzylaminocarbonylmethyl)-2-(4-fluorobenzyl)thio-5-(2-methoxy-5-pyrimidylmethyl)-pyrimidin-4-one |
| 121 | Int. A2<br>Int. B104 | 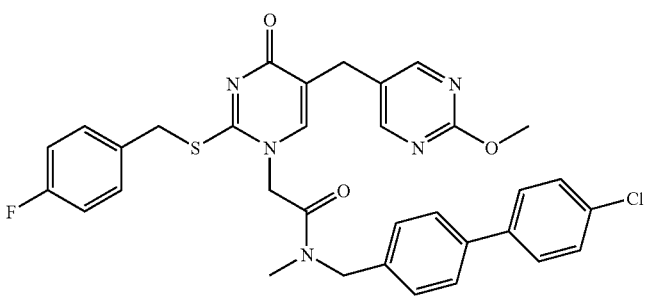 | 1-(N-methyl-N-(4-(4-chlorophenyl)-benzyl)aminocarbonylmethyl)-2-(4-fluorobenzyl)thio-5-(2-methoxy-5-pyrimidylmethyl)pyrimidin-4-one |
| 122 | Int. A120<br>Int. B104 | 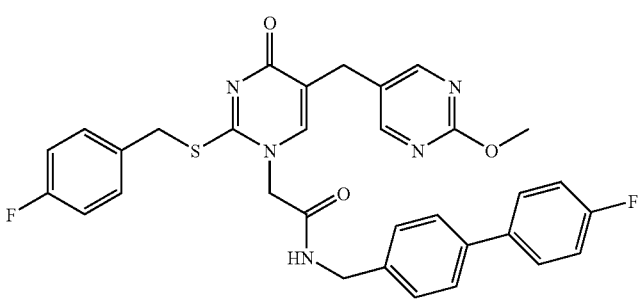 | 1-(4-(4-fluorophenyl)benzylaminocarbonylmethyl)-2-(4-fluorobenzyl)thio-5-(2-methoxy-5-pyrimidylmethyl)-pyrimidin-4-one |
| 123 | Int. A44<br>Int. B104 | 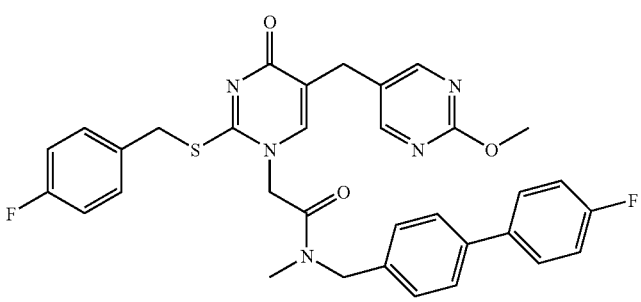 | 1-(N-methyl-N-(4-(4-fluorophenyl)-benzyl)aminocarbonylmethyl)-2-(4-fluorobenzyl)thio-5-(2-methoxy-5-pyrimidylmethyl)pyrimidin-4-one |

-continued

| Ex. No. | Precursors | Structure | Name |
|---|---|---|---|
| 125 | Int. A52<br>Int. B104 | 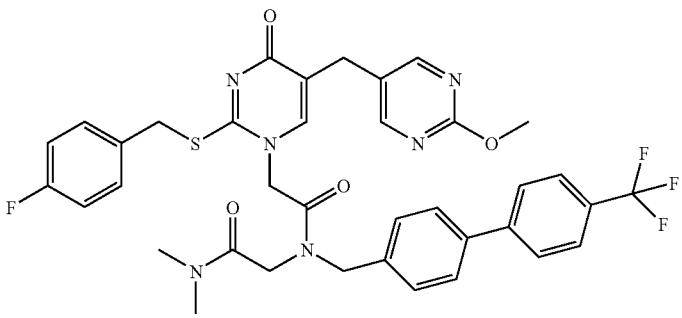 | 1-(N-(dimethylaminocarbonylmethyl)-N-(4-(4-trifluoromethylphenyl)benzyl)-aminocarbonylmethyl)-2-(4-fluorobenzyl)thio-5-(2-methoxy-5-pyrimidylmethyl)pyrimidin-4-one |
| 126 | Int. A45<br>Int. B104 | 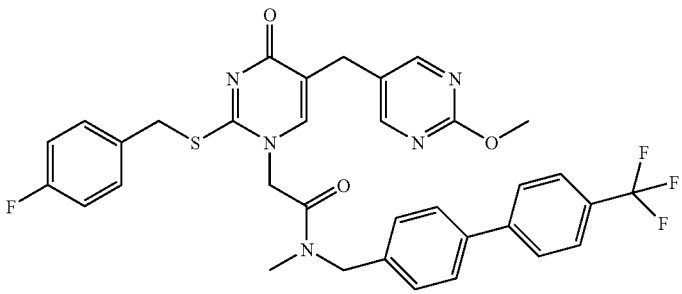 | 1-(N-methyl-N-(4-(4-trifluoromethylphenyl)benzyl)aminocarbonylmethyl)-2-(4-fluorobenzyl)thio-5-(2-methoxy-5-pyrimidylmethyl)pyrimidin-4-one |
| 127 | Int. A49<br>Int. B104 | 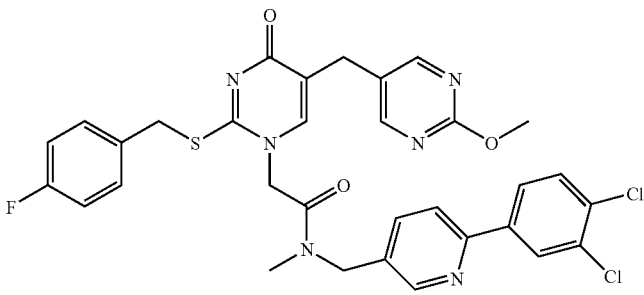 | 1-(N-methyl-N-(2-(3,4-dichlorophenyl)-pyrid-5-ylmethyl)aminocarbonylmethyl)-2-(4-fluorobenzyl)thio-5-(2-methoxy-5-pyrimidylmethyl)pyrimidin-4-one |
| 128 | Int. A65<br>Int. B104 | 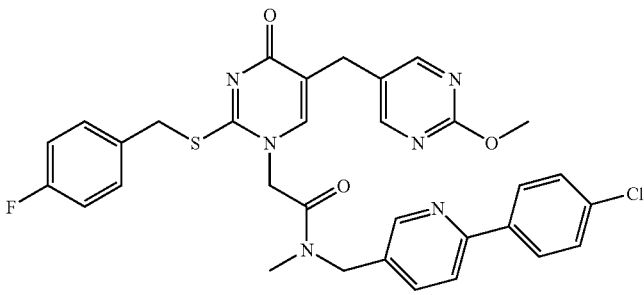 | 1-(2-(4-chlorophenyl)pyrid-5-ylmethyl)-aminocarbonylmethyl)-2-(4-fluorobenzyl)thio-5-(2-methoxy-5-pyrimidylmethyl)pyrimidin-4-one |
| 130 | Int. A6<br>Int. B98 | 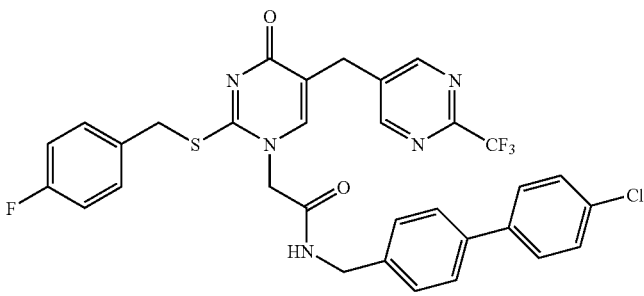 | 1-(4-(4-chlorophenyl)benzylaminocarbonylmethyl)-2-(4-fluorobenzyl)thio-5-(2-trifluoromethyl-5-pyrimidylmethyl)pyrimidin-4-one |

-continued

| Ex. No. | Precursors | Structure | Name |
|---|---|---|---|
| 131 | Int. A2<br>Int. B98 | 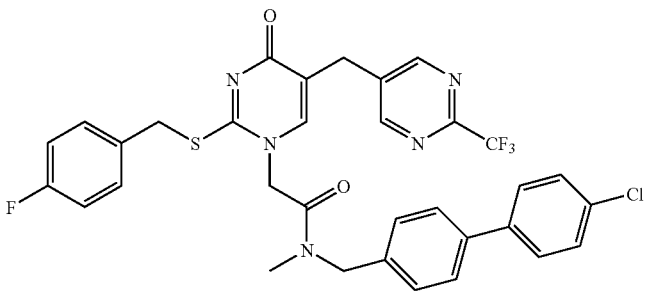 | 1-(N-methyl-N-(4-(4-chlorophenyl)-benzyl)aminocarbonylmethyl)-2-(4-fluorobenzyl)thio-5-(2-trifluoromethyl-5-pyrimidylmethyl)pyrimidin-4-one |
| 132 | Int. A73<br>Int. B94 | 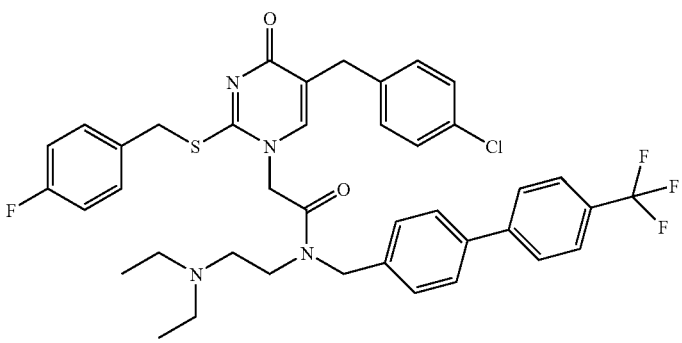 | 1-(N-(2-(diethylamino)ethyl)-N-(4-(4-trifluoromethylphenyl)benzyl)amino-carbonylmethyl)-2-(4-fluorobenzyl)thio-5-(4-chlorophenylmethyl)pyrimidin-4-one bitartrate |
| 133 | Int. A45<br>Int. B94 | 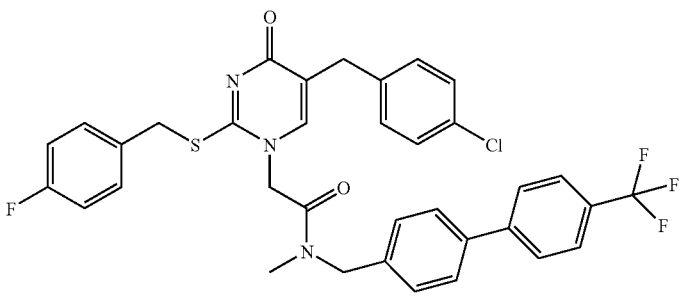 | 1-(N-methyl-N-(4-(4-trifluoromethyl-phenyl)benzyl)aminocarbonylmethyl)-2-(4-fluorobenzyl)thio-5-(4-chlorophenyl-methyl)pyrimidin-4-one |
| 134 | Int. A124<br>Int. B73 | 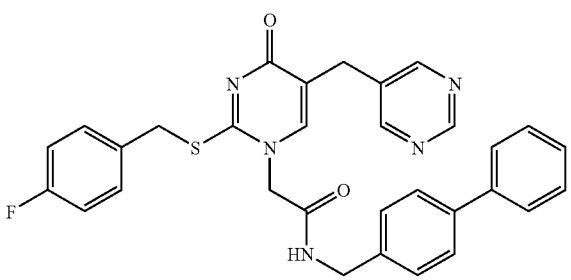 | 1-(4-phenylbenzylaminocarbonyl-methyl)-2-(4-fluorobenzyl)thio-5-(5-pyrimidylmethyl)pyrimidin-4-one |
| 135 | Int. A67<br>Int. B73 | 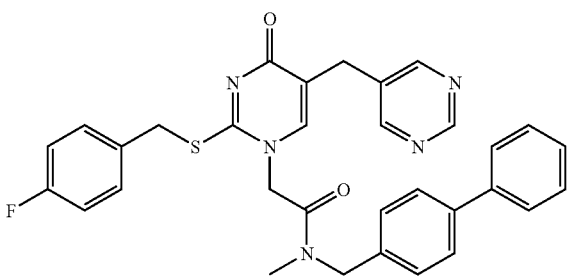 | 1-(N-methyl-N-(4-phenylbenzyl)amino-carbonylmethyl)-2-(4-fluorobenzyl)thio-5-(5-pyrimidylmethyl)pyrimidin-4-one |

-continued

| Ex. No. | Precursors | Structure | Name |
|---|---|---|---|
| 136 | Int. A73
Int. B93 | | 1-(N-(2-(diethylamino)ethyl)-N-(4-(4-trifluoromethylphenyl)benzyl)amino-carbonylmethyl)-2-(4-fluorobenzyl)thio-5-(phenylmethyl)pyrimidin-4-one bitartraze |
| 137 | Int. A45
Int. B93 | | 1-(N-methyl-N-(4-(4-trifluoromethyl-phenyl)benzyl)aminocarbonylmethyl)-2-(4-fluorobenzyl)thio-5-(phenylmethyl)-pyrimidin-4-one |
| 138 | Int. A73
Int. B101 | | 1-(N-(2-(diethylamino)ethyl)-N-(4-(4-chlorophenyl)benzyl)aminocarbonyl-methyl)-2-(4-fluorobenzyl)thio-5-(2-(4-morpholino)pyrimid-5-ylmethyl)-pyrimidin-4-one |

The following Examples were made by the method of Example 4; the salts were subsequently prepared by the methods of Examples 7–8 as appropriate:

| Ex. No. | Precursors | Structure | Name |
|---|---|---|---|
| 140 | Int. A155
Int. B63 | | 1-(N-methyl-N-(4-(4-trifluoromethyl-phenyl)benzyl)aminocarbonylmethyl)-2-(2-methylthiazol-4-yl)methylthio-5-(2-methoxy-5-pyrimidylmethyl)-pyrimidin-4-one |

-continued

| Ex. No. | Precursors | Structure | Name |
|---|---|---|---|
| 141 | Int. A155<br>Int. B62 | 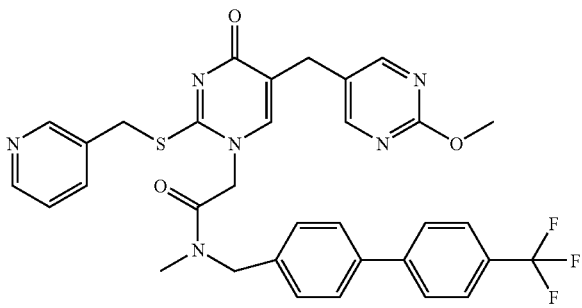 | 1-(N-methyl-N-(4-(4-trifluoromethyl-phenyl)benzyl)aminocarbonylmethyl)-2-(pyrid-3-yl)methylthio-5-(2-methoxy-5-pyrimidyl-methyl)pyrimidin-4-one |

The following Examples were made by the method of Example 22; the salts were subsequently prepared by the methods of Examples 7–8 as appropriate:

| Ex. No. | Precursors | Structure | Name |
|---|---|---|---|
| 150 | Int. A90<br>Int. B71 | 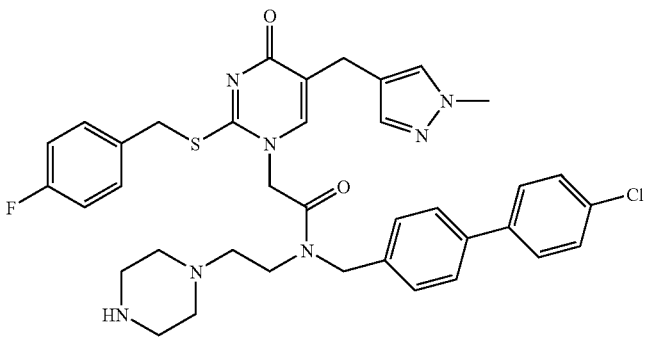 | 1-(N-(2-(1-piperazino)ethyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 151 | Int. A86<br>Int. B71 | 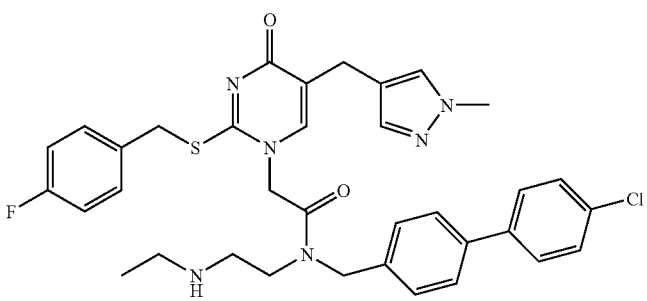 | 1-(N-(2-ethylamino)ethyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 152 | Int. A85<br>Int. B71 | 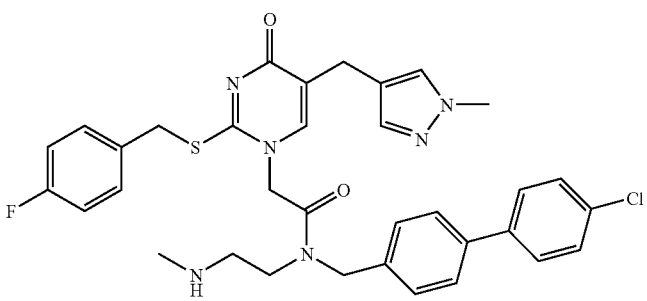 | 1-(N-(2-methylamino)ethyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |

-continued

| Ex. No. | Precursors | Structure | Name |
|---|---|---|---|
| 153 | Int. A91<br>Int. B71 | 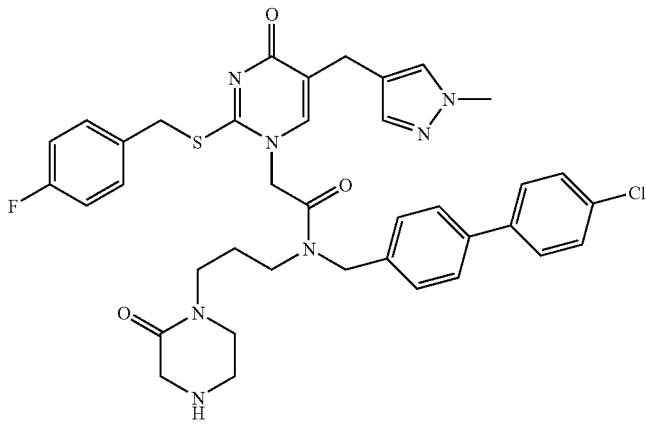 | 1-(N-(3-(2-oxo-1-piperazino)propyl)-N-(4-(4-chlorophenyl)benzyl)amino-carbonylmethyl)-2-(4-fluorobenzyl)thio-5-(1-methyl-4-pyrazolylmethyl)pyrimidin-4-one hydrochloride |
| 154 | Int. A89<br>Int. B71 | 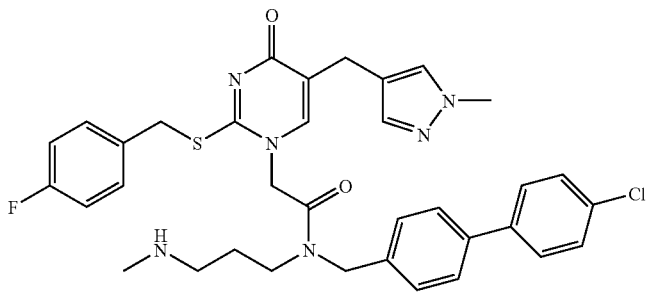 | 1-(N-(3-(methylamino)propyl)-N-(4-(4-chlorophenyl)benzyl)aminocarbonyl-methyl)-2-(4-fluorobenzyl)thio-5-(1-methyl-4-pyrazolylmethyl)pyrimidin-4-one hydrochloride |
| 155 | Int. A88<br>Int. B71 | 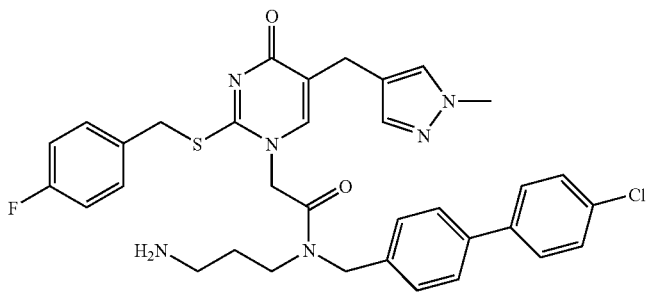 | 1-(N-(3-aminopropyl)-N-(4-(4-chloro-phenyl)benzyl)aminocarbonylmethyl)-2-(4-fluorobenzyl)thio-5-(1-methyl-4-pyrazolylmethyl)pyrimidin-4-one hydrochloride |
| 156 | Int. A87<br>Int. B71 | 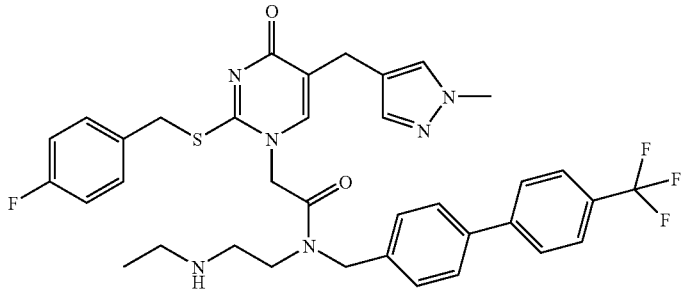 | 1-(N-(2-(ethylamino)ethyl)-N-(4-(4-trifluoromethylphenyl)benzyl)amino-carbonylmethyl)-2-(4-fluorobenzyl)thio-5-(1-methyl-4-pyrazolyl-methyl)pyrimidin-4-one-bitartrate |

The following Example was made by the method of Example 21:

| Ex. No. | Precursor | Structure | Name |
|---|---|---|---|
| 157 | Ex. 118 | 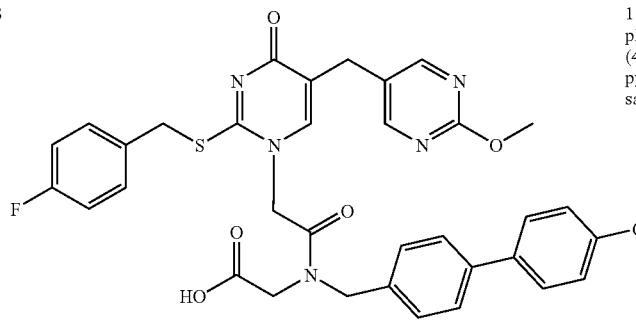 | 1(N-(carboxymethyl)-N-(4-(4-chlorophenyl)benzyl)aminocarbonylmethyl)-2-(4-fluorobenzyl)thio-5-(2-methoxy-5-pyrimidylmethyl)pyrimidin-4-one, sodium salt |

Biological Data
1. Screen for Lp-PLA$_2$ inhibition.

Enzyme activity was determined by measuring the rate of turnover of the artificial substrate (A) at 37° C. in 50 mM HEPES (N-2-hydroxyethylpiperazine-N'-2-ethanesulphonic acid) buffer containing 150 mM NaCl, pH 7.4.

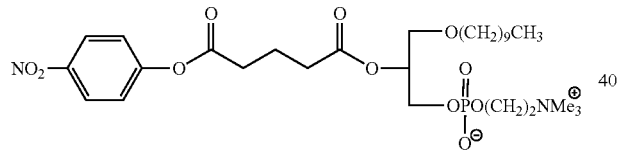

(A)

Assays were performed in 96 well titre plates.

Recombinant Lp PLA2 was purified to homogeneity from baculovirus infected Sf9 cells, using a zinc chelating column, blue sepharose affinity chromatography and an anion exchange column. Following purification and ultrafiltration, the enzyme was stored at 6 mg/ml at 4° C. Assay plates of compound or vehicle plus buffer were set up using automated robotics to a volume of 170 µl. The reaction was initiated by the addition of 20 µl of 10× substrate (A) to give a final substrate concentration of 20 µM and 10 µl of diluted enzyme to a final 0.2 nM LpPLA2.

The reaction was followed at 405 nm and 37° C. for 20 minutes using a plate reader with automatic mixing. The rate of reaction was measured as the rate of change of absorbance.

Results

The compounds described in the Examples were tested as described above and had IC$_{50}$ values in the range 0.001 to 0.00005 µM.

What is claimed is:
1. A compound of formula (I):

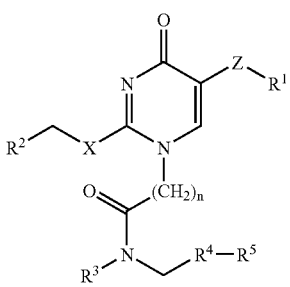

(I)

in which:

R$^1$ is an aryl or heteroaryl group, optionally substituted by 1, 2, 3 or 4 substituents which may be the same or different selected from C$_{(1-18)}$alkyl, C$_{(1-18)}$alkoxy, C$_{(1-18)}$alkylthio, arylC$_{(1-18)}$alkoxy, hydroxy, halogen, CN, COR$^6$, carboxy, COOR$^6$, CONR$^9$R$^{10}$, NR$^6$COR$^7$, SO$_2$NR$^9$R$^{10}$, NR$^6$SO$_2$R$^7$, NR$^9$R$^{10}$, mono to perfluoro-C$_{(1-4)}$alkyl and mono to perfluoro-C$_{(1-4)}$alkoxy, oxo, CH$_2$COOH or a salt thereof, CH$_2$COOR$^8$, CH$_2$CONR$^9$R$^{10}$, CH$_2$CN, (CH$_2$)$_m$NR$^9$R$^{10}$, (CH$_2$)$_m$OH or (CH$_2$)$_m$OR$^6$ where m is an integer from 1 to 3;

R$^2$ is an aryl or heteroaryl group, optionally substituted by 1, 2, 3 or 4 substituents which may be the same or different selected from C$_{(1-18)}$alkyl, C$_{(1-18)}$alkoxy, C$_{(1-18)}$alkylthio, arylC$_{(1-18)}$alkoxy, hydroxy, halogen, CN, COR$^6$, carboxy, COOR$^6$, CONR$^9$R$^{10}$, NR$^6$COR$^7$, SO$_2$NR$^9$R$^{10}$, NR$^6$SO$_2$R$^7$, NR$^9$R$^{10}$, mono to perfluoro-C$_{(1-4)}$alkyl, mono to perfluoro-C$_{(1-4)}$alkoxy, and aryl C$_{(1-4)}$alkyl;

R$^3$ is hydrogen or C$_{(1-4)}$alkyl which may be unsubstituted or substituted by hydroxy, OR$^6$, COR$^6$, carboxy, COOR$^6$, CONR$^9$R$^{10}$, NR$^9$R$^{10}$, mono- or di-(hydroxy C$_{(1-6)}$alkyl)amino or N-hydroxyC$_{(1-6)}$alkyl-N-C$_{(1-6)}$alkyl amino;

R$^4$ is an aryl or a heteroaryl ring optionally substituted by 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl and mono to perfluoro-$C_{(1-4)}$alkoxy;

$R^5$ is an aryl ring which is further optionally substituted by 1, 2, 3 or 4 substituents which may be the same or different selected from $C_{1-18}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl and mono to perfluoro-$C_{(1-4)}$alkoxy;

$R^6$ and $R^7$ are independently hydrogen or $C_{(1-20)}$alkyl, for instance $C_{(1-4)}$alkyl (e.g. methyl or ethyl);

$R^8$ is $C_{(1-4)}$alkyl or a pharmaceutically acceptable in vivo hydrolysable ester group;

$R^9$ and $R^{10}$ which may be the same or different is each selected from hydrogen, $C_{(1-12)}$alkyl, $CH_2R^{11}$, $CHR^{12}CO_2H$ or a salt thereof, or $R^9$ and $R^{10}$ together with the nitrogen to which they are attached form a 4- to 7-, preferably 5- to 7-, membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylCO, or aryl;

$R^{11}$ is COOH or a salt thereof, $COOR^8$, $CONR^6R^7$, CN, $CH_2OH$ or $CH_2OR^6$;

$R^{12}$ is an amino acid side chain;

n is an integer from 1 to 4, preferably 1 or 3;

X is O or S; and

Z is $CR^{13}R^{14}$ where $R^{13}$ and $R^{14}$ are each hydrogen or $C_{(1-4)}$alkyl, or $R^{13}$ and $R^{14}$ together with the intervening carbon atom form a $C_{(3-6)}$cycloalkyl ring.

2. A compound of formula (I) as claimed in claim 1 in which Z is $CH_2$.

3. A compound of formula (I) as claimed in claim 1 in which $R^1$ is an aryl group selected from phenyl and naphthyl or a heteroaryl group which comprises a 5- or 6- membered, monocyclic heteroaryl group comprising 1 or 2 nitrogen heteroatoms.

4. A compound of formula (I) as claimed in claim 1 in which $R^1$ is pyrimidyl optionally substituted by 1 or 2 substituents selected from oxo, aryl$C_{(1-4)}$alkyl, $C_{(1-6)}$alkyl, $C_{(3-6)}$cycloalkyl, hydroxy, $C_{(1-4)}$alkoxy, carboxy$C_{(1-6)}$alkyl, $C_{(1-6)}$alkylcarboxy$C_{(1-6)}$alkyl, di-$C_{(1-6)}$alkylamino, and morpholino; or pyrazolyl optionally substituted by $C_{(1-6)}$alkyl.

5. A compound as claimed in claim 4 in which $ZR^1$ is pyrimid-5-ylmethyl optionally substituted by 2-methoxy, 2-trifluoromethyl, 2-(4-morpholino) or 2-dimethylamino; 2-oxo-pyrimid-5-ylmethyl or 1-methyl-4-pyrazolylmethyl.

6. A compound of formula (I) as claimed in claim 1 in which X is S.

7. A compound of formula (I) as claimed in claim 1 in which $R^2$ is an aryl group selected from phenyl and naphthyl or a heteroaryl group selected from pyridyl, pyrimidinyl, pyrazolyl, furanyl, thienyl, thiazolyl, quinolyl, benzothiazolyl, pyridazolyl and pyrazinyl.

8. A compound of formula (I) as claimed in claim 7 in which $R^2$ is phenyl optionally substituted by halogen.

9. A compound of formula (I) as claimed in claim 1 in which $R^3$ is selected from hydrogen; and methyl, ethyl and propyl, optionally substituted by amino, $C_{(1-3)}$alkylamino, di $C_{(1-3)}$alkylamino, hydroxy$C_{(1-3)}$alkylamino, hydroxy, $C_{(1-3)}$alkoxy, carboxy, $C_{(1-3)}$alkylcarboxy, and heterocycyl.

10. A compound of formula (I) as claimed in claim 1 in which $R^4$ is selected from phenyl optionally substituted by halogen; thiophene; pyridine; and pyrimidine.

11. A compound of formula (I) as claimed in claim 1 in which $R^5$ is phenyl optionally substituted by halogen, trifluoromethyl, or trifluoromethoxy.

12. A compound of formula (I) as claimed in claim 10 in which $R^4$ and $R^5$ together form a 4-(phenyl)phenyl substituent in which the remote phenyl ring may be optionally substituted by halogen or trifluoromethyl.

13. A compound of formula (I) as claimed in claim 1 selected from the group consisting of:

1-(N-methyl-N-(4-(4-chlorophenyl)benzyl)aminocarbonylmethyl)-2-(4-fluorobenzyl)thio-5-(1-methylpyrazol-4-ylmethyl)pyrimidin-4-one;

1-(N-methyl-N-(4-(4-trifluoromethylphenyl)benzyl)aminocarbonylmethyl)-2-(4-fluorobenzyl)thio-5-(1-methylpyrazol-4-ylmethyl)pyrimidin-4-one;

1-(N-(2-dimethylaminoethyl)-N-(4-(4-chlorophenyl)benzyl)aminocarbonyl methyl)-2-(4-fluorobenzyl)thio-5-(1-methylpyrazol-4-ylmethyl)pyrimidin-4-one;

1-(N-methyl-N-(4-(4-chlorophenyl)benzyl)aminocarbonylmethyl)-2-(4-fluorobenzyl)thio-5-(2-(4-morpholino)pyrimid-5-ylmethyl)pyrimidin-4-one;

1-(N-(2-(dimethylamino)ethyl)-N-(4-(4-trifluoromethylphenyl)benzyl)amino carbonylmethyl)-2-(4-fluorobenzyl)thio-5-(1-methyl-4-pyrazolylmethyl)pyrimidin-4-one;

1-(N-(2-(diethylamino)ethyl)-N-(4-(4-chlorophenyl)benzyl)aminocarbonyl methyl)-2-(4-fluorobenzyl)thio-5-(1-methyl-4-pyrazolylmethyl)pyrimidin-4-one;

1-(N-(2-(diethylamino)ethyl)-N-(2-(4-trifluoromethylphenyl)pyrid-5-ylmethyl) aminocarbonylmethyl)-2-(4-fluorobenzyl)thio-5-(1-methyl-4-pyrazolylmethyl)pyrimidin-4-one;

1-(N-(2-(1-piperidino)ethyl)-N-(4-(4-trifluoromethylphenyl)benzyl)amino carbonylmethyl)-2-(4-fluorobenzyl)thio-5-(1-methyl-4-pyrazolylmethyl)pyrimidin-4-one bitartrate;

1-(N-(carboxymethyl)-N-(4-(4-trifluoromethylphenyl)benzyl)aminocarbonyl methyl)-2-(4-fluorobenzyl)thio-5-(1-methyl-4-pyrazolylmethyl)pyrimidin-4-one sodium salt; or a pharmaceutically acceptable salt thereof.

14. A pharmaceutical composition comprising a compound of formula (I) as claimed in claim 13 and a pharmaceutically acceptable carrier.

15. A method of treating atherosclerosis which method comprises administering to a patient in need thereof an effective amount of a compound of formula (I) as claimed in claim 1 and a statin.

16. A process for preparing a compound of formula (I)

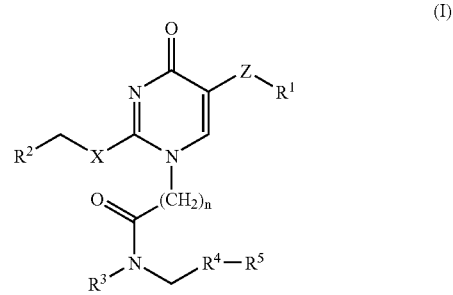

in which:

$R^1$ is an aryl or heteroaryl group, optionally substituted by 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alky and mono to perfluoro-$C_{(1-4)}$alkoxy, oxo, $CH_2COOH$ or a salt thereof, $CH_2COOR^8$, $CH_2CONR^9R^{10}$, $CH_2CN$, $(CH_2)_mNR^9R^{10}$, $(CH_2)_mOH$ or $(CH_2)_mOR^6$ where m is an integer from 1 to 3;

$R^2$ is an aryl or heteroaryl group, optionally substituted 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl, mono to perfluoro-$C_{(1-4)}$alkoxy, and aryl$C_{(1-4)}$alkyl;

$R^3$ is hydrogen or $C_{(1-4)}$alkyl which may be unsubstituted or substituted by hydroxy, $OR^6$, $COR^6$, carboxy, $COOR^6$, $CONR^9R^{10}$, $NR^9R^{10}$, mono- or di-(hydroxy $C_{(1-6)}$alkyl)amino or N-hydroxy$C_{(1-6)}$alkyl-N-$C_{(1-6)}$alkyl amino;

$R^4$ is an aryl or a heteroaryl ring optionally substituted by 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl and mono to perfluoro-$C_{(1-4)}$alkoxy;

$R^5$ is an aryl ring which is further optionally substituted by 1, 2, 3 or 4 substituents which may be the same or different selected from $C_{(1-18)}$alkyl, $C_{(1-18)}$alkoxy, $C_{(1-18)}$alkylthio, aryl$C_{(1-18)}$alkoxy, hydroxy, halogen, CN, $COR^6$, carboxy, $COOR^6$, $CONR^9R^{10}$, $NR^6COR^7$, $SO_2NR^9R^{10}$, $NR^6SO_2R^7$, $NR^9R^{10}$, mono to perfluoro-$C_{(1-4)}$alkyl and mono to perfluoro-$C_{(1-4)}$alkoxy;

$R^6$ and $R^7$ are independently hydrogen or $C_{(1-20)}$alkyl, for instance $C_{(1-4)}$alkyl (e.g. methyl or ethyl);

$R^8$ is $C_{(1-4)}$alkyl or a pharmaceutically acceptable in vivo hydrolysable ester group;

$R^9$ and $R^{10}$ which may be the same or different is each selected from hydrogen, $C_{(1-12)}$alkyl, $CH_2R^{11}$, $CHR^{12}CO_2H$ or a salt thereof, or $R^9$ and $R^{10}$ together with the nitrogen to which they are attached form a 4- to 7-, preferably 5- to 7-, membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylCO, or aryl;

$R^{11}$ is COOH or a salt thereof, $COOR^8$, $CONR^6R^7$, CN, $CH_2OH$ or $CH_2OR^6$;

$R^{12}$ is an amino acid side chain;

n is an integer from 1 to 4, preferably 1 or 3;

X is O or S; and

Z is $CR^{13}R^{14}$ where $R^{13}$ and $R^{14}$ are each hydrogen or $C_{(1-4)}$alkyl, or $R^{13}$ and $R^{14}$ together with the intervening carbon atom form a $C_{(3-6)}$cycloalkyl ring;

which process comprises:

(a) reacting a compound of formula (II):

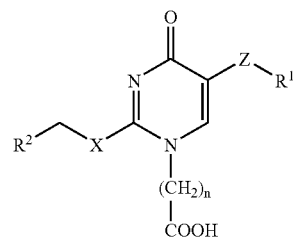

(II)

in which X, Y, Z, $R^1$ and $R^2$ are the same as defined herein above for formula (I),
with a compound of formula (III):

$R^5—R^4—CH_2NHR^3$ (III)

in which $R^3$, $R^4$ and $R^5$ are the same as defined herein above for formula (I); under amide forming conditions;

(b) reacting a compound of formula (IV):

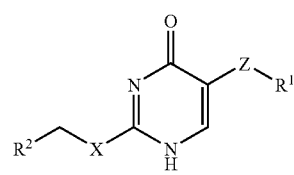

(IV)

in which X, Z, $R^1$ and $R^2$ are the same as defined herein above for formula (I), with a compound of formula (V):

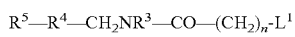

$R^5—R^4—CH_2NR^3—CO—(CH_2)_n-L^1$ (V)

in which n, $R^3$, $R^4$ and $R^5$ are the same as defined herein above for formula (I), and $L^1$ is a leaving group such as halogen; in the presence of a base such as a secondary or tertiary amine, in an inert solvent;

(c) when X is S, reacting a compound of formula (VI):

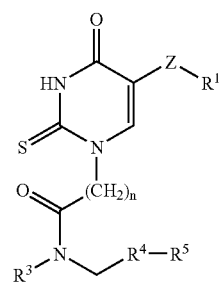

(VI)

in which n, Z, $R^1$, $R^3$, $R^4$ and $R^5$ are the same as defined herein above for formula (I), with a compound of formula (VII):

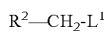

$R^2—CH_2-L^1$ (VII)

in which $R^2$ and $L^1$ are the same as defined herein above for formula (I), in the presence of a base such as a secondary or tertiary amine, in an inert solvent; or (d) when X is O, reacting a compound of formula (VIII):

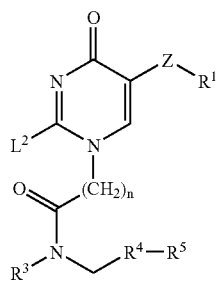

(VIII)

in which n, Z, $R^1$, $R^3$, $R^4$ and $R^5$ are the same as defined herein above for formula (I), and $L^2$ is a leaving group, with a compound of formula (IX):

$$R^2—CH_2—OH \quad \quad (IX)$$

in which $R^2$ is the same as defined herein above for formula (I), in the presence of a base, in an inert solvent.

17. A pharmaceutical composition comprising a compound of formula (I) as claimed in claim 1 and a pharmaceutically acceptable carrier.

18. A method of treating atherosclerosis which method comprises administering to a patient in need thereof an effective amount of a compound of formula (I) as claimed in claim 1 to a patient in need thereof.

* * * * *